US008926697B2

(12) United States Patent  
Gross et al.

(10) Patent No.: US 8,926,697 B2
(45) Date of Patent: Jan. 6, 2015

(54) CLOSED BAND FOR PERCUTANEOUS ANNULOPLASTY

(75) Inventors: Amir Gross, Tel-Aviv (IL); Tal Sheps, Givat Shmuel (IL); Tal Hammer, Ramat Gan (IL); Tal Reich, Binyamina (IL)

(73) Assignee: Valtech Cardio, Ltd., Or Yehuda (IL)

( * ) Notice: Subject to any disclaimer, the term of this patent is extended or adjusted under 35 U.S.C. 154(b) by 0 days.

(21) Appl. No.: 13/167,492

(22) Filed: Jun. 23, 2011

(65) Prior Publication Data

US 2012/0330411 A1 Dec. 27, 2012

(51) Int. Cl.
*A61F 2/24* (2006.01)
(52) U.S. Cl.
CPC ............. *A61F 2/2445* (2013.01); *A61F 2/2466* (2013.01)
USPC ........................................................ 623/2.37
(58) Field of Classification Search
USPC ................................................. 623/2.36–2.37
See application file for complete search history.

(56) References Cited

U.S. PATENT DOCUMENTS

| 3,604,488 | A | 9/1971 | Wishart et al. |
|---|---|---|---|
| 4,042,979 | A | 8/1977 | Angell |
| 4,118,805 | A | 10/1978 | Reimels |
| 4,434,828 | A | 3/1984 | Trincia |
| 4,602,911 | A | 7/1986 | Ahmandi et al. |
| 4,917,698 | A | 4/1990 | Carpentier et al. |
| 5,061,277 | A | 10/1991 | Carpentier et al. |
| 5,104,407 | A | 4/1992 | Lam et al. |
| 5,300,034 | A | 4/1994 | Behnke et al. |
| 5,306,296 | A | 4/1994 | Wright et al. |
| 5,477,856 | A | 12/1995 | Lundquist |
| 5,669,919 | A | 9/1997 | Sanders et al. |
| 5,674,279 | A | 10/1997 | Wright et al. |
| 5,810,882 | A | 9/1998 | Bolduc |
| 5,876,373 | A | 3/1999 | Giba et al. |

(Continued)

FOREIGN PATENT DOCUMENTS

| WO | WO 01/26586 A1 | 4/2001 |
|---|---|---|
| WO | WO 02/085251 A1 | 10/2002 |

(Continued)

OTHER PUBLICATIONS

Amplatzer ® Cribriform Occluder. A patient guide to Percutaneous, Transcatheter, Atrial Septal Defect Closure, AGA Medical Corporation, Apr. 2008.

(Continued)

*Primary Examiner* — Andrew Iwamaye
*Assistant Examiner* — Leslie Coburn
(74) *Attorney, Agent, or Firm* — Sughrue Mion, PLLC

(57) ABSTRACT

An implantable structure includes a flexible sleeve, having first and second sleeve ends, and a contracting assembly, which is configured to longitudinally contract the sleeve, and includes a contracting mechanism, which is disposed longitudinally at a first site of the sleeve, and a longitudinal contracting member, having (a) a first member end, (b) a second member end, which is coupled to the sleeve longitudinally at a second site longitudinally between the first site and the second sleeve end, exclusive, and (c) a first member end portion, which is coupled to the contracting mechanism. The sleeve is arranged in a closed loop, such that first and second portions of the sleeve together define a longitudinally overlapping portion of the sleeve. The implantable structure is configured such that the contracting assembly longitudinally applies a longitudinal contracting force only between the first and the second sites, and not along the overlapping portion.

32 Claims, 28 Drawing Sheets

(56) References Cited

U.S. PATENT DOCUMENTS

| | | |
|---|---|---|
| 5,961,440 A | 10/1999 | Schweich, Jr. et al. |
| 5,961,539 A | 10/1999 | Northrup, III et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,143,024 A | 11/2000 | Campbell |
| 6,165,119 A | 12/2000 | Schweich, Jr. et al. |
| 6,183,411 B1 | 2/2001 | Mortier |
| 6,187,040 B1 | 2/2001 | Wright |
| 6,251,092 B1 | 6/2001 | Qin et al. |
| 6,319,281 B1 | 11/2001 | Patel |
| 6,332,893 B1 | 12/2001 | Mortier et al. |
| 6,402,780 B2 | 6/2002 | Williamson, IV |
| 6,406,420 B1 | 6/2002 | McCarthy et al. |
| 6,451,054 B1 | 9/2002 | Stevens |
| 6,470,892 B1 | 10/2002 | Forsell |
| 6,524,338 B1 | 2/2003 | Gundry |
| 6,537,314 B2 | 3/2003 | Langberg et al. |
| 6,547,801 B1 | 4/2003 | Dargent |
| 6,564,805 B2 | 5/2003 | Garrison et al. |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,602,289 B1 | 8/2003 | Colvin et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,651,671 B1 | 11/2003 | Donlon et al. |
| 6,652,556 B1 | 11/2003 | VanTassel |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,709,456 B2 | 3/2004 | Langberg et al. |
| 6,718,985 B2 | 4/2004 | Hlavka et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,786,924 B2 | 9/2004 | Ryan et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,855,126 B2 | 2/2005 | Flinchbaugh |
| 6,858,039 B2 | 2/2005 | McCarthy |
| 6,893,459 B1 | 5/2005 | Macoviak |
| 6,908,482 B2 | 6/2005 | McCarthy et al. |
| 6,960,217 B2 | 11/2005 | Bolduc |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,862 B2 | 7/2006 | Vidlund |
| 7,087,064 B1 | 8/2006 | Hyde |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,238,191 B2 | 7/2007 | Bachmann |
| 7,294,148 B2 | 11/2007 | McCarthy |
| 7,297,150 B2 | 11/2007 | Cartledge et al. |
| 7,311,728 B2 | 12/2007 | Solem et al. |
| 7,329,280 B2 | 2/2008 | Bolling et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,753,924 B2 | 7/2010 | Starksen et al. |
| 7,992,567 B2 | 8/2011 | Hirotsuka |
| 8,070,804 B2 | 12/2011 | Hyde |
| 8,123,800 B2 | 2/2012 | McCarthy |
| 8,142,495 B2 | 3/2012 | Hasenkam |
| 8,152,844 B2 | 4/2012 | Rao |
| 8,226,711 B2 | 7/2012 | Mortier |
| 8,241,351 B2 | 8/2012 | Cabiri |
| 8,287,591 B2 | 10/2012 | Keidar |
| 8,353,956 B2 | 1/2013 | Miller |
| 8,523,940 B2 | 9/2013 | Richardson |
| 2001/0021874 A1 | 9/2001 | Carpentier et al. |
| 2002/0042621 A1* | 4/2002 | Liddicoat et al. ............ 606/151 |
| 2002/0087048 A1 | 7/2002 | Brock et al. |
| 2002/0103532 A1 | 8/2002 | Langberg et al. |
| 2002/0151961 A1 | 10/2002 | Lashinski |
| 2002/0173841 A1 | 11/2002 | Ortiz et al. |
| 2003/0050693 A1 | 3/2003 | Quijano et al. |
| 2003/0105519 A1 | 6/2003 | Fasol et al. |
| 2003/0167062 A1 | 9/2003 | Gambale et al. |
| 2003/0229350 A1 | 12/2003 | Kay |
| 2003/0229395 A1 | 12/2003 | Cox |
| 2003/0233142 A1 | 12/2003 | Morales et al. |
| 2004/0122514 A1 | 6/2004 | Fogarty et al. |
| 2004/0133274 A1 | 7/2004 | Webler |
| 2004/0138744 A1 | 7/2004 | Lashinski et al. |
| 2004/0148021 A1 | 7/2004 | Cartledge et al. |
| 2004/0186566 A1 | 9/2004 | Hindrichs et al. |
| 2004/0236419 A1 | 11/2004 | Milo |
| 2005/0004668 A1 | 1/2005 | Aklog et al. |
| 2005/0010787 A1 | 1/2005 | Tarbouriech |
| 2005/0055087 A1 | 3/2005 | Starksen |
| 2005/0060030 A1 | 3/2005 | Lashinski et al. |
| 2005/0065601 A1 | 3/2005 | Lee |
| 2005/0085903 A1 | 4/2005 | Lau |
| 2005/0090827 A1 | 4/2005 | Gedebou |
| 2005/0107871 A1 | 5/2005 | Realyvasquez et al. |
| 2005/0125011 A1 | 6/2005 | Spence et al. |
| 2005/0171601 A1 | 8/2005 | Cosgrove et al. |
| 2005/0203549 A1 | 9/2005 | Realyvasquez |
| 2005/0216039 A1 | 9/2005 | Lederman |
| 2005/0216079 A1 | 9/2005 | MaCoviak |
| 2005/0288781 A1 | 12/2005 | Moaddeb et al. |
| 2006/0025787 A1 | 2/2006 | Morales et al. |
| 2006/0041319 A1 | 2/2006 | Taylor et al. |
| 2006/0085012 A1 | 4/2006 | Dolan |
| 2006/0241656 A1 | 10/2006 | Starksen et al. |
| 2006/0241748 A1 | 10/2006 | Lee et al. |
| 2007/0016287 A1 | 1/2007 | Cartledge et al. |
| 2007/0016288 A1 | 1/2007 | Gurskis |
| 2007/0027536 A1 | 2/2007 | Mihaljevic et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0162111 A1 | 7/2007 | Fukamachi et al. |
| 2007/0213582 A1 | 9/2007 | Zollinger et al. |
| 2007/0219558 A1 | 9/2007 | Deutsch |
| 2007/0244556 A1 | 10/2007 | Rafiee et al. |
| 2007/0255397 A1 | 11/2007 | Ryan |
| 2007/0255400 A1 | 11/2007 | Parravicini et al. |
| 2007/0282375 A1 | 12/2007 | Hindrichs et al. |
| 2007/0295172 A1 | 12/2007 | Swartz |
| 2008/0004697 A1 | 1/2008 | Lichtenstein et al. |
| 2008/0027483 A1 | 1/2008 | Catrledge et al. |

(56) References Cited

U.S. PATENT DOCUMENTS

| | | | |
|---|---|---|---|
| 2008/0051703 A1 | 2/2008 | Thornton | |
| 2008/0058595 A1 | 3/2008 | Snoke et al. | |
| 2008/0086203 A1 | 4/2008 | Roberts | |
| 2008/0167714 A1 | 7/2008 | St. Goar | |
| 2008/0177382 A1 | 7/2008 | Hyde | |
| 2008/0262609 A1* | 10/2008 | Gross et al. | 623/2.36 |
| 2008/0275551 A1 | 11/2008 | Alfieri | |
| 2008/0281411 A1 | 11/2008 | Berreklouw | |
| 2009/0043153 A1 | 2/2009 | Zollinger et al. | |
| 2009/0054969 A1 | 2/2009 | Salahieh et al. | |
| 2009/0099650 A1 | 4/2009 | Bolduc et al. | |
| 2009/0149872 A1 | 6/2009 | Gross et al. | |
| 2009/0177266 A1 | 7/2009 | Powell et al. | |
| 2009/0248148 A1 | 10/2009 | Shaolian | |
| 2009/0259307 A1 | 10/2009 | Gross et al. | |
| 2009/0287231 A1 | 11/2009 | Brooks et al. | |
| 2009/0326648 A1 | 12/2009 | Machold et al. | |
| 2010/0023117 A1 | 1/2010 | Yoganathan | |
| 2010/0094248 A1 | 4/2010 | Nguyen | |
| 2010/0130992 A1 | 5/2010 | Machold et al. | |
| 2010/0152845 A1 | 6/2010 | Bloom | |
| 2010/0161041 A1 | 6/2010 | Maisano et al. | |
| 2010/0161042 A1 | 6/2010 | Maisano et al. | |
| 2010/0161043 A1 | 6/2010 | Maisano et al. | |
| 2010/0161047 A1 | 6/2010 | Cabiri | |
| 2010/0168845 A1 | 7/2010 | Wright | |
| 2010/0211166 A1* | 8/2010 | Miller et al. | 623/2.37 |
| 2010/0249920 A1 | 9/2010 | Bolling | |
| 2010/0280603 A1 | 11/2010 | Maisano et al. | |
| 2010/0280604 A1 | 11/2010 | Zipory et al. | |
| 2010/0280605 A1 | 11/2010 | Hammer et al. | |
| 2010/0286767 A1 | 11/2010 | Zipory et al. | |
| 2011/0082538 A1 | 4/2011 | Dahlgren | |
| 2011/0106245 A1 | 5/2011 | Miller et al. | |
| 2011/0106247 A1 | 5/2011 | Miller et al. | |
| 2011/0166649 A1 | 7/2011 | Gross et al. | |
| 2011/0190879 A1 | 8/2011 | Bobo et al. | |
| 2011/0208283 A1 | 8/2011 | Rust | |
| 2011/0238088 A1 | 9/2011 | Bolduc | |
| 2011/0282361 A1 | 11/2011 | Miller | |
| 2012/0078355 A1 | 3/2012 | Zipory | |
| 2012/0123531 A1 | 5/2012 | Tsukashima | |
| 2012/0136436 A1 | 5/2012 | Cabiri | |
| 2012/0330410 A1 | 12/2012 | Hammer | |
| 2013/0116780 A1 | 5/2013 | Miller | |

FOREIGN PATENT DOCUMENTS

| | | |
|---|---|---|
| WO | WO 02/085252 A1 | 10/2002 |
| WO | WO 2006/097931 A2 | 9/2006 |
| WO | WO 2006/116558 A2 | 11/2006 |
| WO | WO 2007/136783 A2 | 11/2007 |
| WO | WO 2008/068756 A2 | 6/2008 |
| WO | WO 2010/004546 A1 | 1/2010 |
| WO | WO 2010/073246 A3 | 7/2010 |
| WO | WO 2010/128502 A1 | 11/2010 |
| WO | WO 2010/128503 A2 | 11/2010 |
| WO | WO 2011/051942 A1 | 5/2011 |
| WO | WO 2011/067770 A1 | 6/2011 |

OTHER PUBLICATIONS

Amplatzer ® Septal Occluder. A patient guide to the Non-Surgical Closure of the Atrial Septal Defect Using the AMPLATZER Septal Occluder System, AGA Medical Corporation, Apr. 2008.

Dieter, "Percutaneous valve repair: Update on mitral regurgitation and endovascular approaches to the mitral valve," App. in Imaging, Cardiac Interventions, Supported by an edu grant from Amersham Health pp. 11-14 (2003).

International Search Report and a Written Opinion dated Jun. 10, 2010, issued in PCT/IL09/01209.

International Search Report and a Written Opinion, both dated Aug. 17, 2010, issued in PCT/IL10/00357.

International Search Report and a Written Opinion, both dated Nov. 8, 2010, issued in PCT/IL10/00358.

Internaitonal Search Report dated Sep. 8, 2009, issued in PCT/IL09/00593.

Maisano et al., "The double-orifice technique as a standard approach to treat mitral regurigitation due to severe myxomatous disease: surgical technique," European Journal of Cardio-thoracic Surgery 17 (2000) 201-205.

Odell et al., "Early Results of a Simplified Method of Mitral Valve Annuloplasty," Circulation 92:150-154 (1995).

Office Action dated Apr. 6, 2010, issued in U.S. Appl. No. 12/484,512.

Office Action dated Aug. 4, 2010, issued in U.S. Appl. No. 12/341,960.

Office Action dated Oct. 6, 2010, issued in U.S. Appl. No. 12/484,512.

O'Reilly et al., "Heart valve surgery pushes the envelope," Medtech Insight 8(3): 73, 99-108 (2006).

Supplementary European Search Report dated Feb. 1, 2011, issued in European Patent Application No. 07849540.

Swain et al., "An endoscopically deliverable tissue-transfixing device for securing biosensors in gastrointestinal tract," Gastrointestinal Endoscopy 40(6): 730-734 (1994).

Tajik et al. "Two-Dimensional Real-Time Ultrasonic Imaging of the Heart and Great Vessels," Mayo Clinic Proceedings, vol. 53: 271-303, 1978.

U.S. Appl. No. 60/873,075, filed Dec. 5, 2006.
U.S. Appl. No. 60/902,146, filed Feb. 16, 2007.
U.S. Appl. No. 61/001,013, filed Oct. 29, 2007.
U.S. Appl. No. 61/132,295, filed Jun. 16, 2008.
U.S. Appl. No. 61/207,908, filed Feb. 17, 2009.
U.S. Appl. No. 61/265,936, filed Dec. 2, 2009.

An Office Action dated Jun. 13, 2012, which issued during the prosecution of U.S. Appl. No. 12/437,103.

An Office Action dated Jul. 20, 2012, which issued during the prosecution of U.S. Appl. No. 12/843,412.

An Office Action dated Jun. 7, 2013, which issued during the prosecution of U.S. Appl. No. 13/141,606.

An Office Action dated Aug. 23, 2013, which issued during the prosecution of U.S. Appl. No. 13/167,444.

An International Search Report and a Written Opinion both dated Feb. 22, 2013, which issued during the prosecution of Applicant's PCT/IL2012/050451.

Supplementary European Search Report dated Mar. 28, 2013, which issued during the prosecution of EP Patent Application No. 10772091.

An Office Action dated May 6, 2013, which issued during the prosecution of U.S. Appl. No. 12/689,693.

An Office Action dated Apr. 1, 2013, which issued during the prosecution of U.S. Appl. No. 13/167,476.

An International Search Report and a Written Opinion both dated Dec. 6, 2012, which issued during the prosecution of Applicant's PCT/IL2012/000250.

An Office Action dated Nov. 30, 2012, which issued during the prosecution of U.S. Appl. No. 12/689,635.

Supplementary European Search Report dated Dec. 4, 2012, which issued during the prosecution of European Patent Application No. 09834225.

An Office Action dated Jan. 17, 2013, which issued during the prosecution of U.S. Appl. No. 13/167,444.

An Office Action issued in U.S. Appl. No. 13/666,262 dated Dec. 16, 2013.

An Office Action issued in U.S. Appl. No. 13/167,476 dated Nov. 21, 2013.

An Office Action issued in U.S. Appl. No. 13/666,141 dated Dec. 18, 2013.

An Office Action issued in U.S. Appl. No. 14/027,934 dated Dec. 19, 2013.

Office Action, dated Feb. 3, 2014, issued by the United States Patent and Trademark Office, in counterpart U.S. Appl. No. 12/689,693.

International Search Report and Written Opinion, dated Apr. 9, 2014, issued by the International Search Authority, in counterpart Application No. PCT/IL13/50860.

(56) References Cited

OTHER PUBLICATIONS

Communication dated Jul. 25, 2014, issued by the State Intellectual Property Office of the P.R. of China, in counterpart Application No. 200980157331.3.

Communication dated Aug. 22, 2014, issued by the United States Patent and Trademark Office in counterpart Application No. 14027934.

Communication dated Aug. 26, 2014, issued by the United States Patent and Trademark Office in counterpart Application No. 13167444.

An Office Action dated Jun. 2, 2014, which issued during the prosecution of U.S. Appl. No. 13/319,030.

An Office Action dated Jun. 4, 2014, which issued during the prosecution of U.S. Appl. No. 12/840,463.

An English translation of an Office Action dated Apr. 23, 2014 which issued during the prosecution of Chinese Patent Application No. 201080059948.4.

An Office Action dated Jun. 11, 2014, which issued during the prosecution of U.S. Appl. No. 14/027,934.

Notice of Allowance dated Jun. 11, 2014, which issued during the prosecution of U.S. Appl. No. 12/689,693.

Notice of Allowance dated Jun. 25, 2014, which issued during the prosecution of U.S. Appl. No. 13/666,262.

\* cited by examiner

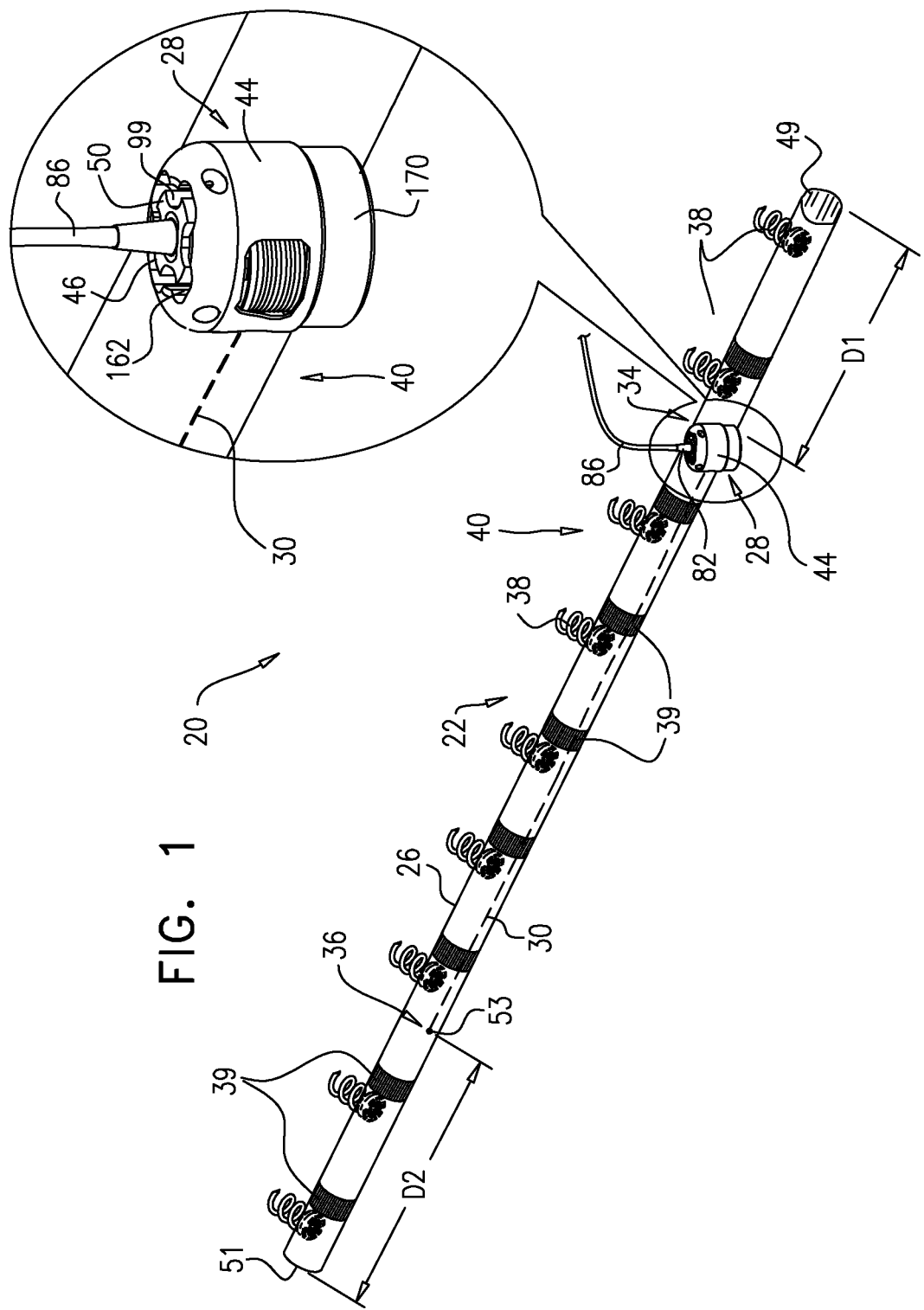

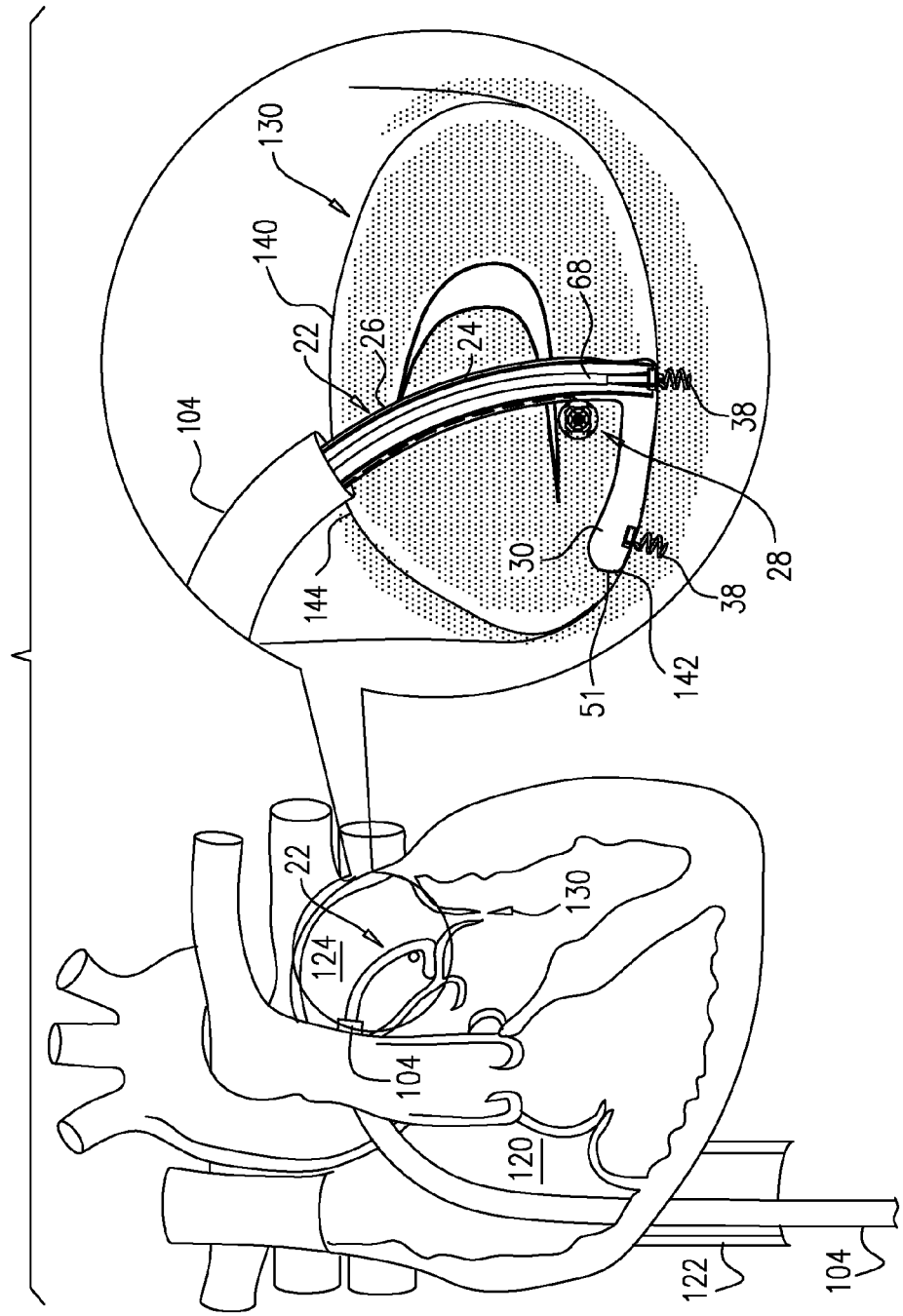

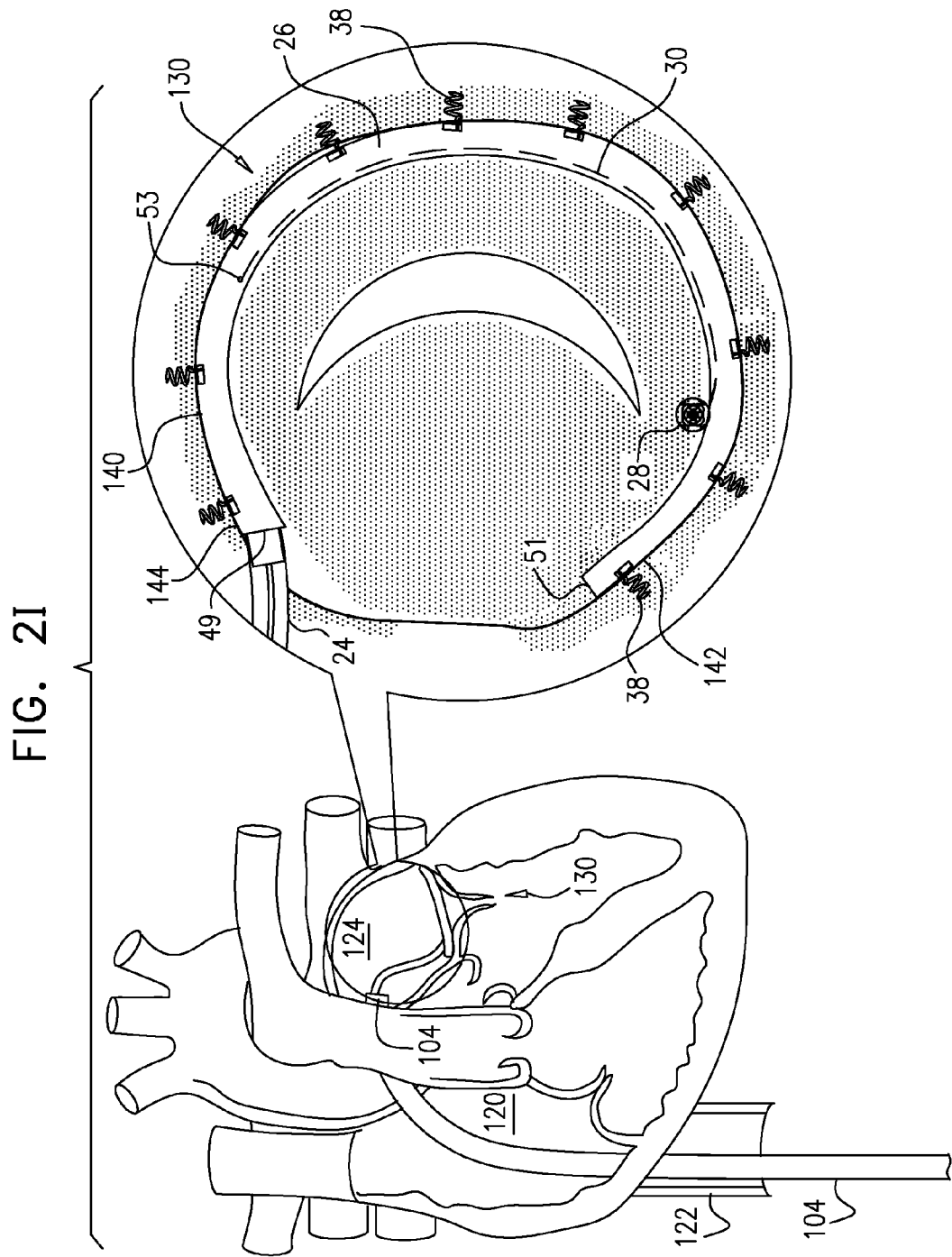

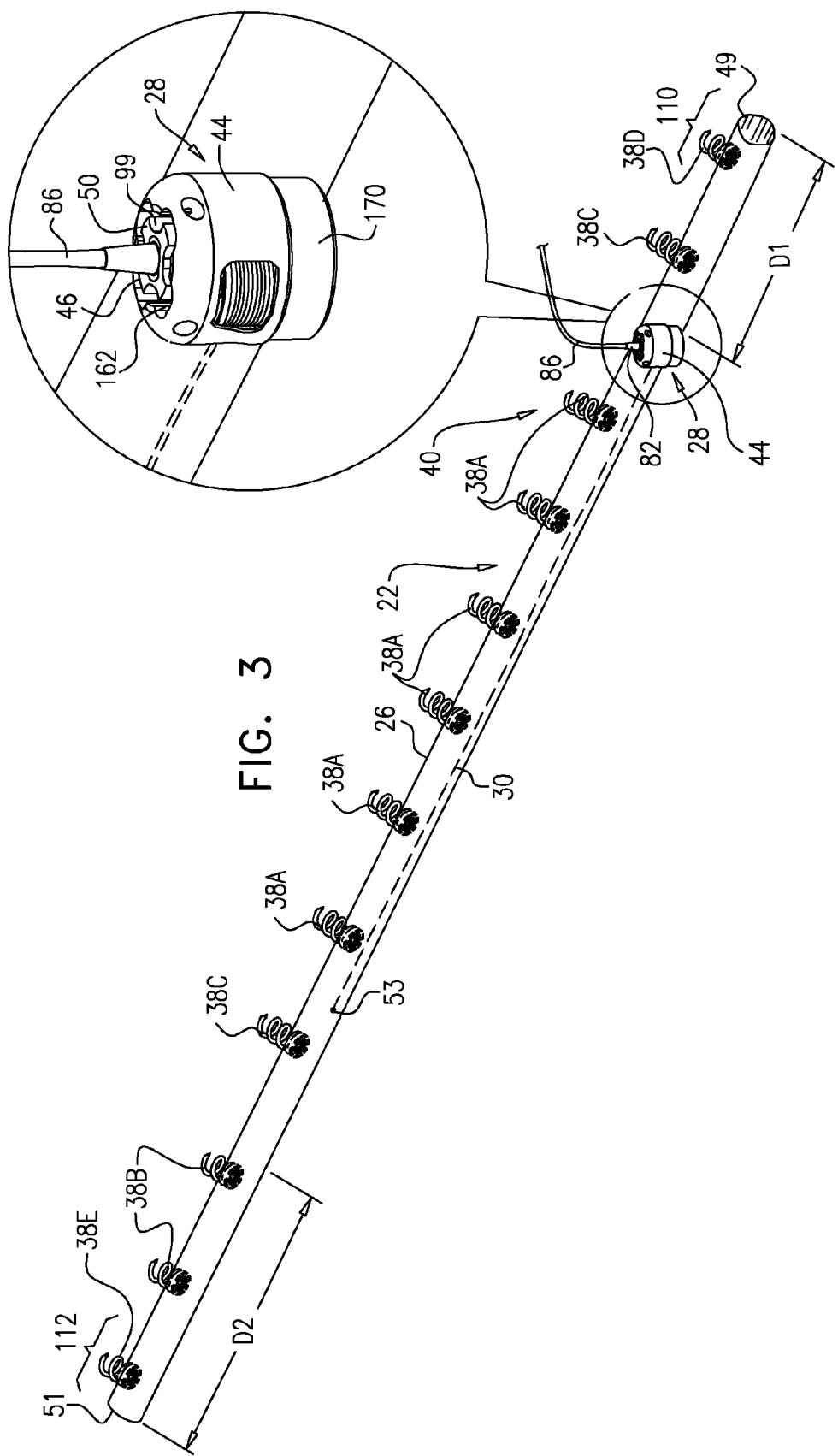

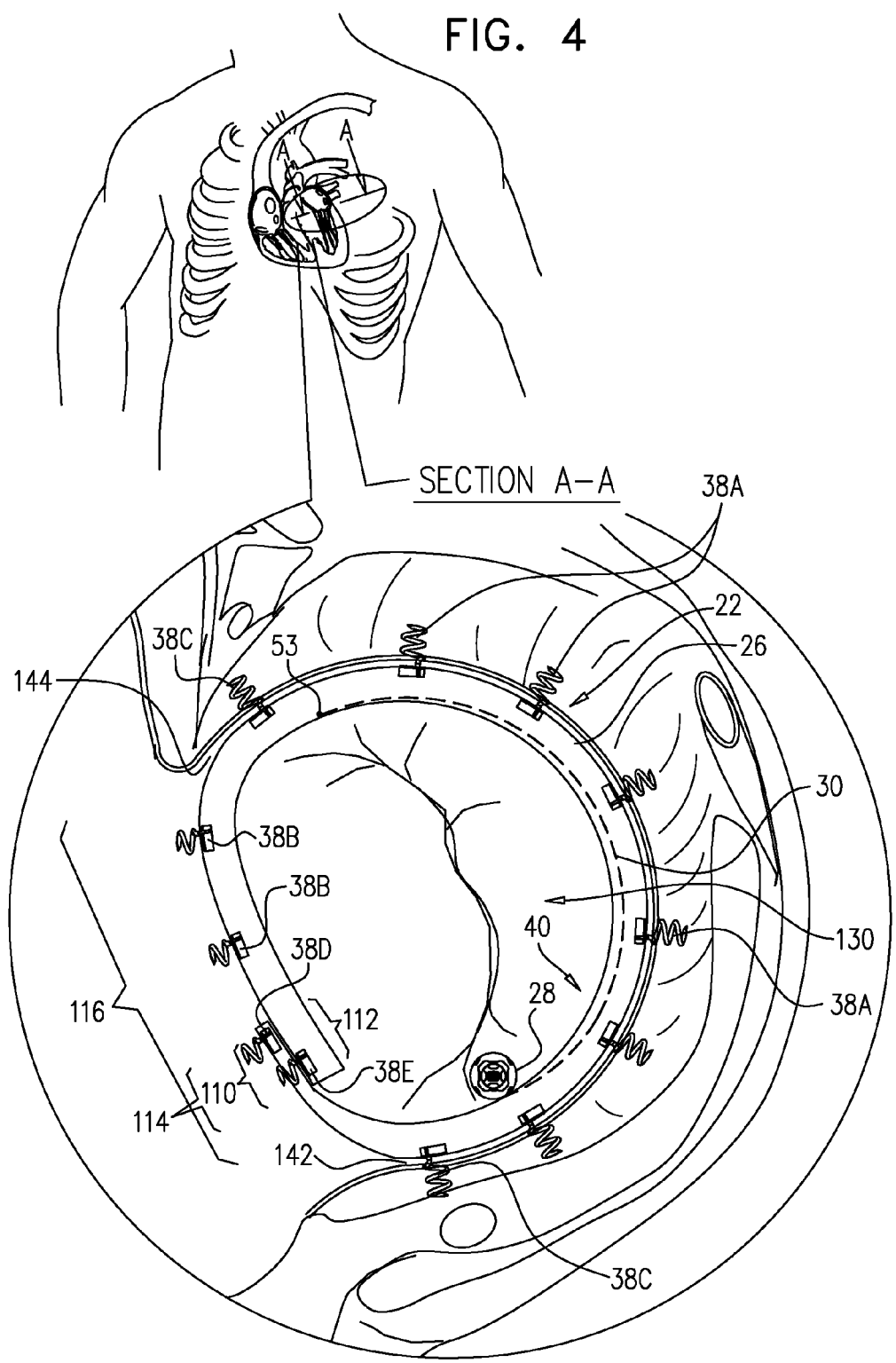

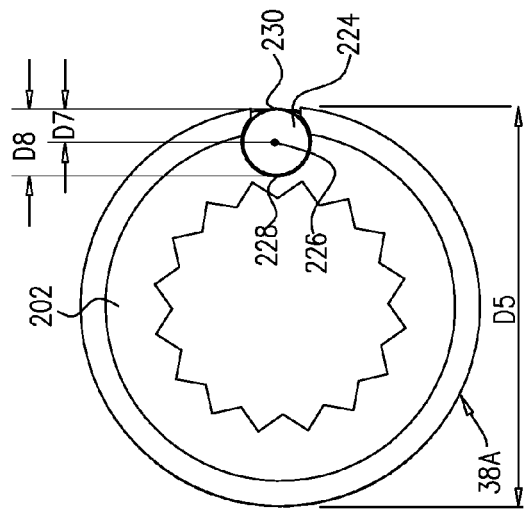
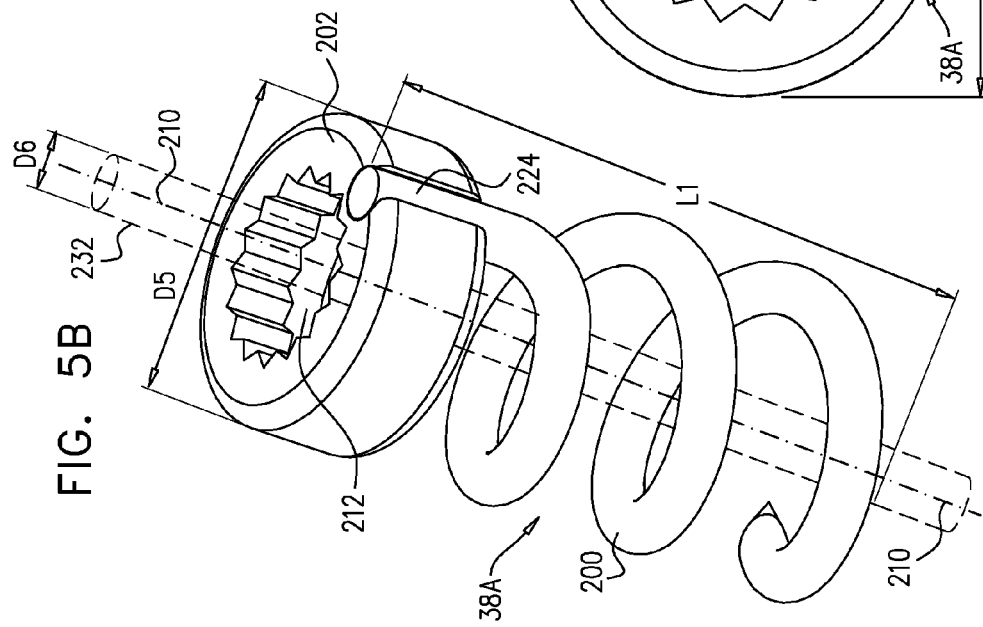
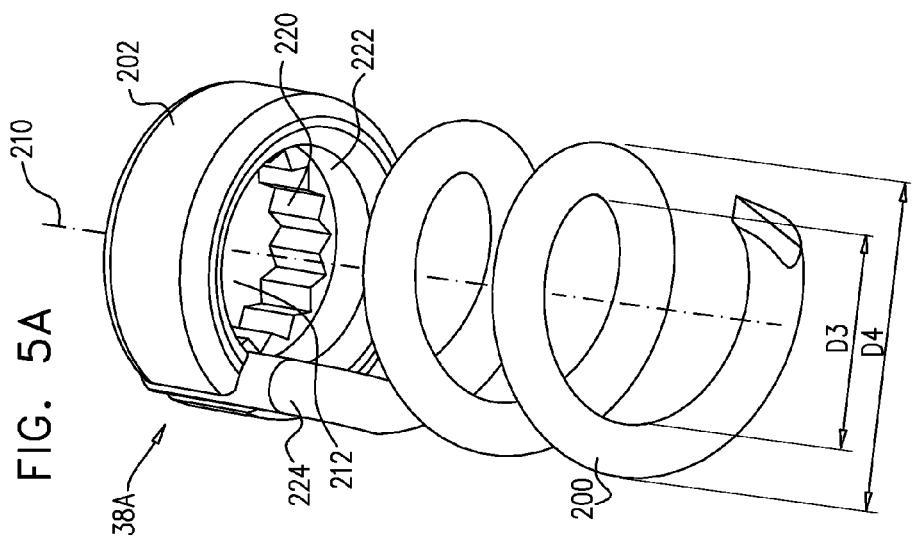

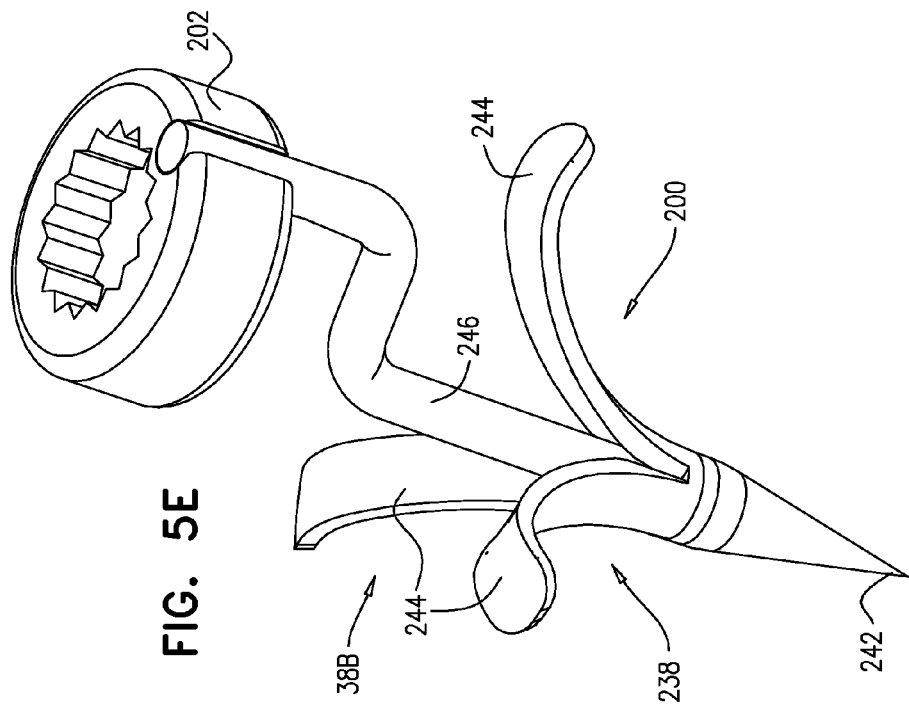
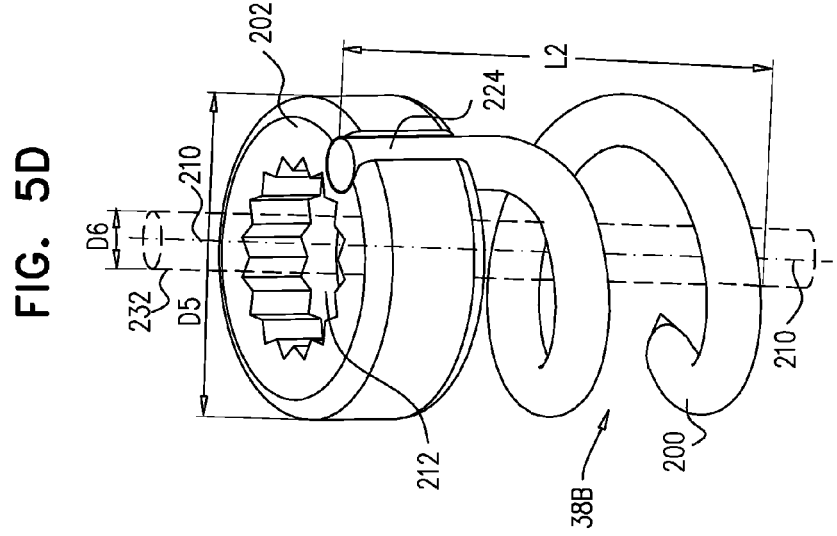

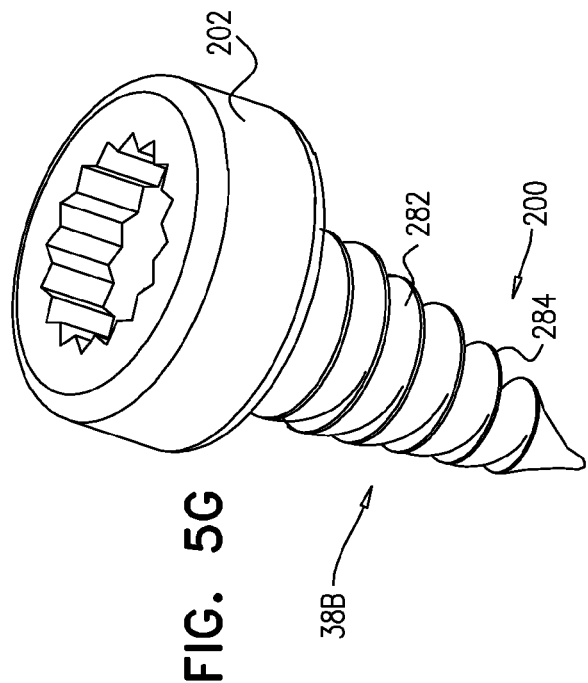
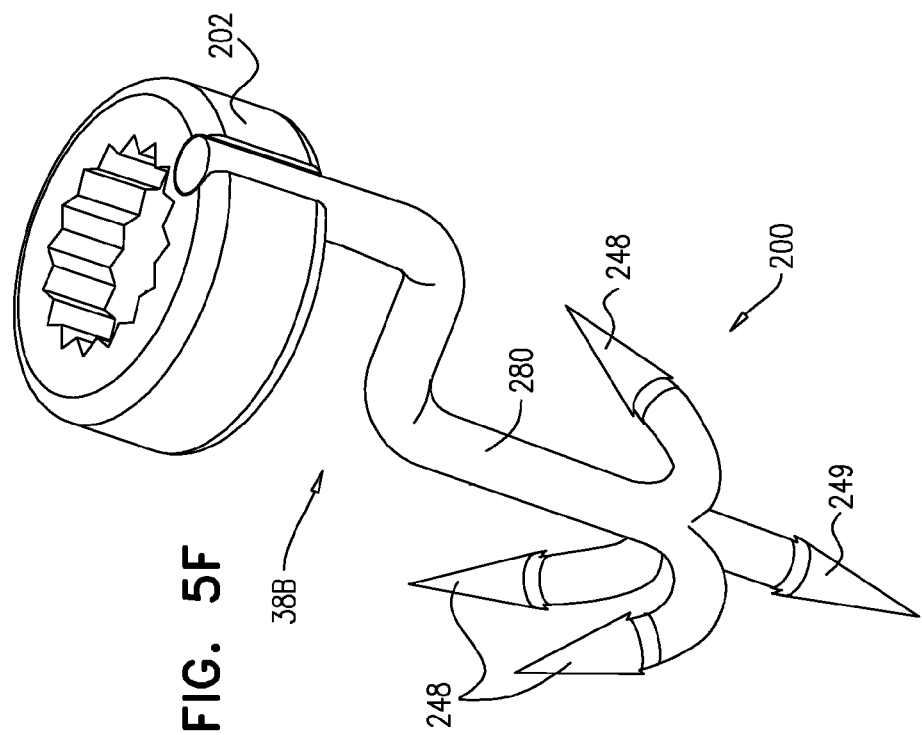

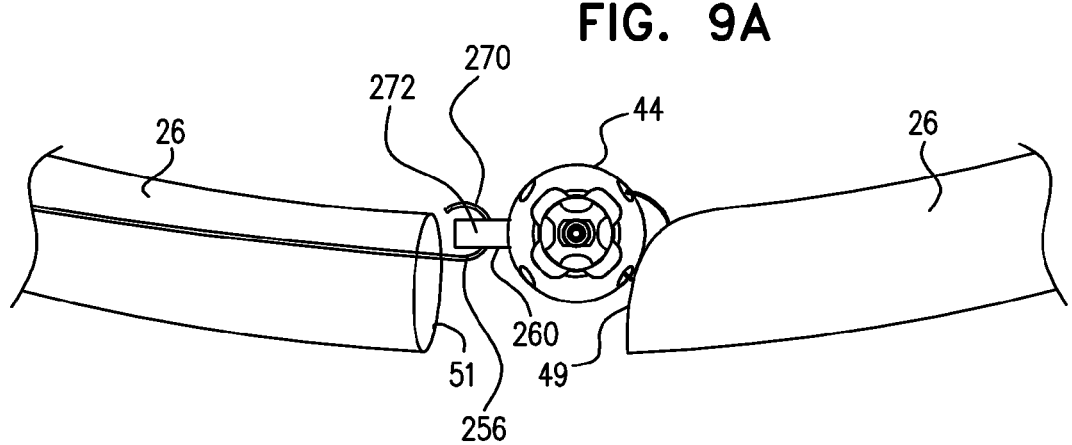
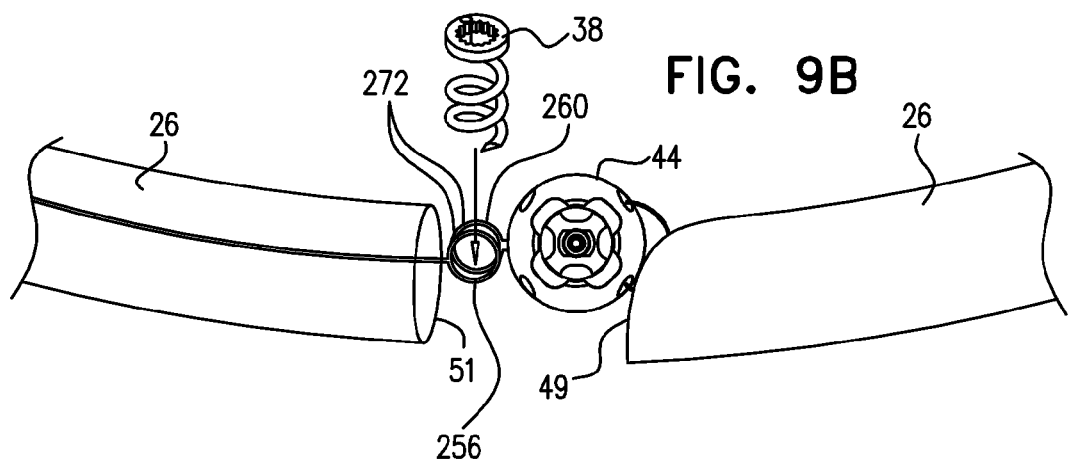

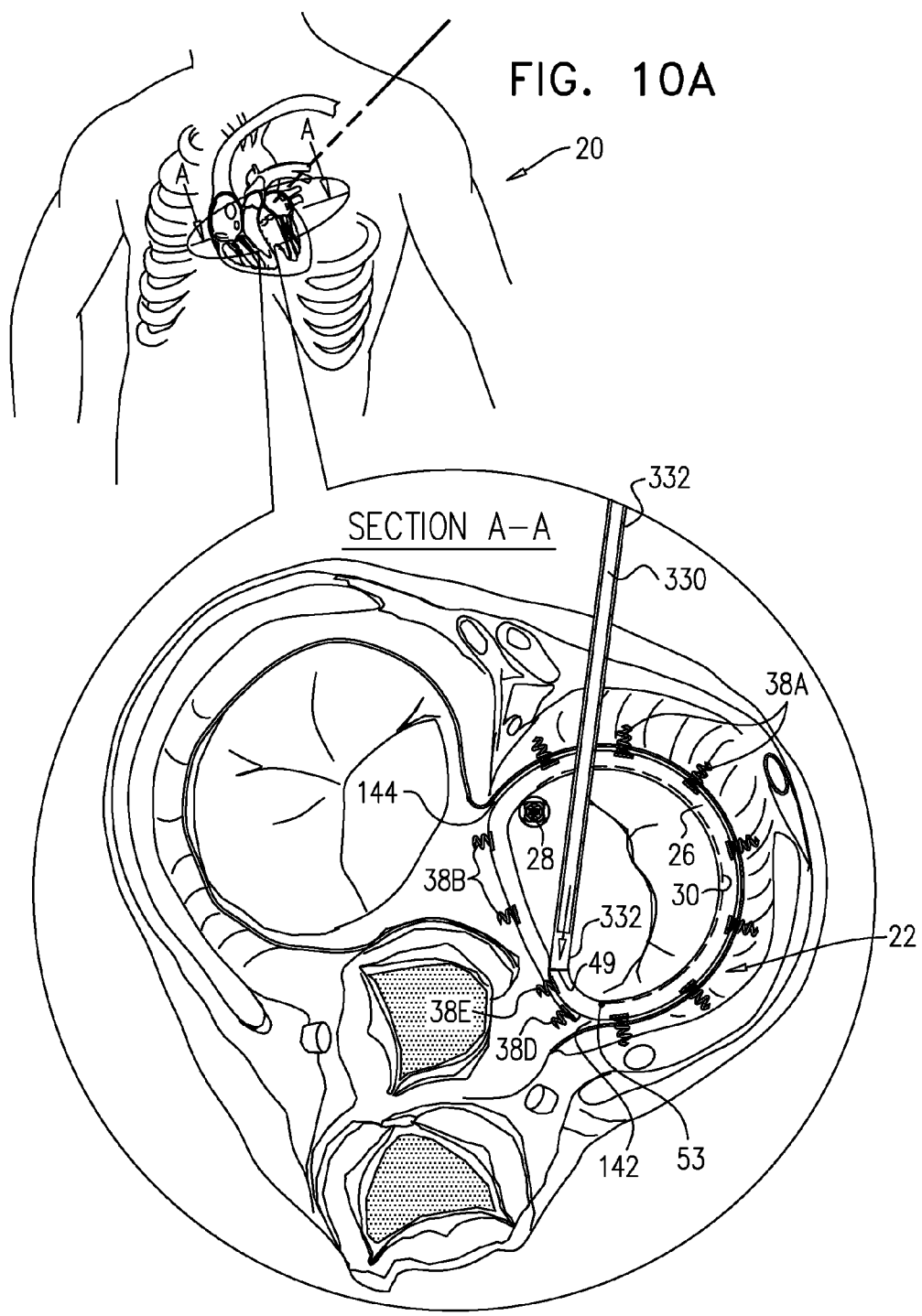

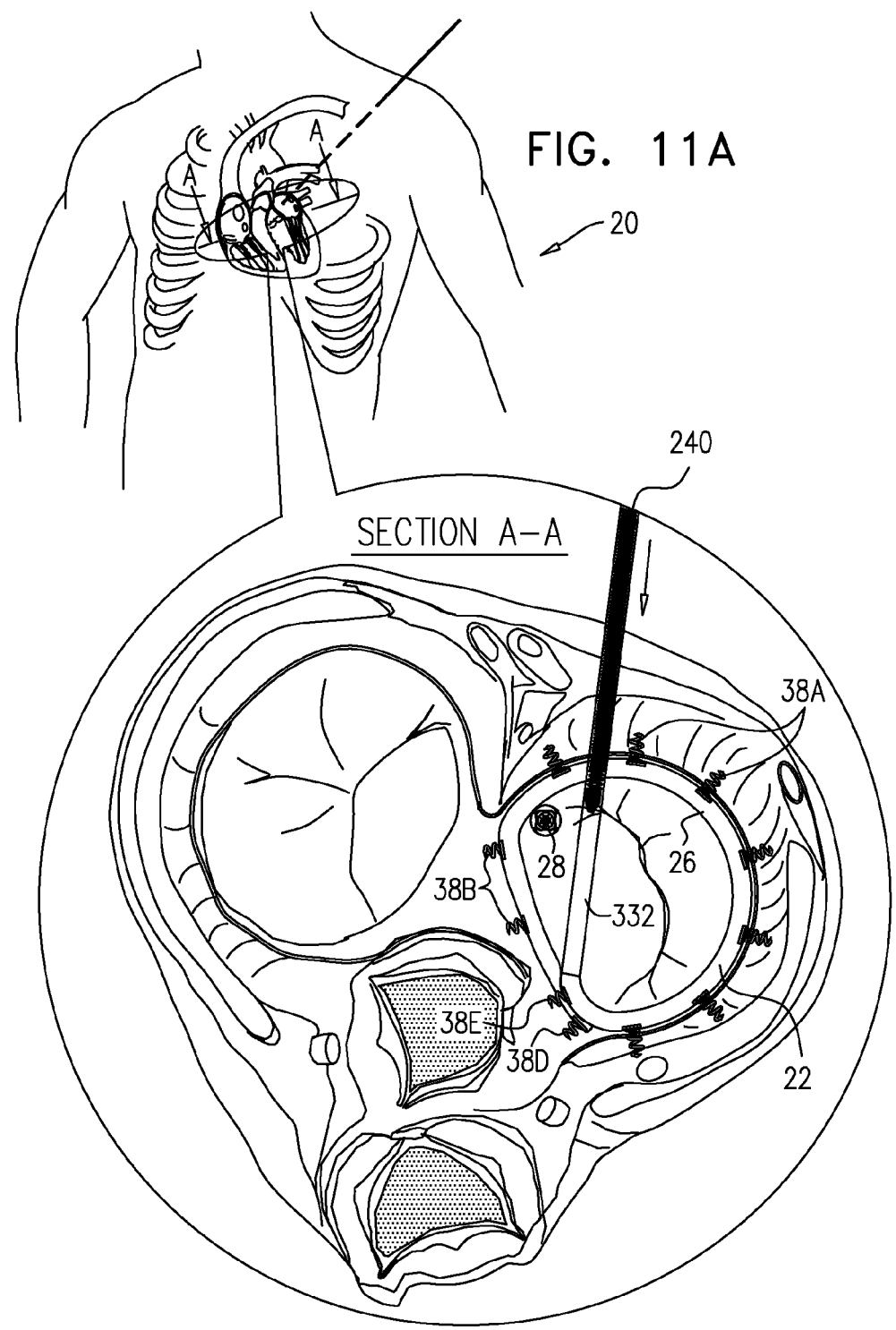

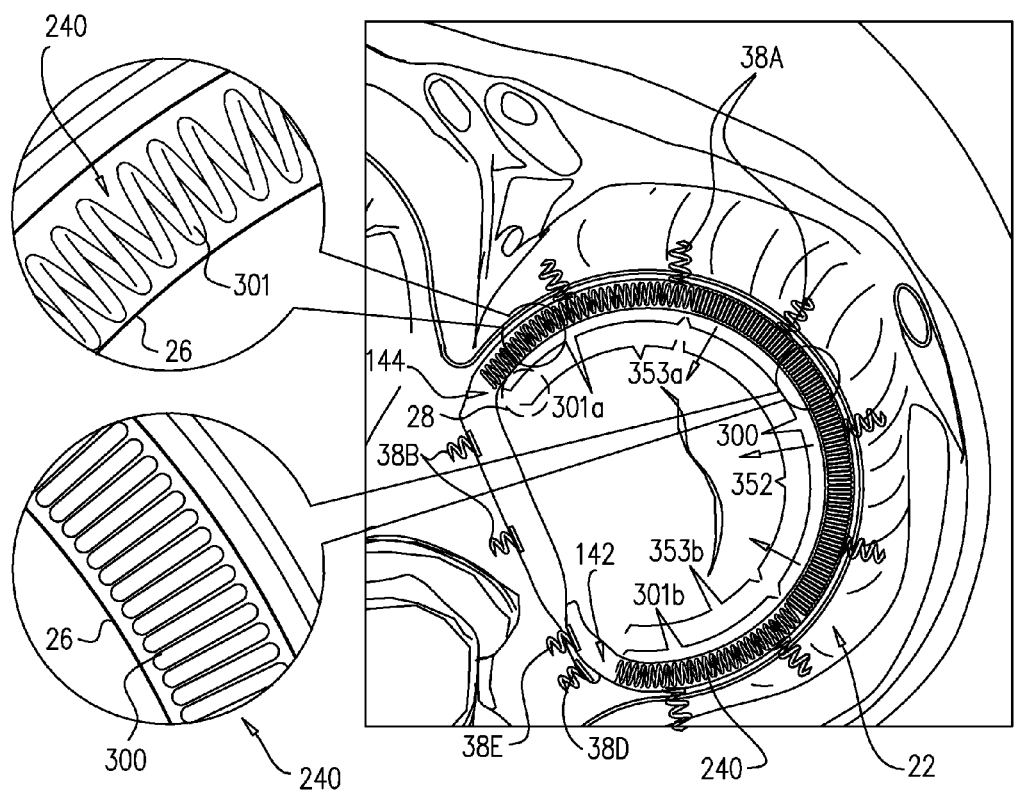

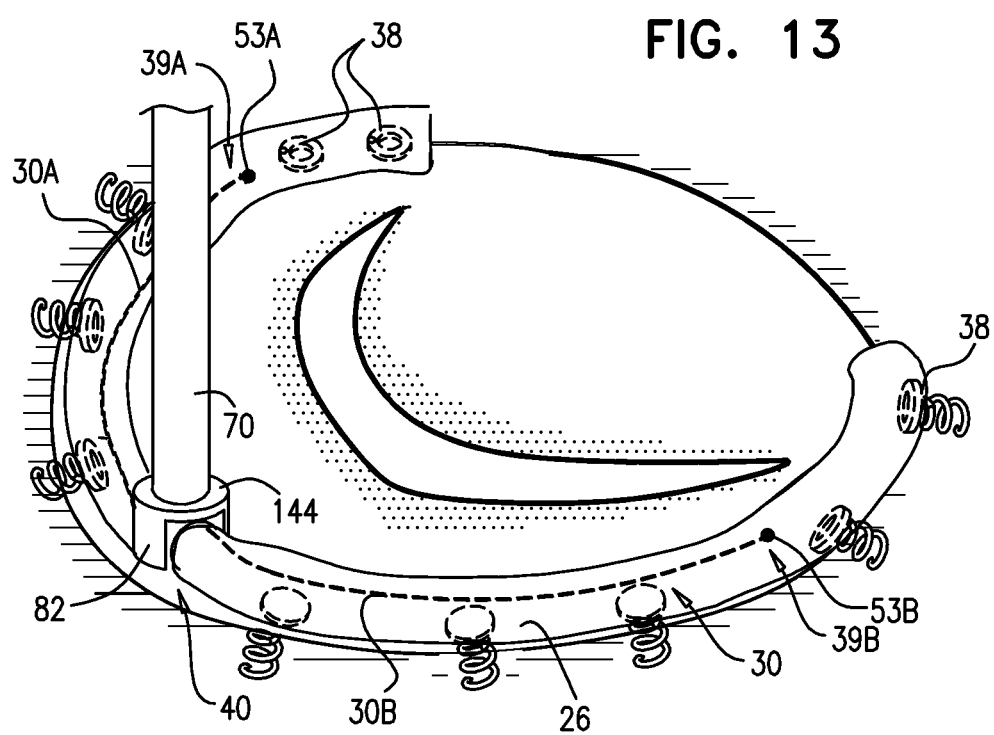

CLOSED BAND FOR PERCUTANEOUS ANNULOPLASTY

FIELD OF THE APPLICATION

Some applications of the present invention relate in general to valve repair, and more specifically to repair of an atrioventricular valve of a patient.

BACKGROUND OF THE APPLICATION

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium. Dilation of the annulus is sometimes treated by annuloplasty, in which a partial or full ring is implanted around the annulus to cause the leaflets to coapt when the valve is closed.

SUMMARY

In some applications of the present invention, an implantable structure is provided that comprises a flexible sleeve having first and second sleeve ends, a contracting assembly, and a plurality of tissue anchors. The contracting assembly is configured to longitudinally contract the sleeve, and comprises a contracting mechanism and a longitudinal contracting member having first and second member ends. The contracting mechanism is disposed longitudinally at a first site of the sleeve, and the second member end is coupled to the sleeve longitudinally at a second site longitudinally between the first site and the second sleeve end, exclusive. The contracting member also has a first member end portion, which extends from the first member end toward the second member end along only a longitudinal portion of the contracting member, and is coupled to the contracting mechanism. A first portion of the sleeve longitudinally extends from the first sleeve end toward the first site, and a second portion of the sleeve longitudinally extends from the second sleeve end toward the second site. The sleeve is arranged in a closed loop, such that the first and second portions of the sleeve together define a longitudinally overlapping portion of the sleeve. The implantable structure is configured such that the contracting assembly applies a longitudinal contracting force only between the first and the second sites, and not along the overlapping portion. The longitudinal contracting force longitudinally contracts at least a portion of the sleeve only between the first and the second sites, and not along the overlapping portion. Typically, the contracting member extends along neither the first nor the second portion of the sleeve.

In some applications of the present invention, the contracting assembly includes one or more longitudinal contracting members coupled to the contracting mechanism. The implantable structure is placed completely around an annulus of an atrioventricular valve of a subject, such that none of the one or more longitudinal contracting members is positioned along an anterior portion of the annulus between fibrous trigones of the valve. The implantable structure is fastened to the annulus. The contracting assembly is then actuated to contract a longitudinal portion of the sleeve not positioned along the anterior portion of the annulus. Tightening of the implantable structure therefore tightens at least a portion of the posterior portion of the annulus, while preserving the length of the anterior portion of the annulus. (The anterior portion of the annulus should generally not be contracted because its tissue is part of the skeleton of the heart). However, the portion of the sleeve deployed along the anterior portion of the annulus prevents dilation of the anterior annulus, because the sleeve is anchored at both ends of the anterior annulus, and the sleeve typically comprises a longitudinally non-extensible material. This deployment configuration may help prevent long-term resizing of annulus, especially the anterior annulus, which sometimes occurs after implantation of partial annuloplasty rings, such as C-bands.

In some applications of the present invention, one or more of the tissue anchors are coupled to the sleeve at respective third sites longitudinally between the second site and the second sleeve end, exclusive. Typically, the implantable structure is configured such that the contracting assembly applies a longitudinal contracting force only between the first and the second sites. The longitudinal contracting force contracts at least a portion of the sleeve only between the first and the second sites. Providing the one or more anchors beyond the ends of the contracting member generally distributes force applied by contraction of the contracting assembly over the tissue interfaces of these anchors. In contrast, in some configurations of the implantable structure in which anchors are not provided beyond the ends of the contracting member, the force applied by the contracting assembly is applied predominantly to the single anchor nearest the first end of the contracting member, and the single anchor nearest the second end of the contracting member.

For some applications, at least two of the tissue anchors are coupled to the sleeve at respective third sites longitudinally between the second member end and the second sleeve end, exclusive. For some applications, the second site is at least 5 mm from the second sleeve end, measured when the sleeve is in a straight, relaxed, non-contracted state, such as at least 9 mm, e.g., at least 18 mm. For some applications, the second site is at a longitudinal distance from the second sleeve end, which distance is no greater than 30% of a total length of the sleeve, the distance and length measured when the sleeve is in the straight, relaxed, non-contracted state. For some applications, at least three of the tissue anchors are coupled to the sleeve alongside the contracting member, longitudinally between the first and second sites, exclusive. Typically, the sleeve is substantially longitudinally non-extensible.

For some applications, the sleeve has first and second sleeve ends, and first and second portions that longitudinally extend from the first and the second sleeve ends, respectively. The sleeve is arranged in a closed loop, such that the first and second portions of the sleeve together define a longitudinally overlapping portion of the sleeve positioned at least partially along the anterior portion of the annulus, and none of the one or more longitudinal contracting members is positioned along the overlapping portion of the sleeve. For some applications, at least one of the tissue anchors penetrates both the first and second portions of the sleeve at the overlapping portion. Such a mutual anchor helps ensure that the first and second portions remain tightly coupled together and to the tissue, so that the sleeve retains its closed loop shape. Alternatively, for some applications, the sleeve is shaped so as to define an integrally closed loop having no sleeve ends.

The implantable structure, when in this closed-loop configuration, is deployed around the entire annulus of the native valve, including an anterior portion of the annulus (on the aortic side of the valve) between the fibrous trigones. Typically, the contracting member does not extend along the portion of the sleeve deployed along the anterior portion of the annulus, and thus does not extend along the first portion, the second portion, or the overlapping portion of the sleeve. The portion of the sleeve deployed along the anterior portion of the annulus (between the trigones) is thus non-contractible. As mentioned above, tightening of the implantable structure therefore tightens the posterior portion of the annulus, while preserving the length of the anterior portion of the annulus. For some applications, this deployment configuration may also help achieve a closed loop that serves as a base ring to which a prosthetic valve is coupled.

In some applications of the present invention, the anchors deployed along the anterior portion of the annulus are of a different configuration from the anchors deployed along the remainder of the annulus. Unlike the remainder of the annulus, the anterior portion does not comprise muscular or fibrous tissue, but rather thinner aortic tissue (typically the anchors positioned along the anterior portion enter the aorta below the aortic leaflets). The anchors that are deployed along the remainder of the annulus are configured for strong coupling to the thicker and stronger fibrous tissue of these portions of the annulus. Such anchors may be inappropriate for coupling to the anterior portion. Anchors are thus provided that are particularly configured for coupling to the anterior portion.

For some applications, the configurations differ in size. For example, the configuration may differ in the lengths of respective tissue coupling elements of the anchors. The lengths of the tissue coupling elements of the anchors deployed along the remainder (non-anterior) portion of the annulus are greater than the lengths of the tissue coupling elements of the anchors deployed along the anterior portion of the annuls. Alternatively or additionally, for some applications, the anchors deployed along the remainder (non-anterior) portion of the annulus comprise a harpoon anchor, a screw anchor, a septal occlude anchor, a barbed anchor, or sutures.

In some applications of the present invention, the implantable structure further comprises an elongated linking member, which is positioned along an anterior portion of the annulus, so as to join the ends of the implantable structure in a complete loop. Over time after implantation, the linking member becomes fixed to the anterior portion of the annulus, thereby helping prevent long-term dilation of the anterior annulus. Typically, at least a portion of the linking member is disposed within and covered by the sleeve, into and/or over which fibrous tissue grows over time, helping anchor the linking member to tissue of the anterior annulus. Typically, in this configuration of the implantable structure, none of the anchors is coupled to the anterior portion of the annulus.

A first end of the linking member is typically fixed between 2 and 6 cm from a first end of the sleeve. A second end of the linking member is positioned within 1.5 cm of the same end of the sleeve, either protruding from the end of the sleeve, or recessed within the sleeve. The second end of the linking member comprises (e.g., is shaped so as to define) a first coupling element. The implantable structure further comprises a second coupling element, which is configured to be coupleable to the first coupling element. The second coupling element is coupled to the implantable structure within 1.5 cm of the second end of the sleeve. The second coupling element may be coupled to the housing, directly to the sleeve, or otherwise coupled to the implantable structure. Typically, the linking member is substantially longitudinally non-extensible, i.e., its length is fixed.

For some applications, the linking member is configured as a spring, which is typically curved, so as to be elastic in a radial direction, i.e., to be compressible like a bow or deflected beam. In these applications, the linking member is oriented such that it is pressed by elasticity against the anterior portion of the mitral annulus, i.e., the outer wall of the aorta, thereby holding the sleeve covering the linking member against the aortic wall. For some applications, at least two of the tissue anchors are coupled to the sleeve at respective, different longitudinal sites alongside the linking member, within 6 cm of the first end of the linking member. These tissue anchors may help set the proper direction of curvature of the linking member, for applications in which the linking member is curved.

For some applications, the contracting mechanism comprises a rotatable structure, and a housing in which the rotatable structure is positioned. The contracting mechanism and the longitudinal contracting member are arranged such that rotation of the rotatable structure contracts the implant structure. Typically, an anchor deployment manipulator is advanced into a lumen of the sleeve, and, from within the lumen, deploys the anchors through a wall of the sleeve and into cardiac tissue, thereby anchoring the sleeve around a portion of a valve annulus.

For some applications, the implantable structure comprises an adjustable annuloplasty ring for repairing a dilated valve annulus of an atrioventricular valve, such as a mitral valve. The annuloplasty ring may be used for treating functional mitral regurgitation (FMR) or degenerative mitral valve disease. For other applications, a prosthetic heart valve is further provided, which is configured to be coupled to the sleeve.

For some applications in which the implantable structure is implanted around the annulus of a valve, the implantable structure may be advanced toward the annulus of a valve in any suitable procedure, e.g., a transcatheter procedure, a percutaneous procedure, a minimally invasive procedure, or an open heart procedure.

There is therefore provided, in accordance with an application of the present invention, apparatus including an implantable structure, which includes:

a flexible sleeve, having first and second sleeve ends; and a contracting assembly, which is configured to longitudinally contract the sleeve, and which includes:

a contracting mechanism, which is disposed longitudinally at a first site of the sleeve; and a longitudinal contracting member, having (a) a first member end, (b) a second member end, which is coupled to the sleeve longitudinally at a second site longitudinally between the first site and the second sleeve end, exclusive, and (c) a first member end portion, which (i) extends from the first member end toward the second member end along only a longitudinal portion of the contracting member, and (ii) is coupled to the contracting mechanism, wherein a first portion of the sleeve longitudinally extends from the first sleeve end toward the first site, and a second portion of the sleeve longitudinally extends from the second sleeve end toward the second site, wherein the sleeve is arranged in a closed loop, such that the first and second portions of the sleeve together define a longitudinally overlapping portion of the sleeve, and wherein the implantable structure is configured such that the contracting assembly applies a longitudinal contracting force only between the first and the second sites, and not along the overlapping portion.

For some applications, the implantable structure further includes a plurality of tissue anchors, at least one of which penetrates both the first and second portions of the sleeve at the overlapping portion. For some applications, the at least one of the tissue anchors includes a coupling head and a tissue coupling element, the tissue coupling element penetrates both the first and second portions of the sleeve at the overlapping portion, and the coupling head is positioned within one of the first and second portions of the sleeve at the overlapping portion. For some applications, the plurality of tissue anchors includes: (a) a plurality of first tissue anchors of a first configuration, coupled to the sleeve at intervals along a first longitudinally-contiguous portion of the loop; and (b) a plurality of second tissue anchors of a second configuration different from the first configuration, coupled to the sleeve at intervals along a second longitudinally-contiguous portion of the loop different from the first longitudinally-contiguous portion, which second longitudinally contiguous portion includes the longitudinally overlapping portion. The first and second tissue anchors are optionally configured as described below.

For some applications, the overlapping portion has a length of between 5 and 60 mm.

For some applications, the contracting member does not extend along the first portion of the sleeve, and does not extend along the second portion of the sleeve.

For some applications, the first site is a first longitudinal distance from the first sleeve end; the second site is at a second longitudinal distance from the second sleeve end, which first and second longitudinal distances are measured when the sleeve is in a straight, relaxed, non-contracted state; and at least one of the first and second longitudinal distances, taken separately, is at least 18 mm.

For any of the applications described above, the contracting mechanism may include a housing and a rotatable structure positioned within the housing, which housing is disposed at the first site of the sleeve, and the rotatable structure and the longitudinal contracting member may be arranged such that rotation of the rotatable structure longitudinally contracts the sleeve.

For any of the applications described above, at least three of the tissue anchors may be coupled to the sleeve alongside the contracting member, longitudinally between the first and second sites, exclusive.

For any of the applications described above, the sleeve may be substantially longitudinally non-extensible.

There is further provided, in accordance with an application of the present invention, apparatus including an implantable structure, which includes:
 a flexible sleeve, having first and second sleeve ends;
 a contracting assembly, which is configured to longitudinally contract the sleeve, and which includes:
  a contracting mechanism, which is disposed longitudinally at a first site of the sleeve; and
  a longitudinal contracting member, having (a) a first member end, (b) a second member end, which is coupled to the sleeve longitudinally at a second site, which is longitudinally between the first site and the second sleeve end, exclusive, and (c) a first member end portion, which (i) extends from the first member end toward the second member end along only a longitudinal portion of the contracting member, and (ii) is coupled to the contracting mechanism; and
 a plurality of tissue anchors, one or more of which are coupled to the sleeve at respective third sites longitudinally between the second site and the second sleeve end, exclusive.

For some applications, at least two of the tissue anchors are coupled to the sleeve at respective third sites longitudinally between the second member end and the second sleeve end, exclusive.

For some applications, the second site is at least 5 mm from the second sleeve end, such as at least 9 mm, e.g., at least 18 mm, measured when the sleeve is in a straight, relaxed, non-contracted state.

For some applications, the second site is at a longitudinal distance from the second sleeve end, which distance is no greater than 30% of a total length of the sleeve, the distance and length measured when the sleeve is in the straight, relaxed, non-contracted state.

For some applications, a first portion of the sleeve longitudinally extends from the first sleeve end toward the first site, a second portion of the sleeve longitudinally extends from the second sleeve end toward the second site, and the sleeve is arranged in a closed loop, such that the first and second portions of the sleeve together define a longitudinally overlapping portion of the sleeve. For some applications, at least one of the tissue anchors penetrates both the first and second portions of the sleeve at the overlapping portion. For some applications, the at least one of the tissue anchors includes a coupling head and a tissue coupling element, the tissue coupling element penetrates both the first and second portions of the sleeve at the overlapping portion, and the coupling head is positioned within one of the first and second portions of the sleeve at the overlapping portion.

For some applications, the overlapping portion has a length of between 5 and 60 mm. For some applications, the contracting member does not extend along the first portion of the sleeve, and does not extend along the second portion of the sleeve.

For any of the applications described above, the contracting mechanism may include a housing and a rotatable structure positioned within the housing, which housing is disposed at the first site of the sleeve, and the rotatable structure and the longitudinal contracting member may be arranged such that rotation of the rotatable structure longitudinally contracts the sleeve.

For any of the applications described above, at least three of the tissue anchors may be coupled to the sleeve alongside the contracting member, longitudinally between the first and second sites, exclusive.

For any of the applications described above, the implantable structure may be configured such that the contracting assembly applies a longitudinal contracting force only between the first and the second sites.

For any of the applications described above, the sleeve may be substantially longitudinally non-extensible.

There is still further provided, in accordance with an application of the present invention, apparatus including an implantable structure, which includes:
 a flexible sleeve, having first and second sleeve ends; and
 a contracting assembly, which includes:
  a contracting mechanism, which is disposed longitudinally at a first site of the sleeve; and
  a longitudinal contracting member, having (a) a first member end, (b) a second member end, which is coupled to the sleeve longitudinally at a second site, which is longitudinally between the first site and the second sleeve end, exclusive, and (c) a first member end portion, which (i) extends from the first member end toward the second member end along only a longitudinal portion of the contracting member, and (ii) is coupled to the contracting mechanism,
  wherein the contracting mechanism is configured to apply a longitudinal contracting force only between the first and the second sites; and
 a plurality of tissue anchors, one or more of which are coupled to the sleeve at respective third sites selected from the group of sites consisting of: one or more sites longitudinally between the first site and the first sleeve end, exclusive, and one or more sites longitudinally between the second site and the second sleeve end, exclusive.

For some applications, at least one of the third sites is longitudinally between the first site and the first sleeve end, exclusive. For some applications, at least two of the third sites are longitudinally between the first site and the first sleeve end, exclusive.

For some applications, at least one of the third sites is longitudinally between the second site and the second sleeve end, exclusive. For some applications, at least two of the third sites are longitudinally between the second site and the second sleeve end, exclusive.

For some applications, at least one of the third sites is longitudinally between the first site and the first sleeve end, exclusive, and at least one of the third sites is longitudinally between the second site and the second sleeve end, exclusive.

For some applications, the first site is a first longitudinal distance from the first sleeve end; the second site is at a second longitudinal distance from the second sleeve end, which first and second longitudinal distances are measured when the sleeve is in a straight, relaxed, non-contracted state; and at least one of the first and second longitudinal distances, taken separately, is at least 5 mm. For some applications, the first distance is at least 5 mm. Alternatively or additionally, for some applications, the second distance is at least 5 mm. For some applications, at least one of the first and second longitudinal distances, taken separately, is at least 9 mm, such as at least 18 mm.

For some applications, a first portion of the sleeve longitudinally extends from the first sleeve end toward the first site, a second portion of the sleeve longitudinally extends from the second sleeve end toward the second site, and the sleeve is arranged in a closed loop, such that the first and second portions of the sleeve together define a longitudinally overlapping portion of the sleeve. For some applications, at least one of the tissue anchors penetrates both the first and second portions of the sleeve at the overlapping portion. For some applications, the at least one of the tissue anchors includes a coupling head and a tissue coupling element, the tissue coupling element penetrates both the first and second portions of the sleeve at the overlapping portion, and the coupling head is positioned within one of the first and second portions of the sleeve at the overlapping portion.

For some applications, the overlapping portion has a length of between 5 and 60 mm. For some applications, the contracting member does not extend along the first portion of the sleeve, and does not extend along the second portion of the sleeve.

For any of the applications described above, the contracting mechanism may includes a housing and a rotatable structure positioned within the housing, which housing is disposed at the first site of the sleeve, and the rotatable structure and the longitudinal contracting member may be arranged such that rotation of the rotatable structure applies the longitudinal contracting force only between the first and the second sites.

For any of the applications described above, at least three of the tissue anchors may be coupled to the sleeve alongside the contracting member, longitudinally between the first and second sites, exclusive.

For any of the applications described above, the sleeve may be substantially longitudinally non-extensible.

There is additionally provided, in accordance with an application of the present invention, apparatus including an implantable structure, which includes:

a flexible sleeve, having first and second sleeve ends; and
a contracting assembly, which is configured to longitudinal contract the sleeve, and which includes:
a contracting mechanism;
a first longitudinal contracting member, which has first and second member ends, and a first member end portion, which extends from the first member end toward the second member end along only a longitudinal portion of the first contracting member; and
a second longitudinal contracting member, which has first and second member ends, and a first member end portion, which extends from the first member end toward the second member end along only a longitudinal portion of the second contracting member; and
wherein (a) the first member end of the first contracting member and the first member end of the second contracting member are coupled to the contracting mechanism, (b) the second member end of the first longitudinal contracting member is coupled to the sleeve at a first site that is a first longitudinal distance from the first sleeve end, and (c) the second member end of the second longitudinal contracting member is coupled to the sleeve at a second site that is a second longitudinal distance from the second sleeve end,
wherein the contracting mechanism is disposed at a third site of the sleeve that is longitudinally between the first and second sites, exclusive, and
wherein the first and second longitudinal distances are measured when the sleeve is in a straight, relaxed, non-contracted state, and at least one of the first and second longitudinal distances, taken separately, is at least 5 mm.

For some applications, the implantable structure further includes a plurality of tissue anchors, one or more of which are coupled to the sleeve at respective fourth sites selected from the group of sites consisting of: one or more sites longitudinally between the first site and the first sleeve end, exclusive, and one or more sites longitudinally between the second site and the second sleeve end, exclusive. For some applications, at least three of the tissue anchors are coupled to the sleeve alongside the contracting member, longitudinally between the first and second sites, exclusive.

For some applications, each of the first and second longitudinal distances is at least 5 mm. Alternatively, for some applications, one of the first and second longitudinal distances is at least 5 mm, and the other of the first and second longitudinal distances is less than 5 mm, such as equal to 0 mm.

For any of the applications described above, the contracting mechanism may include a housing and a rotatable structure positioned within the housing, which housing is disposed at the third site of the sleeve, and the rotatable structure and the longitudinal contracting member may be arranged such that rotation of the rotatable structure longitudinally contracts the sleeve.

For any of the applications described above, each of the first and second longitudinal contracting members includes at least one wire.

There is yet additionally provided, in accordance with an application of the present invention, apparatus including an implantable structure, which includes:

a flexible sleeve, arranged as a loop;
a plurality of first tissue anchors of a first configuration, coupled to the sleeve at intervals along a first longitudinally-contiguous portion of the loop; and
a plurality of second tissue anchors of a second configuration different from the first configuration, coupled to the sleeve at intervals along a second longitudinally-contiguous portion of the loop different from the first longitudinally-contiguous portion.

For some applications, the first and second configurations are different from each other in size. For some applications, the first tissue anchors include first coupling heads and first tissue coupling elements, respectively, the second tissue anchors include second coupling heads and second tissue coupling elements, respectively, and lengths of the first tissue coupling elements are greater than lengths of the second tissue coupling elements. For some applications, the implantable structure includes more first tissue anchors than second tissue anchors, such as at least twice as many first tissue anchors as second tissue anchors.

For some applications, the first and second tissue coupling elements are shaped so as to define a shape selected from the group consisting of: a helix, a spiral, and a screw shaft, and the lengths of the first and second coupling elements are measured along a longitudinal axis of the shape. For some applications, each of the second tissue coupling elements is shaped so as to define no more than two turns.

For some applications, the first tissue anchors include first coupling heads and first tissue coupling elements, respectively, the second tissue anchors include second coupling heads and second tissue coupling elements, respectively; the first and second tissue coupling elements are shaped so as to define a shape selected from the group consisting of: a helix, a spiral, and a screw shaft; and each of the second tissue coupling elements has fewer turns than does each of the first tissue coupling elements.

For some applications, each of the second tissue coupling elements is selected from the group consisting of: a harpoon anchor, an anchor including spiked arms, a mesh shaped so as to define two discs, an anchor including a barbed shaft. For some applications, each of the second tissue coupling elements includes a suture.

For any of the applications described above, the flexible sleeve may be shaped so as to define an integrally closed loop having no sleeve ends.

For any of the applications described above, the flexible sleeve may be shaped so as to define first and second sleeve ends, which are coupled to each other to form the loop. For some applications, the first and second sleeve ends are coupled to each other at an overlapping portion.

There is also provided, in accordance with an application of the present invention, apparatus including an implantable structure, which includes:

a flexible sleeve, having first and second sleeve ends;

a contracting assembly, which is configured to longitudinally contract the sleeve;

an elongated linking member, having a first and second linking member ends, which second linking member end includes a first coupling element, wherein the linking member is coupled to the sleeve such that (a) at least a portion of the linking member is disposed within the sleeve, and (b) the first linking member end is longitudinally between the second linking member end and the first sleeve end, exclusive; and a second coupling element, which is configured to be coupleable to the first coupling element, and which is coupled to the implantable structure within 1.5 cm of the first sleeve end, measured when the sleeve is fully longitudinally extended.

For some applications, the implantable structure further includes a plurality of tissue anchors, at least two of which are coupled to the sleeve at respective, different longitudinal sites alongside the linking member.

For some applications, the contracting assembly includes a contracting mechanism and a longitudinal contracting member, and the contracting mechanism is coupled to the sleeve within 1.5 cm of the first sleeve end. For some applications, the second coupling element is coupled to the contracting mechanism.

For some applications, the linking member is configured as a spring. For some applications, the linking member is curved.

For some applications, the linking member has a length of between 2 and 6 cm.

For some applications, the linking member includes metal, such as Nitinol.

For some applications, the linking member is substantially longitudinally non-extensible.

For some applications, at least 30% of a length of the linking member is disposed within the sleeve.

For some applications, the flexible sleeve is a first flexible sleeve, and the implantable structure further includes a second flexible sleeve, and at least 20% of a length of the linking member is disposed within the second flexible sleeve.

For some applications, at least one of the first and second coupling elements includes a hook. For some applications, at least one of the first and second coupling elements includes a loop.

For any of the applications described above, the longitudinal contracting member may include at least one wire.

For any of the applications described above, the implantable structure may further include one or more contraction-restricting elements coupled to at least a contraction-restricted portion of the implant structure, each of which contraction-restricting elements includes a coiled element, a portion of which is non-compressible.

There is further provided, in accordance with an application of the present invention, apparatus including an implantable structure, which includes:

a flexible sleeve, which includes a plurality of radiopaque markers, positioned along the sleeve at respective longitudinal sites; and a plurality of tissue anchors, which are configured to be coupled to the sleeve.

For some applications, the radiopaque markers include a radiopaque ink.

For some applications, at least three of the radiopaque markers are longitudinally spaced at a constant interval. For some applications, at least three of the anchors are coupled to the sleeve, longitudinally spaced at the constant interval.

For some applications, the radiopaque markers have respective edges selected from the group consisting of: respective proximal edges, and respective distal edges; the radiopaque markers include first, second, and third radiopaque markers, which first and second markers are adjacent, and which second and third markers are adjacent; and a first longitudinal distance between the selected edge of the first marker and the selected edge of the second marker equals a second longitudinal distance between the selected edge of the second marker and the selected edge of the first marker. For some applications, the anchors include first, second, and third anchors, which first and second anchors are adjacently coupled to the sleeve with the first longitudinal distance therebetween, and which second and third anchors are adjacently coupled to the sleeve with the second longitudinal distance therebetween.

For any of the applications described above, the implantable structure may include an annuloplasty ring, which is configured to be implanted along an annulus of an atrioventricular valve of a subject, and to contract the annulus as the sleeve is longitudinally contracted.

For any of the applications described above, the apparatus may further include a prosthetic heart valve, which is configured to be coupled to the sleeve.

There is still further provided, in accordance with an application of the present invention, a method including:

providing an implantable structure, which includes (a) a flexible sleeve and (b) a contracting assembly, which is configured to longitudinally contract the sleeve, and which includes (i) a contracting mechanism and (ii) one or more longitudinal contracting members coupled to the contracting mechanism;

placing (typically in a percutaneous procedure) the implantable structure completely around an annulus of an atrioventricular valve of a subject, such that none of the one or more longitudinal contracting members is positioned along an anterior portion of the annulus between fibrous trigones of the valve;

fastening the implantable structure to the annulus; and actuating the contracting assembly to contract a longitudinal portion of the sleeve not positioned along the anterior portion of the annulus.

For some applications, providing the implantable structure includes providing the implantable structure in which the sleeve is shaped so as to define an integrally closed loop having no sleeve ends.

For some applications, providing the implantable structure includes providing the implantable structure in which the sleeve has first and second sleeve ends, and first and second portions that longitudinally extend from the first and the second sleeve ends, respectively; placing the implantable structure includes arranging the sleeve in a closed loop, such that the first and second portions of the sleeve together define a longitudinally overlapping portion of the sleeve positioned at least partially along the anterior portion of the annulus; and none of the one or more longitudinal contracting members is positioned along the overlapping portion of the sleeve. For some applications, fastening the implantable structure to the annulus includes fastening the sleeve to the annulus using a plurality of tissue anchors, at least one of which penetrates both the first and second portions of the sleeve at the overlapping portion.

For some applications, the at least one of the tissue anchors includes a coupling head and a tissue coupling element, and fastening includes fastening the sleeve to the annulus such that the tissue coupling element penetrates both the first and second portions of the sleeve at the overlapping portion, and the coupling head is positioned within one of the first and second portions of the sleeve at the overlapping portion.

For some applications, the plurality of tissue anchors includes a plurality of first tissue anchors of a first configuration, and a plurality of second tissue anchors of a second configuration different from the first configuration, and fastening includes: (a) coupling the first tissue anchors to the sleeve at intervals along a first longitudinally-contiguous portion of the loop positioned along a portion of the annulus other than the anterior portion of the annulus, and (b) coupling the second tissue anchors to the sleeve at intervals along a second longitudinally-contiguous portion of the loop positioned along the anterior portion of the annulus. The first and second tissue anchors are optionally configured as described below. The For some applications, the contracting member does not extend along the first portion of the sleeve, and does not extend along the second portion of the sleeve.

For some applications, placing includes placing the implantable structure such that the one or more longitudinal contracting members are positioned along a non-anterior portion of the annulus, which non-anterior portion does not reach either of the fibrous trigones.

For some applications, the contracting mechanism includes a housing and a rotatable structure positioned within the housing, which housing is disposed at the first site of the sleeve, and actuating the contracting assembly includes rotating the rotatable structure to longitudinally contract the sleeve.

There is additionally provided, in accordance with an application of the present invention, a method including:

providing an implantable structure, which includes (a) a flexible sleeve, having first and second sleeve ends, and (b) a contracting assembly, which is configured to longitudinally contract the sleeve, and which includes (i) a contracting mechanism, which is disposed longitudinally at a first site of the sleeve, and (ii) a longitudinal contracting member, having (x) a first member end, (y) a second member end, which is coupled to the sleeve longitudinally at a second site, which is longitudinally between the first site and the second sleeve end, exclusive, and (z) a first member end portion, which (1) extends from the first member end toward the second member end along only a longitudinal portion of the contracting member, and (2) is coupled to the contracting mechanism;

placing (typically in a percutaneous procedure) the implantable structure at least partially around an annulus of an atrioventricular valve of a subject;

using a plurality of tissue anchors, fastening the implantable structure to the annulus, including coupling one or more of the tissue anchors to the sleeve and tissue of the annulus at respective third sites longitudinally between the second site and the second sleeve end, exclusive; and actuating the contracting assembly to contract a longitudinal portion of the sleeve.

For some applications, coupling the one or more tissue anchors includes coupling at least two of the tissue anchors to the sleeve and the tissue at respective third sites longitudinally between the second member end and the second sleeve end, exclusive.

For some applications, providing the implantable structure includes providing the implantable structure in which the second site is at least 5 mm from the second sleeve end, measured when the sleeve is in a straight, relaxed, non-contracted state.

For some applications, providing the implantable structure includes providing the implantable structure in which the second site is at a longitudinal distance from the second sleeve end, which distance is no greater than 30% of a total length of the sleeve, the distance and length measured when the sleeve is in the straight, relaxed, non-contracted state.

For some applications, a first portion of the sleeve longitudinally extends from the first sleeve end toward the first site, a second portion of the sleeve longitudinally extends from the second sleeve end toward the second site, and placing the implantable structure includes arranging the sleeve in a closed loop, such that the first and second portions of the sleeve together define a longitudinally overlapping portion of the sleeve. For some applications, placing the implantable structure includes placing the implantable structure such that the overlapping portion is positioned along an anterior portion of the annulus between fibrous trigones of the valve. For some applications, fastening includes coupling at least one of the tissue anchors to the tissue such that the anchor penetrates both the first and second portions of the sleeve at the overlapping portion. For some applications, the at least one of the tissue anchors includes a coupling head and a tissue coupling element, and fastening includes fastening the sleeve to the annulus such that the tissue coupling element penetrates both the first and second portions of the sleeve at the overlapping portion, and the coupling head is positioned within one of the first and second portions of the sleeve at the overlapping portion.

For some applications, providing the implantable structure includes providing the implantable structure in which the overlapping portion has a length of between 5 and 60 mm. For some applications, providing the implantable structure includes providing the implantable structure in which the contracting member does not extend along the first portion of the sleeve, and does not extend along the second portion of the sleeve.

For some applications, the contracting mechanism includes a housing and a rotatable structure positioned within the housing, which housing is disposed at the first site of the sleeve, and actuating the contracting assembly includes rotating the rotatable structure to longitudinally contract the sleeve.

For some applications, coupling includes coupling at least three of the tissue anchors to the sleeve alongside the contracting member, longitudinally between the first and second sites, exclusive.

For some applications, actuating includes actuating the contracting assembly to apply a longitudinal contracting force only between the first and the second sites.

There is yet additionally provided, in accordance with an application of the present invention, a method including:

providing an implantable structure, which includes (a) a flexible sleeve, having first and second sleeve ends, and (b) a contracting assembly, which includes (i) a contracting mechanism, which is disposed longitudinally at a first site of the sleeve, and (ii) a longitudinal contracting member, having (x) a first member end, (y) a second member end, which is coupled to the sleeve longitudinally at a second site, which is longitudinally between the first site and the second sleeve end, exclusive, and (z) a first member end portion, which (1) extends from the first member end toward the second member end along only a longitudinal portion of the contracting member, and (2) is coupled to the contracting mechanism, wherein the contracting mechanism is configured to apply a longitudinal contracting force only between the first and the second sites; and placing (typically in a percutaneous procedure) the implantable structure at least partially around an annulus of an atrioventricular valve of a subject;

using a plurality of tissue anchors, fastening the implantable structure to the annulus, including coupling one or more of the tissue anchors to the sleeve and tissue of the annulus at respective third sites selected from the group of sites consisting of: one or more sites longitudinally between the first site and the first sleeve end, exclusive, and one or more sites longitudinally between the second site and the second sleeve end, exclusive; and actuating the contracting assembly to contract a longitudinal portion of the sleeve.

For some applications, at least one of the third sites is longitudinally between the first site and the first sleeve end, exclusive. For some applications, at least two of the third sites are longitudinally between the first site and the first sleeve end, exclusive.

For some applications, at least one of the third sites is longitudinally between the second site and the second sleeve end, exclusive. For some applications, at least two of the third sites are longitudinally between the second site and the second sleeve end, exclusive.

For some applications, at least one of the third sites is longitudinally between the first site and the first sleeve end, exclusive, and at least one of the third sites is longitudinally between the second site and the second sleeve end, exclusive.

For some applications, providing the implantable structure includes providing the implantable structure in which the first site is a first longitudinal distance from the first sleeve end, the second site is at a second longitudinal distance from the second sleeve end, which first and second longitudinal distances are measured when the sleeve is in a straight, relaxed, non-contracted state, and at least one of the first and second longitudinal distances, taken separately, is at least 5 mm. For some applications, the first distance is at least 5 mm. Alternatively or additionally, for some applications, the second distance is at least 5 mm.

For some applications, a first portion of the sleeve longitudinally extends from the first sleeve end toward the first site, a second portion of the sleeve longitudinally extends from the second sleeve end toward the second site, and placing the implantable structure includes arranging the sleeve in a closed loop, such that the first and second portions of the sleeve together define a longitudinally overlapping portion of the sleeve. For some applications, placing the implantable structure includes placing the implantable structure such that the overlapping portion is positioned along an anterior portion of the annulus between fibrous trigones of the valve.

For some applications, fastening includes coupling at least one of the tissue anchors to the tissue such that the anchor penetrates both the first and second portions of the sleeve at the overlapping portion. For some applications, the at least one of the tissue anchors includes a coupling head and a tissue coupling element, and fastening includes fastening the sleeve to the annulus such that the tissue coupling element penetrates both the first and second portions of the sleeve at the overlapping portion, and the coupling head is positioned within one of the first and second portions of the sleeve at the overlapping portion.

For some applications, providing the implantable structure includes providing the implantable structure in which the overlapping portion has a length of between 5 and 60 mm. For some applications, providing the implantable structure includes providing the implantable structure in which the contracting member does not extend along the first portion of the sleeve, and does not extend along the second portion of the sleeve.

For some applications, the contracting mechanism includes a housing and a rotatable structure positioned within the housing, which housing is disposed at the first site of the sleeve, and actuating the contracting assembly includes rotating the rotatable structure to longitudinally contract the sleeve.

For some applications, coupling includes coupling at least three of the tissue anchors to the sleeve alongside the contracting member, longitudinally between the first and second sites, exclusive.

There is also provided, in accordance with an application of the present invention, a method including:

providing an implantable structure, which includes (a) a flexible sleeve, having first and second sleeve ends, and (b) a contracting assembly, which is configured to longitudinal contract the sleeve, and which includes (i) a contracting mechanism, (ii) a first longitudinal contracting member, which has first and second member ends, and a first member end portion, which extends from the first member end toward the second member end along only a longitudinal portion of the first contracting member, and (iii) a second longitudinal contracting member, which has first and second member ends, and a first member end portion, which extends from the first member end toward the second member end along only a longitudinal portion of the second contracting member, wherein (a) the first member end of the first contracting member and the first member end of the second contracting member are coupled to the contracting mechanism, (b) the second member end of the first longitudinal contracting member is coupled to the sleeve at a first site that is a first longitudinal distance from the first sleeve end, (c) the second member end of the second longitudinal contracting member is coupled to the sleeve at a second site that is a second longitudinal distance from the second sleeve end, (d) the contracting mechanism is disposed at a third site of the sleeve that is longitudinally between the first and second sites, exclusive, and (e) the first and second longitudinal distances are measured when the sleeve is in a straight, relaxed, non-contracted state, and at least one of the first and second longitudinal distances, taken separately, is at least 5 mm;

placing (typically in a percutaneous procedure) the implantable structure at least partially around an annulus of an atrioventricular valve of a subject;

fastening the implantable structure to the annulus; and actuating the contracting assembly to contract two longitudinal portions of the sleeve.

For some applications, fastening includes fastening the implantable structure to the annulus using a plurality of tissue anchors, including coupling one or more of the tissue anchors to the sleeve and tissue of the annulus at respective fourth sites selected from the group of sites consisting of: one or more sites longitudinally between the first site and the first sleeve end, exclusive, and one or more sites longitudinally between the second site and the second sleeve end, exclusive. For some applications, fastening includes coupling at least three of the tissue anchors to the sleeve alongside the contracting member, longitudinally between the first and second sites, exclusive.

For some applications, each of the first and second longitudinal distances is at least 5 mm.

For some applications, one of the first and second longitudinal distances is at least 5 mm, and the other of the first and second longitudinal distances is less than 5 mm, such as equal to 0 mm.

For any of the applications described above, the contracting mechanism may include a housing and a rotatable structure positioned within the housing, which housing is disposed at the third site of the sleeve, and actuating the contracting assembly may include rotating the rotatable structure to longitudinally contract the sleeve.

There is further provided, in accordance with an application of the present invention, a method including:

placing (typically in a percutaneous procedure) a flexible sleeve as a loop completely around an annulus of an atrioventricular valve of a subject, such that (a) a first longitudinally-contiguous portion of the loop is positioned along a portion of the annulus other than an anterior portion of the annulus between fibrous trigones of the valve, and (b) a second longitudinally-contiguous portion of the loop is positioned along the anterior portion of the annulus;

coupling a plurality of first tissue anchors of a first configuration to the sleeve and tissue of the annulus at intervals along the first longitudinally-contiguous portion of the loop; and coupling a plurality of second tissue anchors of a second configuration different from the first configuration to the sleeve and the tissue at intervals along the second longitudinally-contiguous portion of the loop.

For some applications, the first and second configurations are different from each other in size. For some applications, the first tissue anchors included first coupling heads and first tissue coupling elements, respectively, the second tissue anchors include second coupling heads and second tissue coupling elements, respectively, and lengths of the first tissue coupling elements are greater than lengths of the second tissue coupling elements. For some applications, coupling the first and the second tissue anchors includes coupling more first tissue anchors than second tissue anchors. For some applications, coupling the first and the second tissue anchors includes coupling at least twice as many first tissue anchors as second tissue anchors.

For some applications, the first and second tissue coupling elements are shaped so as to define a shape selected from the group consisting of: a helix, a spiral, and a screw shaft, and the lengths of the first and second coupling elements are measured along a longitudinal axis of the shape. For some applications, each of the second tissue coupling elements is shaped so as to define no more than two turns.

For some applications, the first tissue anchors include first coupling heads and first tissue coupling elements, respectively; the second tissue anchors include second coupling heads and second tissue coupling elements, respectively; the first and second tissue coupling elements are shaped so as to define a shape selected from the group consisting of: a helix, a spiral, and a screw shaft; and each of the second tissue coupling elements has fewer turns than does each of the first tissue coupling elements.

For some applications, each of the second tissue coupling elements is selected from the group consisting of: a harpoon anchor, an anchor including spiked arms, a mesh shaped so as to define two discs, an anchor including a barbed shaft.

For some applications, each of the second tissue coupling elements includes a suture.

For some applications, the flexible sleeve is shaped so as to define an integrally closed loop having no sleeve ends.

For some applications, the flexible sleeve is shaped so as to define first and second sleeve ends, and placing includes placing the flexible sleeve includes coupling the first and the second sleeve ends to each other to form the loop. For some applications, coupling the first and the second sleeve ends includes coupling the first and the second sleeve ends to each other at an overlapping portion.

There is still further provided, in accordance with an application of the present invention, a method including:

providing an implantable structure, which includes (a) a flexible sleeve, having first and second sleeve ends, (b) a contracting assembly, which is configured to longitudinally contract the sleeve, (c) an elongated linking member, having a first and second linking member ends, which second linking member end includes a first coupling element, the linking member is coupled to the sleeve such that (i) at least a portion of the linking member is disposed within the sleeve, and (ii) the first linking member end is longitudinally between the second linking member end and the first sleeve end, exclusive, and (d) a second coupling element, which is coupled to the implantable structure within 1.5 cm of the first sleeve end, measured when the sleeve is fully longitudinally extended;

placing (typically in a percutaneous procedure) the flexible sleeve around a portion of an annulus of an atrioventricular valve of a subject, which portion includes a posterior portion of the annulus;

placing the linking member along an anterior portion of the annulus between fibrous trigones of the valve;

fastening the flexible sleeve to the portion of the annulus;

coupling the first and the second coupling elements together;

actuating the contracting assembly to contract a longitudinal portion of the sleeve.

For some applications, fastening includes fastening the sleeve to the annulus using a plurality of tissue anchors, including coupling at least two of the anchors to the sleeve and tissue of the annulus at respective, different longitudinal sites alongside the linking member.

For some applications, the contracting assembly includes a contracting mechanism and a longitudinal contracting member, and the contracting mechanism is coupled to the sleeve within 1.5 cm of the first sleeve end. For some applications, the second coupling element is coupled to the contracting mechanism.

For some applications, the linking member is configured as a spring. For some applications, the linking member is curved.

For some applications, the linking member has a length of between 2 and 6 cm.

For some applications, the linking member includes metal, such as Nitinol.

For some applications, the linking member is substantially longitudinally non-extensible.

For some applications, at least 30% of a length of the linking member is disposed within the sleeve.

For some applications, the flexible sleeve is a first flexible sleeve, and the implantable structure further includes a second flexible sleeve, and at least 20% of a length of the linking member is disposed within the second flexible sleeve.

For some applications, at least one of the first and second coupling elements includes a hook. For some applications, at least one of the first and second coupling elements includes a loop.

There is additionally provided, in accordance with an application of the present invention, a method including:

placing (typically in a percutaneous procedure), at least partially around an annulus of an atrioventricular valve of a subject, a flexible sleeve, which includes a plurality of radiopaque markers, positioned along the sleeve at respective longitudinal sites;

generating a radiographic image of the sleeve; and using the radiographic image, coupling a plurality of tissue anchors to the sleeve and tissue of the annulus.

For some applications, coupling includes using the radiographic image to enable setting a desired distance between the anchors along the sleeve.

For some applications, the radiopaque markers include a radiopaque ink.

For some applications, at least three of the radiopaque markers are longitudinally spaced at a constant interval. For some applications, at least three of the anchors are coupled to the sleeve, longitudinally spaced at the constant interval.

For some applications, the radiopaque markers have respective edges selected from the group consisting of: respective proximal edges, and respective distal edges; the radiopaque markers include first, second, and third radiopaque markers, which first and second markers are adjacent, and which second and third markers are adjacent; and a first longitudinal distance between the selected edge of the first marker and the selected edge of the second marker equals a second longitudinal distance between the selected edge of the second marker and the selected edge of the first marker. For some applications, the anchors include first, second, and third anchors, and coupling includes adjacently coupling the first and the second anchors to the sleeve with the first longitudinal distance therebetween, and adjacently coupling the second and the third anchors to the sleeve with the second longitudinal distance therebetween.

The present invention will be more fully understood from the following detailed description of applications thereof, taken together with the drawings, in which:

BRIEF DESCRIPTION OF THE DRAWINGS

FIG. 1 is a schematic illustration of a system for repairing a dilated atrioventricular valve, such as a mitral valve, in accordance with an application of the present invention;

FIGS. 2A-I are schematic illustrations of a procedure for implanting the implantable structure of FIG. 1 to repair a mitral valve, in accordance with an application of the present invention;

FIG. 3 is a schematic illustration of another configuration of the implantable structure of FIG. 1, prior to implantation, in accordance with an application of the present invention;

FIG. 4 is a schematic illustration of the implantable structure of FIG. 3 after implantation around the annulus of a mitral valve, in accordance with an application of the present invention;

FIGS. 5A-I are schematic illustrations of different configurations of tissue anchors, in accordance with respective applications of the present invention;

FIGS. 9A-B are schematic illustrations of coupling elements, in accordance with respective applications of the present invention;

FIGS. 10A-E are schematic illustrations of configurations of the system of FIG. 1 comprising a coiled element, in accordance with respective applications of the present invention;

FIGS. 11A-E are schematic illustrations of additional configurations of the system of FIG. 1 comprising a coiled element, in accordance with respective applications of the present invention;

FIG. 13 is a schematic illustration of still another configuration of the implantable structure of FIG. 1, in accordance with an application of the present invention;

DETAILED DESCRIPTION OF EMBODIMENTS

Figure 2A:
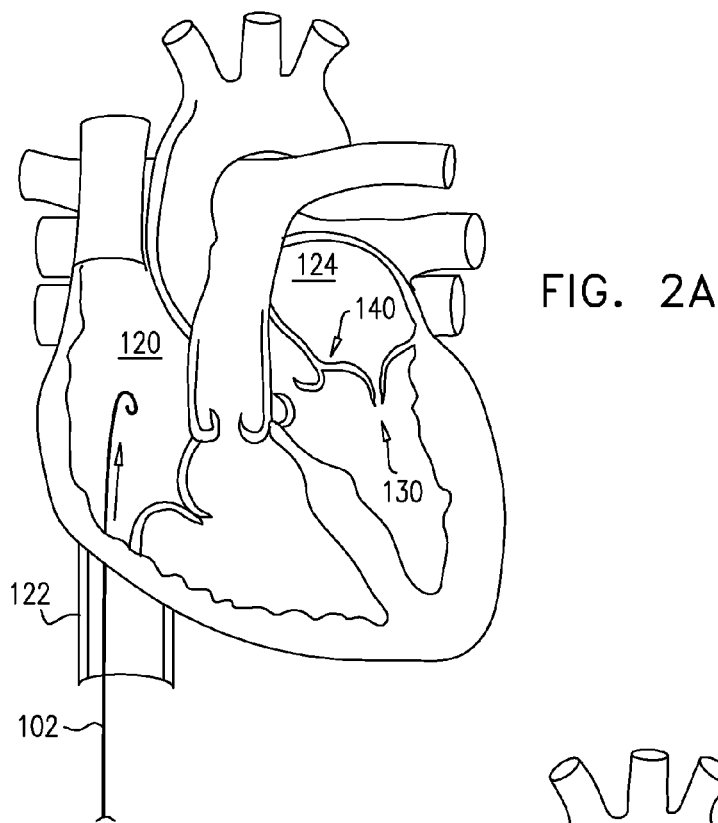

FIG. 1 is a schematic illustration of a system 20 for repairing a dilated atrioventricular valve, such as a mitral valve or a tricuspid valve, in accordance with an application of the present invention. System 20 comprises an adjustable implantable structure 22, shown in FIG. 1 in a straight, relaxed, non-contracted state, and an anchor deployment manipulator 24 (shown in FIGS. 2G-H). For some applications, implantable structure 22 is configured to be deployed as an annuloplasty ring, while for other applications, implantable structure 22 is configured to be deployed as a base ring to which a prosthetic valve is coupled, such as described hereinbelow with reference to FIG. 15A-B or 16. Implantable structure 22 comprises a flexible sleeve 26. Anchor deployment manipulator 24 is advanced into sleeve 26, as shown in FIGS. 2G-H, and, from within the sleeve, deploys tissue anchors through a wall of the sleeve into cardiac tissue, thereby anchoring the ring around at least a portion of the valve annulus. For some applications, anchor deployment manipulator is implemented using techniques described in US Patent Application Publication 2010/0280604, which is incorporated herein by reference, with reference to FIGS. 2, 3, 4, 5A, 5B, 6A, 6B, 7, 8, 13, and/or 20A-E thereof.

For some applications, implantable structure 22 comprises a partial annuloplasty ring. In these applications, sleeve 26 is configured to be placed only partially around the valve annulus (i.e., to assume a C-shape), and, once anchored in place, to be contracted so as to circumferentially tighten the valve annulus. For other applications, sleeve 26 is configured to be implanted entirely around the valve annulus in a closed loop, such as described hereinbelow with reference to FIG. 4. 6, 8, or 15A-B.

Implantable structure 22 further comprises a contracting assembly 40, which facilitates contracting of the implantable structure. Contracting assembly 40 comprises a contracting mechanism 28, and a longitudinal contracting member 30, which is coupled to contracting mechanism 28, extends along a portion of the sleeve, and is typically flexible. For example, contracting member 30 may comprise at least one wire. Contracting assembly 40 is described in more detail hereinbelow. In addition, the implantable structure typically comprises a plurality of tissue anchors 38, typically between about 5 and about 20 anchors, such as about 10 or about 16 anchors. In FIG. 1, anchors 38 are shown coupled to implantable structure 22, deployed through the wall of sleeve 26. For some applications, anchors 38 are configured as described hereinbelow with reference to FIGS. 5A-C, 5D, 5E, 5F, 5G, 5H, and/or 5I, while for other applications, anchors 38 comprise tissue anchors known in the art.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 24 within the sleeve. The fabric fibers may promote tissue growth into the braid. Typically, sleeve 26 is substantially longitudinally non-extensible, i.e., a length thereof is substantially constant, i.e., cannot be longitudinally stretched, under normal usage conditions. Alternatively, the sleeve is somewhat elastic, which gives the sleeve a tendency to longitudinally contract, thereby helping tighten the sleeve. For example, the sleeve may be bellows- or accordion-shaped.

For some applications, the sleeve is configured to have a tendency to assume a straight shape when in its relaxed, non-contracted state. This straightness may help the surgeon locate the next site for each subsequent anchor during the implantation procedure. For example, because the sleeve assumes a generally straight shape, the sleeve may help provide an indication of distance between adjacent anchoring sites. For some applications, the sleeve is configured to have a controllably variable stiffness. For example, a somewhat stiff wire may be placed in the sleeve to provide the stiffness, and subsequently be removed at the conclusion of the implantation procedure when the stiffness is no longer useful.

For some applications, sleeve 26 comprises a plurality of radiopaque markers 39, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 38 along the sleeve. For some applications, the markers comprise a radiopaque ink.

Typically, at least a portion (e.g., at least three, such as all) of the longitudinal sites are longitudinally spaced at a constant interval. Typically, the longitudinal distance between the distal edges of adjacent markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm. (If, for example, the distance were 6 mm and the length were 2 mm, the longitudinal gaps between adjacent markers would have lengths of 4 mm.)

Longitudinal contracting member 30 comprises a wire, a ribbon, a rope, or a band, which typically comprises a flexible and/or superelastic material, e.g., nitinol, polyester, HDPE, stainless steel, or cobalt chrome. For some applications, the wire comprises a radiopaque material. For some applications, longitudinal contracting member 30 comprises a braided polyester suture (e.g., Ticron). For some applications, longitudinal contracting member 30 is coated with polytetrafluoroethylene (PTFE). For some applications, contracting member 30 comprises a plurality of wires that are intertwined to form a rope structure. For some applications, implantable structure 22 comprises a plurality of contracting members 30, which may extend along generally the same longitudinal portion of sleeve 26, or along respective, different portions of sleeve 26 (e.g., as described hereinbelow with reference to FIG. 13).

For some applications, contracting member 30 is positioned at least partially within a lumen of the sleeve 26, such as entirely within the lumen (as shown in FIGS. 1, 2H-I, 3, 4, 7, and 8). For some applications in which the contracting member is positioned partially within the lumen, the contracting member is sewn into the wall of the sleeve, such that the contracting member is alternatingly inside and outside of the sleeve along the length of the sleeve (configuration not shown). Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which contracting member 30 is positioned, or the sleeve may comprise or be shaped so as to define external coupling elements, such as loops or rings (configuration not shown). For some applications, contracting member 30 is positioned approximately opposite the anchors.

For some applications of the present invention, contracting mechanism 28 comprises a rotatable structure, such as a spool 46. The rotatable structure is arranged such that rotation thereof applies a longitudinal contracting force, thereby contracting at least a longitudinal portion of implantable structure 22. Typically, in these applications, contracting mechanism 28 further comprises a housing 44 in which the rotatable structure, e.g., the spool, is positioned. Contracting member 30 has first and second member ends, and a first member end portion, which extends from the first member end toward the second member end along only a longitudinal portion of the contracting member. For some applications, the first member end portion, e.g., the first member end of contracting member 30, is coupled to contracting mechanism 28, such as the rotatable structure, e.g., the spool (alternatively, although the first member end portion is coupled to the contracting mechanism, the first member end protrudes beyond the contracting mechanism). For example, spool 46 may be shaped to provide a hole 42 or other coupling mechanism for coupling the first end of contracting member 30 to the spool, and thereby to contracting mechanism 28. Contracting assembly 40 is arranged such that rotation of the spool winds a portion of the contracting member around the spool. Alternatively, contracting member 30 may comprise at least one wire (e.g., exactly one wire) that passes through a coupling mechanism of spool 46, in order to couple the wire to the spool. The ends of the wire are brought together, and together serve as a second end 53 of contracting member 30. In this configuration, approximately the longitudinal center of the wire serves as the first end of the contracting member.

Alternatively, contracting mechanism 28 may comprise a ratchet contracting mechanism, which typically comprises a ratchet-coupling housing. Contracting member 30 is shaped so as to define engaging structures, such as grooves or teeth. Techniques may be used that are described in International Application PCT/IL2009/000593, filed Jun. 15, 2009, which published as PCT Publication WO 10/004,546, and in U.S. application Ser. No. 12/996,954, which published as US Patent Application Publication 2011/0166649, in the national stage thereof, all of which applications and publications are incorporated herein by reference.

Further alternatively, contracting mechanism 28 may comprise a housing or other structure (e.g., a ring or an eyelet) which is shaped so as to define an opening therethrough. Contracting member 30 is drawn through the opening (such that the first member end protrudes beyond the opening), and, once a desired length has been achieved, is locked, such as using a locking bead, or by crimping or knotting.

Contracting member 30 extends along less than the entire length of sleeve 26. Contracting mechanism 28 (e.g., housing 44 thereof) is disposed at a first site 34 of sleeve 26 that is a first longitudinal distance D1 from a first end of the sleeve, either a proximal end 49 of sleeve 26, as shown in FIG. 1, or a distal end 51 of sleeve 26, as shown in FIGS. 2G-I. (Longitudinal distance D1 is measured between the first end of the sleeve and the portion of contracting mechanism 28 that is closest to the first end.) For some applications, second end 53 of contracting member 30 is coupled to the sleeve at a second site 36 that is a second longitudinal distance D2 from a second end of the sleeve, which second end is longitudinally opposite the first end of the sleeve. For applications in which contracting mechanism 28 comprises a rotatable structure, rotation of the rotatable structure, such as spool 46, longitudinally contracts at least a portion of the sleeve, such as by winding a portion of the contracting member around the spool, thereby pulling the far end of the implantable structure toward the spool and shortening and tightening the implantable structure. Such rotation of the rotatable structure, or other actuation of contracting assembly 40, typically applies a longitudinal contracting force only between first and second sites 34 and 36, which longitudinally contracts at least a portion, e.g., all, of the sleeve only between first and second sites 34 and 36. (For example, the longitudinal force may longitudinally contract less than the entire sleeve between first and second sites 34 and 36 in applications in which system 20 comprises coiled element 240, which provides a contraction-restricting portion of the sleeve, as described hereinbelow with reference to FIGS. 10A-E and/or 11A-E). Therefore, the portions of the sleeve beyond first and second sites 34 and 36 (towards the ends of the sleeve) are not contracted by contracting assembly 40.

Typically, contracting member 30 extends along (i.e., a distance along the sleeve between first and second sites 34 and 36 equals) no more than 80% of the length of the sleeve, e.g., no more than 60% or no more than 50% of the length. Typically, contracting member 30 extends along no more than 80% of a circumference of the loop when the sleeve is placed around the annulus (i.e., the total length of the loop less the length of any overlapping portion). Typically, contracting member 30 extends along (i.e., a distance along the sleeve between first and second sites 34 and 36 equals) at least 20% of the length of the sleeve, e.g., at least than 40% or at least than 50% of the length. Typically, contracting member 30 extends along at least 20% of the circumference of the loop when the sleeve is placed around the annulus, e.g., at least 30% or at least 50%.

For some applications, first longitudinal distance D1, measured when sleeve 26 is in a straight, relaxed, non-contracted state, is at least 3 mm, e.g., at least 5 mm, such as at least 9 mm, e.g., at least 14 mm; no greater than 20 mm, such as no greater than 15 mm; and/or between 5 and 20 mm, such as between 9 and 15 mm. Alternatively or additionally, for some applications, second longitudinal distance D2, measured when sleeve 26 is in a straight, relaxed, non-contracted state, is at least 3 mm, e.g., at least 5 mm, such as at least 9 mm, e.g., at least 14 mm; no greater than 20 mm, such as no greater than 15 mm; and/or between 5 and 20 mm, such as between 9 and 15 mm. Further alternatively or additionally, first longitudinal distance D1, measured when sleeve 26 is in a straight, relaxed, non-contracted state, is no greater than 20%, such as no greater than 10% of a total length of the sleeve, measured when sleeve 26 is in a straight, relaxed, non-contracted state. Further alternatively or additionally, second longitudinal distance D2, measured when sleeve 26 is in a straight, relaxed, non-contracted state, is no greater than 30%, such as no greater than 20%, e.g., no greater than 10% of the total length of the sleeve measured, when sleeve 26 is in a straight, relaxed, non-contracted state. For some applications, the total length of the sleeve, measured when the sleeve is in a straight, relaxed, non-contracted state is at least 5 cm, no more than 25 cm, and/or between 5 and 25 cm. For some applications in which the sleeve is implanted in a closed loop, the total length of the sleeve is selected to be between 1.3 and 1.4 times a circumference of the annulus, in order to provide overlapping portion 114, described hereinbelow with reference to FIGS. 3 and 4.

For some applications, at least one of tissue anchors 38 (e.g., exactly one, at least two, exactly two, at least three, exactly three, or at least four, or no more than four) is coupled to sleeve 26 longitudinally between contracting mechanism 28 (e.g., housing 44 thereof) and the first sleeve end (i.e., the end of the sleeve to which contracting mechanism 28 is closest), exclusive, and at least 3, such as at least 6, of tissue anchors 38 are coupled to the sleeve alongside contracting member 30, longitudinally between first site 34 and second site 36 (second member end 53), exclusive. (As used in the present application, including in the claims, "exclusive," when used with respect to a range of locations, means excluding the endpoints of the range.)

Alternatively or additionally, for some applications, at least one of tissue anchors 38 (e.g., exactly one, at least two, exactly two, at least three, exactly three, or at least four, or no more than four) is coupled to sleeve 26 longitudinally between second site 36 (second member end 53) and the second sleeve end (i.e., the end of the sleeve to which second member end 53 is closest), exclusive, and at least 3, such as at least 6, of tissue anchors 38 are coupled to the sleeve alongside contracting member 30, longitudinally between first site 34 and second site 36 (second member end 53), exclusive.

In the exemplary configuration shown in FIG. 1, exactly two tissue anchors 38 are coupled to the sleeve longitudinally between the contracting mechanism (e.g., the housing) (first site 34) and the first sleeve end, exclusive, exactly two tissue anchors are coupled to the sleeve longitudinally between first site 34 and second site 36 (second member end 53), exclusive, and exactly six tissue anchors 38 are coupled to the sleeve alongside the contracting member, longitudinally between first site 34 and second site 36 (second member 53), exclusive.

Providing the one or more anchors beyond first and second sites 34 and 36 (i.e., beyond the contracting portion of contracting member 30) generally distributes force applied by contraction of contracting assembly 40 over these anchors. In contrast, in some configurations of implantable structure 22 in which anchors are not provided beyond first and second sites 34 and 36, the force applied by the contracting assembly is applied predominantly to the single anchor nearest the first end of the contracting member, and the single anchor nearest to second end of the contracting member.

For some applications, anchors 38 are positioned along sleeve 26 with a longitudinal distance of between 4.5 and 9 mm, such as 6 mm, between each pair of longitudinally-adjacent anchors.

It is noted that the anchors may be positioned as described above by a surgeon during an implantation procedure, such as described hereinbelow with reference to FIGS. 2A-I, or the anchors may be prepositioned in the sleeve.

Reference is now made to FIGS. 2A-I, which are schematic illustrations of a procedure for implanting implantable structure 22 to repair a mitral valve 130, in accordance with an application of the present invention. The procedure is typically performed with the aid of imaging, such as fluoroscopy, transesophageal echo, and/or echocardiography.

The procedure typically begins by advancing a semi-rigid guidewire 102 into a right atrium 120 of the patient, as shown in FIG. 2A.

Figure 2B:
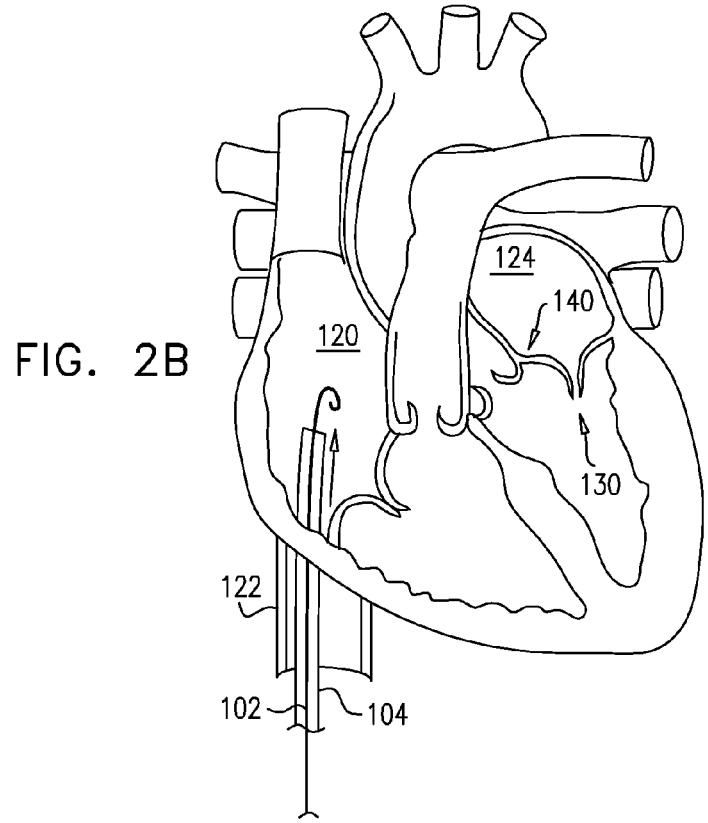
Figure 2C:
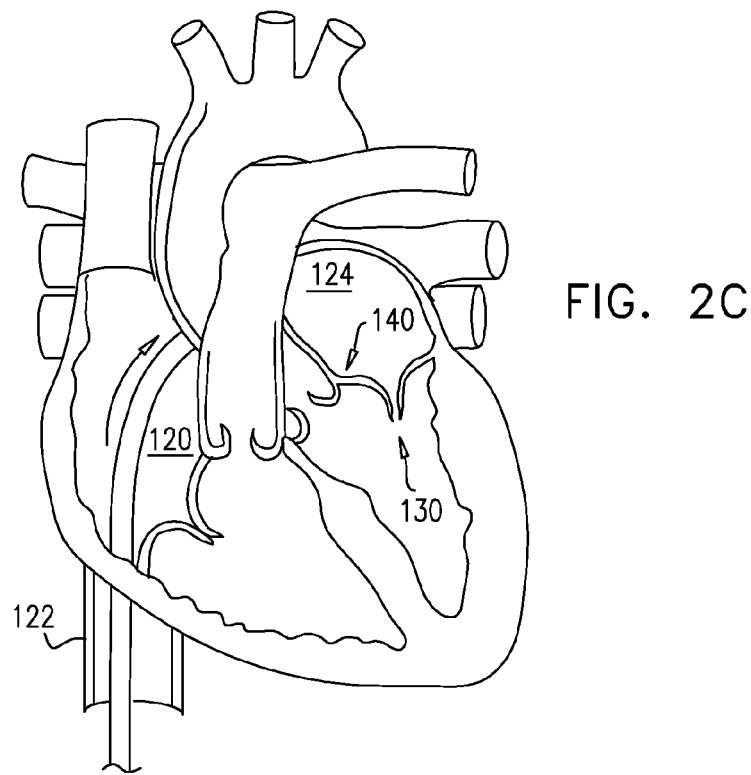

As show in FIG. 2B, guidewire 102 provides a guide for the subsequent advancement of a sheath 104 therealong and into the right atrium. Once sheath 104 has entered the right atrium, guidewire 102 is retracted from the patient's body. Sheath 104 typically comprises a 14-20 F sheath, although the size may be selected as appropriate for a given patient. Sheath 104 is advanced through vasculature into the right atrium using a suitable point of origin typically determined for a given patient. For example:

sheath 104 may be introduced into the femoral vein of the patient, through an inferior vena cava 122, into right atrium 120, and into a left atrium 124 transseptally, typically through the fossa ovalis;

sheath 104 may be introduced into the basilic vein, through the subclavian vein to the superior vena cava, into right atrium 120, and into left atrium 124 transseptally, typically through the fossa ovalis; or sheath 104 may be introduced into the external jugular vein, through the subclavian vein to the superior vena cava, into right atrium 120, and into left atrium 124 transseptally, typically through the fossa ovalis.

For some applications, sheath 104 is advanced through an inferior vena cava 122 of the patient (as shown) and into right atrium 120 using a suitable point of origin typically determined for a given patient.

Sheath 104 is advanced distally until the sheath reaches the interatrial septum.

Figure 2D:
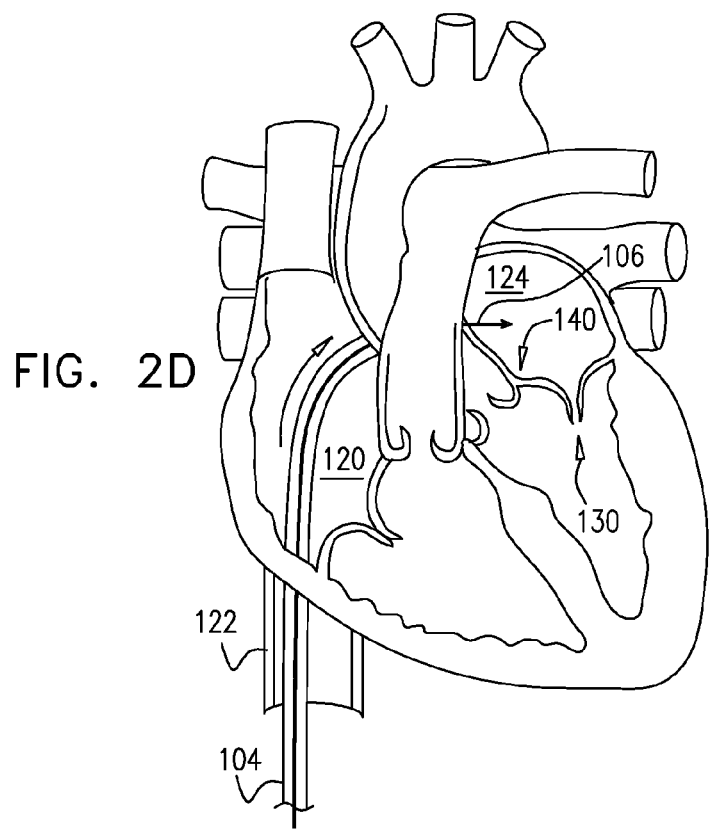

As shown in FIG. 2D, a resilient needle 106 and a dilator (not shown) are advanced through sheath 104 and into the heart. In order to advance sheath 104 transseptally into left atrium 124, the dilator is advanced to the septum, and needle 106 is pushed from within the dilator and is allowed to puncture the septum to create an opening that facilitates passage of the dilator and subsequently sheath 104 therethrough and into left atrium 124. The dilator is passed through the hole in the septum created by the needle. Typically, the dilator is shaped to define a hollow shaft for passage along needle 106, and the hollow shaft is shaped to define a tapered distal end. This tapered distal end is first advanced through the hole created by needle 106. The hole is enlarged when the gradually increasing diameter of the distal end of the dilator is pushed through the hole in the septum.

Figure 2E:
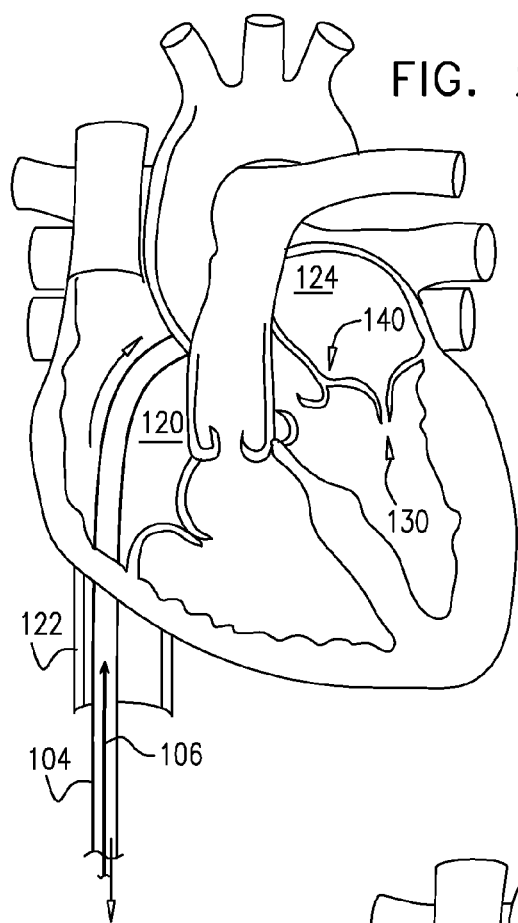

The advancement of sheath 104 through the septum and into the left atrium is followed by the extraction of the dilator and needle 106 from within sheath 104, as shown in FIG. 2E.

Figure 2F:
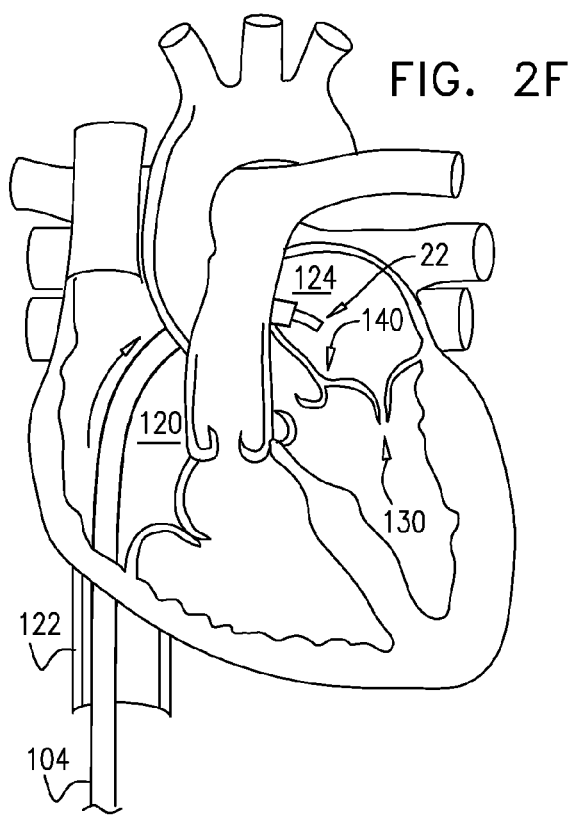
Figure 2G:
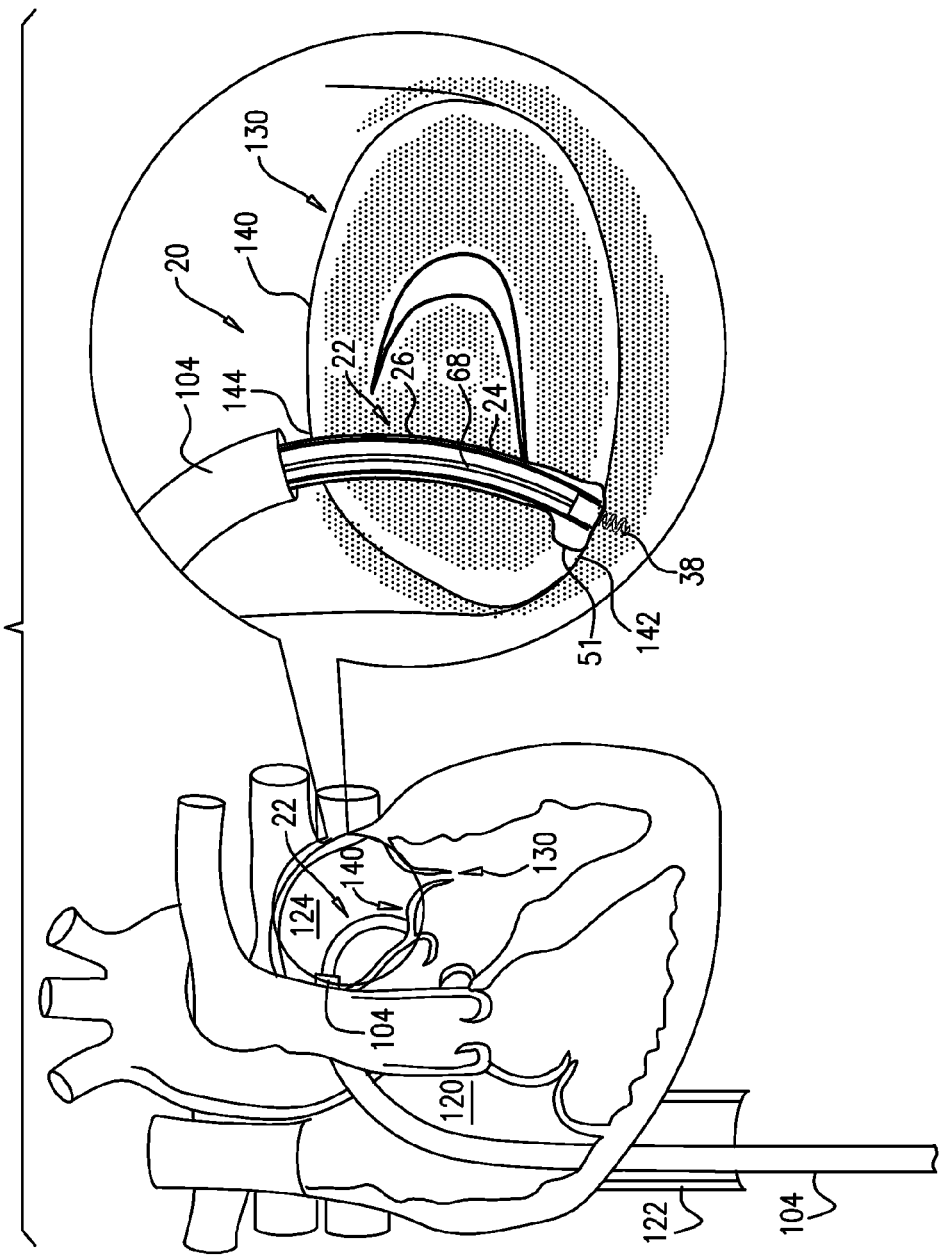

As shown in FIG. 2F, implantable structure 22 (with anchor deployment manipulator 24 therein) is advanced through sheath 104 into left atrium 124.

As shown in FIG. 2G, distal end 51 of sleeve 26 is positioned in a vicinity of a left fibrous trigone 142 of an annulus 140 of mitral valve 130. (It is noted that for clarity of illustration, distal end 51 of sleeve 26 is shown schematically in the cross-sectional view of the heart, although left trigone 142 is in reality not located in the shown cross-sectional plane, but rather out of the page closer to the viewer.) Alternatively, the distal end is positioned in a vicinity of a right fibrous trigone 144 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Still further alternatively, for some applications, the distal end is positioned along an anterior portion of the annulus, such as described hereinbelow with reference to FIG. 4. For some applications, outer tube 66 of anchor deployment manipulator 24 is steerable, as is known in the catheter art, while for other applications, a separate steerable tube is provided, such as described in the above-mentioned '604 publication, with reference to FIG. 15 and FIG. 16 thereof. In either case, the steering functionality typically allows the area near the distal end of the deployment manipulator to be positioned with six degrees of freedom. Once positioned at the desired site near the selected trigone, deployment manipulator 24 deploys a first anchor 38 through the wall of sleeve 26 into cardiac tissue near the trigone.

As shown in FIG. 2H, deployment manipulator 24 is repositioned along annulus 140 to another site selected for deployment of a second anchor 38. Typically, the first anchor is deployed most distally in the sleeve (generally at or within a few millimeters of the distal end of the sleeve), and each subsequent anchor is deployed more proximally, such that the sleeve is gradually pulled off (i.e., withdrawn from) the deployment manipulator in a distal direction during the anchoring procedure. The already-deployed first anchor 38 holds the anchored end of sleeve 26 in place, so that the sleeve is drawn from the site of the first anchor towards the site of the second anchor. Typically, as the sleeve is pulled off (i.e., withdrawn from) the deployment manipulator, the deployment manipulator is moved generally laterally along the cardiac tissue, as shown in FIG. 2H. Deployment manipulator 24 deploys the second anchor through the wall of the sleeve into cardiac tissue at the second site. Depending on the tension applied between the first and second anchor sites, the portion of sleeve 26 therebetween may remain tubular in shape, or may become flattened, which may help reduce any interference of the implantable structure with blood flow.

For some applications, in order to provide the second and subsequent anchors, anchor driver 68 is withdrawn from the subject's body via sheath 104 (typically while leaving outer tube 66 of the deployment manipulator in place in the sleeve), provided with an additional anchor, and then reintroduced into the subject's body and into the outer tube. Alternatively, the entire deployment manipulator, including the anchor driver, is removed from the body and subsequently reintroduced upon being provided with another anchor. Further alternatively, deployment manipulator 24 is configured to simultaneously hold a plurality of anchors, and to deploy them one at a time at the selected sites.

As shown in FIG. 2I, the deployment manipulator is repositioned along the annulus to additional sites, at which respective anchors are deployed, until the last anchor is deployed in a vicinity of right fibrous trigone 144 (or left fibrous trigone 142 if the anchoring began at the right trigone), thereby fastening sleeve 26 and implantable structure 22 to the annulus. Alternatively, the last anchor is not deployed in the vicinity of a trigone, but is instead deployed elsewhere in a vicinity of the mitral valve, such as in a vicinity of the anterior or posterior commissure.

For applications in which contracting mechanism 28 comprises spool 46, a rotation tool is typically used to rotate spool 46 of contracting mechanism 28, in order to tighten implantable structure 22. For some applications, the rotation tool is used that is described and shown in the above-mentioned '604 publication, with reference to FIGS. 6A-B, 7, and 8 thereof. As described therein, contracting mechanism 28 comprises longitudinal member 86 that is attached to the contracting mechanism and passes out of the body of the subject, typically via sheath 104. In order to readily bring the rotation tool to a driving interface of contracting mechanism 28, the rotation tool is guided over longitudinal member 86. For some applications, spool 46 is configured as described in the '604 publication with reference to FIGS. 1-4, 6A-B, 7, and/or 8 thereof.

Spool 46 typically comprises a locking mechanism that prevents rotation of the spool after contracting member 30 has been tightened. For example, locking techniques may be used that are described and shown in US Application Publication 2010/0161047, which is incorporated herein by reference, with reference to FIG. 4 thereof, and/or with reference to FIGS. 6B, 7, and 8 of the above-mentioned '604 publication. Alternatively, for some applications, contracting mechanism 28 is configured to tighten contracting member 30, crimp the contracting member to hold the contracting member taut, and subsequently cut the excess length of the contracting member.

For some applications, a rotation handle is used to tighten the implantable structure, such as described and shown in the above-mentioned '604 publication, with reference to FIGS. 9A-C and 10A-D thereof. As mentioned above, deploying the one or more anchors beyond the contracting portion of contracting member 30 generally distributes force applied by contraction of contracting assembly 40 over these anchors.

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 30.

For some applications, proximal end 49 of sleeve 26 is closed upon completion of the implantation procedure. Alternatively, the proximal end of the sleeve may have a natural tendency to close when not held open by deployment manipulator 24.

For some applications, following initial contraction of implantable structure 22 during the implantation procedure, the structure may be further contracted or relaxed at a later time after the initial implantation, such as between several weeks and several months after the initial implantation. Using real-time monitoring, tactile feedback and optionally in combination with fluoroscopic imaging, a rotation tool or anchor driver of a deployment manipulator may be reintroduced into the heart and used to contract or relax implantable structure 22.

Reference is now made to FIGS. 3 and 4, which are schematic illustrations of another configuration of implantable structure 22, in accordance with an application of the present invention. FIG. 3 shows implantable structure 22 in a straight, relaxed, non-contracted state, prior to implantation. FIG. 4 shows the implantable structure after implantation around the annulus of mitral valve 130, in accordance with an application of the present invention.

In this configuration, sleeve 26 is implanted in a closed loop. More particularly, a first portion 110 of sleeve 26 longitudinally extends from the first sleeve end (i.e., the end of the sleeve to which contracting mechanism 28, e.g., housing 44 thereof, is closest) toward contracting mechanism 28, e.g., housing 44 thereof (but typically does not extend all of the way to the contracting mechanism), and a second portion 112 of the sleeve longitudinally extends from the second sleeve end (i.e., the end of the sleeve to which second member end 53 is closest) toward second member end 53 (but typically does not extend all of the way to the second member end). As shown in FIG. 4, once implanted, sleeve 26 is arranged in a closed loop, such that first and second portions 110 and 112 of the sleeve together define a longitudinally overlapping portion 114 of the sleeve. The overlapping portion typically has a length of at least 2 mm (e.g., at least 5 mm), no more than 60 mm (e.g., no more than 50 mm), and/or between 2 mm (e.g., 5 mm) and 60 mm (e.g., 50 mm), and/or a length that is at least 1% of a total length of the sleeve, no more than 40% of the total length (e.g., no more than 30%), and/or between 1% and 40% (e.g., 30%) of the total length of the sleeve, measured when the sleeve is in a straight, relaxed, non-contracted state.

For some applications, at least one of tissue anchors 38 (labeled as 38E in FIGS. 3 and 4) penetrates both first and second portions 110 and 112 of the sleeve at overlapping portion 114. Such a mutual anchor helps ensure that the first and second portions remain tightly coupled together and to the tissue, so that the sleeve retains its closed loop shape. For some applications in which tissue anchor 38E comprises a coupling head and a tissue coupling element, such as described hereinbelow with reference to FIG. 5D, 5E, 5F, 5G, or 5I, the tissue coupling element penetrates both first and second portions 110 and 112 of the sleeve at overlapping portion 114, and the coupling head is positioned within one of first and second portions 110 and 112 of the sleeve at the overlapping portion. For example, in the deployment configuration shown in FIG. 4, the coupling head of anchor 38E is positioned within second portion 112.

This configuration of implantable structure 22 may be implanted using the procedure described hereinabove with reference to FIGS. 2A-I, with the following differences. Unlike in the deployment shown in FIGS. 2G-I, in this configuration sleeve 26 is deployed as a closed band around the entire annulus of the native valve, including an anterior portion 116 of the annulus (on the aortic side of the valve) between fibrous trigones 142 and 144. Typically, both first and second portions 110 and 112 of sleeve 26 (and thus overlapping portion 114) are positioned along anterior portion 116 of the annulus.

For some applications, during the implantation procedure, the first sleeve end (i.e., the end of the sleeve to which contracting mechanism 28, e.g., housing 44 thereof, is closest) is placed along at least a portion of anterior portion 116 and first portion 110 is extended along this portion. At least one anchor 38D is deployed through the wall of first portion 110 of sleeve 26 into cardiac tissue at the anterior portion of the annulus. Additional anchors 38A and/or 38C are deployed through the wall of the sleeve around the non-anterior remainder of the annulus, including the posterior portion thereof, as described hereinabove with reference to FIG. 2H. (Anchors 38C, if provided, are deployed beyond the ends of the contracting portion of contracting member 30, while anchors 38A are deployed along the portion of the sleeve including the contracting portion of the contracting member.)

A portion of the sleeve is placed on at least a portion of anterior portion 116 of the annulus, and, typically, one or more anchors 38B are deployed through the wall of the sleeve into tissue at the anterior portion of the annulus.

The sleeve is further extended around the annulus until second portion 112 overlaps with previously-deployed first portion 110 at overlapping portion 114, forming a complete ring. At least one anchor 38E is deployed from within second portion 112 through the wall of the sleeve and into the cardiac tissue, typically at anterior portion 116 of the annulus, or at a portion of the annulus near anterior portion 116. Typically, anchor 38E is deployed such that it additionally passes through previously-deployed first portion 110 (passing through the wall of first portion 110 twice). (Optionally, anchors 38B and/or 38E are of a different configuration than anchors 38A, 38C, and/or 38D, such as described hereinbelow with reference to FIGS. 5A-I; anchors 38B and 38E may be of the same configuration as one another, or of different configurations.)

Alternatively, the second sleeve end (i.e., the end of the sleeve to which second member end 53 is closest) is first placed at least partially along anterior portion 116, in which case second portion 112 is deployed before first portion 110, and anchor 38E is deployed from within first portion 110.

The sleeve may be deployed in either a clockwise direction or a counterclockwise direction, as viewed from the atrium.

Contracting assembly 40 is actuated, e.g., the rotatable structure of contracting mechanism 28 is rotated, in order to tighten implantable structure 22, as described hereinabove with reference to FIG. 2I. Typically, contracting member 30 does not extend along the portion of sleeve 26 deployed along anterior portion 116 of the annulus, and thus does not extend along first portion 110, second portion 112, or overlapping portion 114 of sleeve 26. The portion of the sleeve deployed along anterior portion 116 of the annulus (between the trigones) is thus non-contractible. For some applications, contracting member 30 is positioned along a non-anterior portion of the annulus, which non-anterior portion does not reach either of the fibrous trigones, e.g., does not reach within 5 mm of either of the trigones. Tightening of implantable structure 22 therefore tightens at least a portion of the posterior portion of the annulus, while preserving the length of anterior portion 116 of the annulus. (The anterior portion of the annulus should generally not be contracted because its tissue is part of the skeleton of the heart). However, the portion of the sleeve deployed along the anterior portion of the annulus prevents dilation of the anterior annulus, because the sleeve is anchored at both ends of the anterior annulus, and, as mentioned above, the sleeve typically comprises a longitudinally non-extensible material. This deployment configuration may help prevent long-term resizing of the anterior annulus, which sometimes occurs after implantation of partial annuloplasty rings, such as C-bands.

For some applications, the non-contractible portion of sleeve 26 (the portion without contracting member 30) extends somewhat beyond one or both of trigones 142 or 144 (in the posterior direction, away from anterior portion 116 of the annulus), such as up to 20 mm, such as up to 10 mm. In general, since the non-contractible portions of the sleeve are preset, the surgeon is able to decide during the implantation procedure the lengths of the anterior non-contractible area and the posterior contractible area, by selecting the length of overlapping portion 114. The greater the length of overlapping portion 114, the greater the relative length of the posterior contractible portion, and the lesser the relative length of the non-contractible portion.

For some applications, at least one anchor 38C is coupled to cardiac tissue on the posterior side of right fibrous trigone 144, between the trigone and the end of contracting member 30. Similarly, at least one anchor 38C may be coupled to cardiac tissue on the posterior side of left fibrous trigone 142, between the trigone and the other end of contracting member 30 (which, for some applications, is coupled to contracting mechanism 28, as shown in FIG. 4).

For some applications, at least one (either one or both) of first and second longitudinal distances D1 and D2 (described hereinabove with reference to FIG. 1), taken separately, is greater than 40 mm, such as greater than 60 mm. This sleeve portion(s) beyond the contracting portion of contracting member 30 provide the non-contractible portion of the sleeve positioned along anterior portion 116 of the annulus, and, optionally, the non-contractible portion(s) that extend beyond the anterior portion.

Reference is still made to FIGS. 3 and 4, and is additionally made to FIGS. 5A-I, which are schematic illustrations of different configurations of anchors 38, in accordance with respective applications of the present invention. For some applications, anchors 38 deployed along anterior portion 116 of the annulus (between the trigones) are of a different configuration from anchors 38 deployed along the remainder of the annulus (including the posterior portion of the annulus). Unlike the remainder of the annulus, anterior portion 116 does not comprise muscular or fibrous tissue, but rather thinner aortic tissue (typically the anchors positioned along anterior portion 116 enter the aorta below the aortic leaflets). The anchors that are deployed along the remainder of the annulus are configured for strong coupling to the thicker and stronger fibrous tissue of these portions of the annulus. Such anchors may be inappropriate for coupling to anterior portion 116. Anchors 38 are thus provided that are particularly configured for coupling to anterior portion 116.

For these applications, anchors 38 include a plurality of first tissue anchors of a first configuration, and a plurality of second tissue anchors of a second configuration different from the first configuration. (The first tissue anchors are labeled 38A and 38C in FIG. 4, and for the sake of brevity, are referenced as 38A hereinbelow. The second tissue anchors are labeled 38B, 38D, and 38E in FIG. 4, and for the save of brevity, are referenced as 38B hereinbelow). For some applications, implantable structure 22 comprises more first tissue anchors 38A than second tissue anchors 38B, e.g., at least twice as many first tissue anchors as second tissue anchors.

For these applications, sleeve 26 is typically arranged as a loop. For example, as described hereinabove with reference to FIG. 4, the sleeve may be shaped so as to define first and second sleeve ends, which are coupled to each other (optionally, with overlapping portion 114) to form the loop. Alternatively, as described hereinbelow with reference to FIG. 6, the sleeve may shaped so as to define an integrally closed loop having no sleeve ends. First tissue anchors 38A are coupled to sleeve 26 at intervals along a first longitudinally-contiguous portion of the loop, and second tissue anchors 38B are coupled to sleeve 26 at intervals along a second longitudinally-contiguous portion of the loop different from the first longitudinally-contiguous portion. The second portion of the loop is deployed along anterior portion 116 of the annulus, and the first portion of the loop is deployed along at least a portion of the remainder of the annulus (including the posterior portion of the annulus).

Reference is made to FIGS. 5A-C, which are schematic illustrations of an exemplary configuration of one of anchors 38A, in accordance with an application of the present invention. For some applications, each of first tissue anchors 38A comprises a helical tissue coupling element 200, and a tool-engaging head 202, fixed to one end of the tissue coupling element (the proximal end of the tissue coupling element, opposite the distal end that first penetrates the tissue). Anchor 38A comprises a hard material, such as metal, e.g., steel, Nitinol, or stainless steel SS316LVM. Anchor 38A may be manufactured from a single piece of material, or coupling element 200 and tool-engaging head 202 may be manufactured from separate pieces of material and fixed together.

Typically, helical tissue coupling element 200 has an inner diameter D3 of at least 1.5 mm, no greater than 2.5 mm, and/or between 1.5 and 2.5 mm, e.g., 1.8 mm, along an entire length thereof along a central longitudinal axis 210 of the anchor (although the inner diameter is shown as being constant along the entire length of coupling element 200, the inner diameter optionally varies along the length of the coupling element). An outer diameter D4 of helical tissue coupling element 200 may be, for example, at least 2.4 mm, no greater than 5 mm, and/or between 2.4 and 5 mm, e.g., 2.4 mm.

Tool-engaging head 202 is shaped so as to define an engaging opening 212 that passes entirely through the tool-engaging head along axis 210. The engaging opening is typically at least partially non-circular, such as in order to engage a rotating deployment element of a deployment tool. For example, as shown in FIGS. 5A-C, engaging opening 212 may be shaped so as to define a proximal non-circular internal engaging surface 220, and a distal circular non-engaging surface 222. Proximal engaging surface 220 is shaped to engage a rotating deployment element, such that rotation of the deployment element rotates tool-engaging head 202 and anchor 38A. For example, proximal engaging surface 220 may be rectangular (e.g., square), teethed (e.g., defining a plurality of squares with which the rotating element can engage), star-shaped, polygonal (e.g., octagonal), or any other appropriate non-circular shape.

A portion of the deployment element may pass partially or completely through distal non-engaging surface 222, without engaging this surface. The non-engaging surface may serve as a shoulder, which pushes against the tissue, providing resistance when the anchor has been sufficiently screwed into the tissue. Optionally, the deployment element does not pass entirely through distal non-engaging surface 222, such that the deployment element does not press against or into the tissue. Alternatively, the deployment element may protrude slightly from the distal non-engaging surface 222, when no force is applied to the deployment element by the tissue. Optionally, when the anchor is pressed against the tissue, inner spaces in the tool-engagement head 202 of the anchor allow the deployment element to sink into the anchor, and not press against the tissue. Engaging opening 212 typically has a cross-sectional area (perpendicular to axis 210) of at least 0.8 mm2, such as at least 1.2 mm2.

For some applications, a proximal-most portion 224 of helical tissue coupling element 200, at the end which is fixed to tool-engaging head 202, is generally straight and oriented generally parallel to axis 210, i.e., at angle of between 0 and 15 degrees with the axis, such as 0 degrees. Proximal-most portion 224 typically has a length of between 0.5 and 2 mm, such as about 1 mm.

The outer perimeter of tool-engaging head 202 is typically circular, and an outer diameter D5 of tool-engaging head 202 may be, for example, at least 2 mm, no greater than 7 mm, and/or between 2 and 7 mm, such as between 2.5 and 5 mm, e.g., 2.4 mm, 2.5 mm, or 3 mm.

The outer diameter of anchor 38A may be, for example, at least 2 mm, no greater than 7 mm, and/or between 2 and 7 mm, such as between 2.5 and 5 mm. The entire length of anchor 38A, measured along axis 210, is typically at least 2.5 mm, no greater than 10 mm, and/or between 2.5 and 10 mm, such as between 3 and 4.5 mm. A length L1 of tissue coupling element 200, measured along axis 210, may be at least 2.5 mm, no greater than 10 mm, and/or between 2.5 and 10 mm, such as between 3 and 4.5 mm. Typically, helical tissue coupling element 200 has between 3 and 5 turns.

The proximal end of tissue coupling element 200 is typically fixed to tool-engaging head 202 near the outer perimeter of the tool-engaging head, such that the tissue coupling element does not block engaging opening 212. For example, as labeled in the top-view of the anchor in FIG. 5C, the tissue coupling element may be fixed to the tool-engaging head such that one or more of the following dimension characterize the anchor:

a distance D7 between (a) a center 226 of the proximal end of tissue coupling element 200 and (b) an outer perimeter of tool-engaging head 202 is no greater than 20% of a width D5 of tool-engaging head 202 (the width is a diameter for applications in which the head is circular), such as no greater than 10% of width D3. For example, distance D7 may be between 0.1 and 0.3 mm, e.g., 0.2 mm;

a distance D8 between (a) a most radially-inward portion 228 of the proximal end of tissue coupling element 200 (i.e., the portion of the proximal end that is closest to central longitudinal axis 210 of the anchor) and (b) the outer perimeter of tool-engaging head 202 is no greater than 40% of width D5 of tool-engaging head 202 (the width is a diameter for applications in which the head is circular), such as no greater than 30% of width D5, or no greater than 20% of width D5. For example, distance D8 may be between 0.3 and 0.5 mm, e.g., 0.4 mm; and/or a distance between (a) a most radially-outward portion 230 of the proximal end of tissue coupling element 200 (i.e., the portion of the proximal end that is furthest from central longitudinal axis 210 of the anchor) and (b) the outer perimeter of tool-engaging head 202 is no greater than 10% of width D5 of tool-engaging head 202 (the width is a diameter for applications in which the head is circular), such as no greater than 5% of width D5, e.g., 0. For example, the distance may be between 0 and 0.1 mm, e.g., 0 mm.

Anchor 38A, including both helical tissue coupling element 200 and tool-engaging head 202, is thus shaped so as to provide a channel along the entire length of the anchor, through which a flexible inner shaft can pass, and through which a rotating deployment element can pass when in its radially-compressed state. More generally, as shown in FIG. 5B, the channel is sized and shaped such that a right circular cylinder 232 could be placed within the channel, coaxial with anchor 38A (i.e., the axis of the cylinder coincides with central longitudinal axis 210 of anchor 38A), and along the entire length of the tissue anchor, the cylinder having a diameter D6 of at least 1 mm, such as at least 2 mm. It is to be understood that cylinder 232 is an abstract geometric shape, rather than an element of an embodiment of the invention, and, as such, is perfectly cylindrical, i.e., is not shaped so as to define any grooves or other surface or internal anomalies. No portion of anchor 38A intersects central longitudinal axis 210.

Reference is made to FIG. 5D, which is a schematic illustration of a configuration of one of second tissue anchors 38B, in accordance with an application of the present invention. In this configuration, second tissue anchor 38B may be generally similar to first tissue anchor 38A (e.g., as described hereinabove with reference to FIGS. 5A-C), except that second tissue anchor 38B differs from first tissue anchor 38A in size. For example, second tissue anchor 38B may be smaller than first tissue anchor 38A. Typically, a length L2 of tissue coupling element 200 of second tissue anchor 38B, measured along axis 210, is less than length L1 of tissue coupling element 200 of first tissue anchor 38A. For example, length L2 may be between 25% and 75% of length L1, and/or at least 2 mm, no more than 6 mm, and/or between 2 and 6 mm, such as at least 2 mm, no more than 4 mm, and/or between 2 and 4 mm. Alternatively or additionally, helical tissue coupling element 200 of second tissue anchor 38B has fewer turns than does helical tissue coupling element 200 of first tissue anchor 38A. For some applications, helical tissue coupling element 200 of second tissue anchor 38B has between 25% and 75% of the turns of helical tissue coupling element 200 of first tissue anchor 38B. For example, helical tissue coupling element 200 of second tissue anchor 38B may have at least one turn, no more than three turns, and/or between one and three turns.

For some applications, each of tissue coupling element 200 of first tissue anchor 38A and tissue coupling element 200 of second tissue anchor 38B is shaped so as to define a shape selected from the group consisting of: a helix, a spiral, and a screw shaft, and the lengths of the coupling elements are measured along a longitudinal axis of the shape. Alternatively or additionally, the tissue coupling element of second tissue anchor 38B has fewer turns than does the tissue coupling element of first tissue anchor 38A.

For some applications, such as when second tissue anchors 38B are helical, second tissue anchors 38B alternatively or additionally differ from first tissue anchors 38A in that tissue coupling elements 200 of second tissue anchors 38B are rectangular in cross-section, rather than circular, which may provide a greater tissue surface contact area. Alternatively or additionally, helical second tissue anchors 38B may be shaped so as to define barbs, such as described hereinbelow with reference to FIG. 5I, mutatis mutandis.

Reference is made to FIG. 5E, which is a schematic illustration of another configuration of one of second tissue anchors 38B, in accordance with an application of the present invention. In this configuration, each of tissue coupling elements 200 of second tissue anchors 38B is shaped similar to a harpoon 238, which is shaped so as to define a sharp tip 242 and plurality of spikes 244 (e.g., three) that extend toward tool-engaging head 202. Spikes 244 are flexible (for example, they may comprise Nitinol or another shape memory alloy). For some applications, spikes 244 are initially crimped straight within a bore of a needle (not shown); after the needle and spikes are inserted into the tissue, the needle is withdrawn, leaving the spikes to expand radially outward in the tissue, so as to assume the configuration shown in FIG. 5F. Typically, tissue coupling element 200 is coupled to tool-engaging head 202 by a shaft 246.

Reference is made to FIG. 5F, which is a schematic illustration of another configuration of one of second tissue anchors 38B, in accordance with an application of the present invention. In this configuration, each of tissue coupling elements 200 is shaped so as to define a plurality (e.g., three) spiked arms 248, which are coupled to tool-engaging head 202 by a shaft 280, and a sharp tip 249. Spiked arms 248 typically are flexible (for example, they may comprise Nitinol or another shape memory alloy). After the sharp tip and spiked arms are inserted into the tissue, the spikes expand radially outward and toward the tool-engaging head in the tissue, so as to assume the configuration shown in FIG. 5F.

Reference is made to FIG. 5G, which is a schematic illustration of another configuration of one of second tissue anchors 38B, in accordance with an application of the present invention. In this configuration, each of tissue coupling elements 200 is shaped so as to define a screw shank 282, which is coupled to tool-engaging head 202. Shank 282 is shaped so as to define a screw thread 284, and is typically tapered.

Figure 5H:
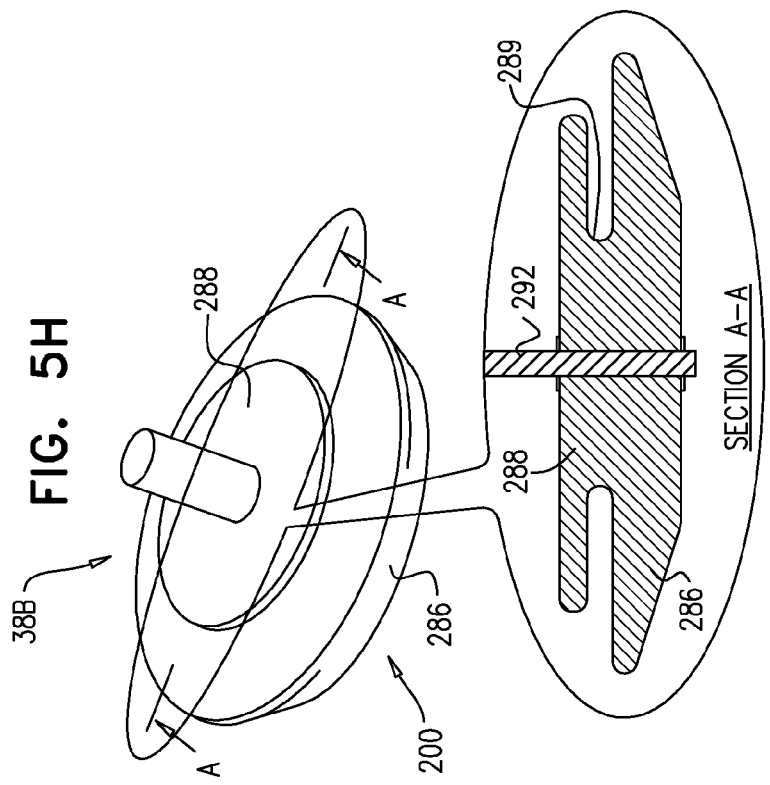

Reference is made to FIG. 5H, which is a schematic illustration of yet another configuration of one of second tissue anchors 38B, in accordance with an application of the present invention. In this configuration, each of tissue coupling elements 200 is shaped similar to a septal occluder, e.g., the Amplatzer® PFO Occluder (AGA Medical Corporation, Plymouth, Minn., USA). For example, tissue coupling element 200 may be similar to the configuration shown in FIGS. 12A-C of US Patent Application Publication 2009/0326648 to Machold et al., or FIGS. 21A-B of US Patent Application Publication 2010/0130992 to Machold et al., both of which publications are incorporated herein by reference. For some applications, tissue coupling element 200 comprises a mesh shaped into first and second discs 286 and 288, and a narrower waist section 289 between the two discs. The mesh may comprise wire, such as Nitinol, or a soft material, such as silicone. The wall of the sleeve and the tissue of the annuls are squeezed between the first and second discs, thereby anchoring the sleeve to the tissue.

Figure 5I:
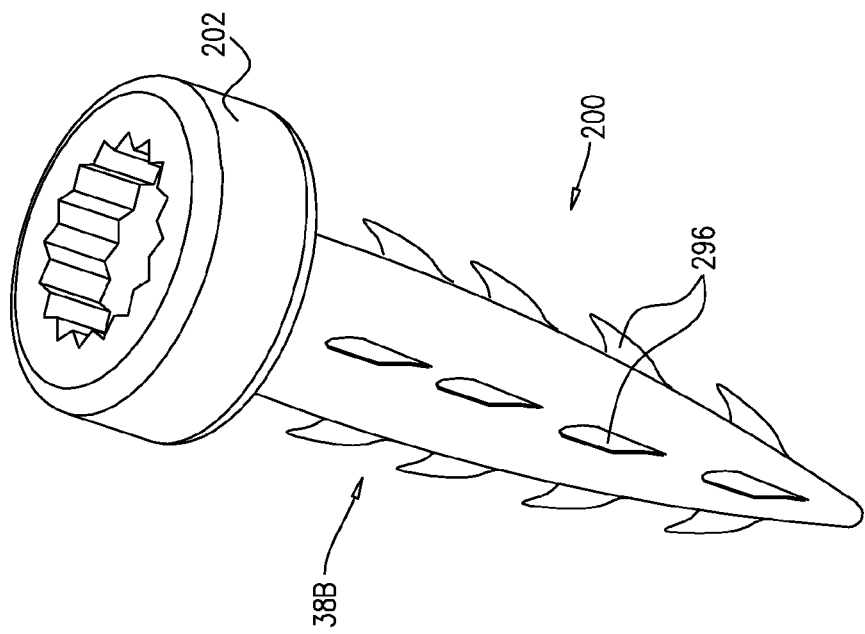

Reference is made to FIG. 5I, which is a schematic illustration of another configuration of one of second tissue anchors 38B, in accordance with an application of the present invention. In this configuration, each of tissue coupling elements 200 is shaped as a shaft 294 from which barbs 296 protrude radially outward and away from the tip of the tissue coupling elements.

For some applications, second tissue anchors 38B comprise sutures which are placed using a delivery tool.

Figure 6:
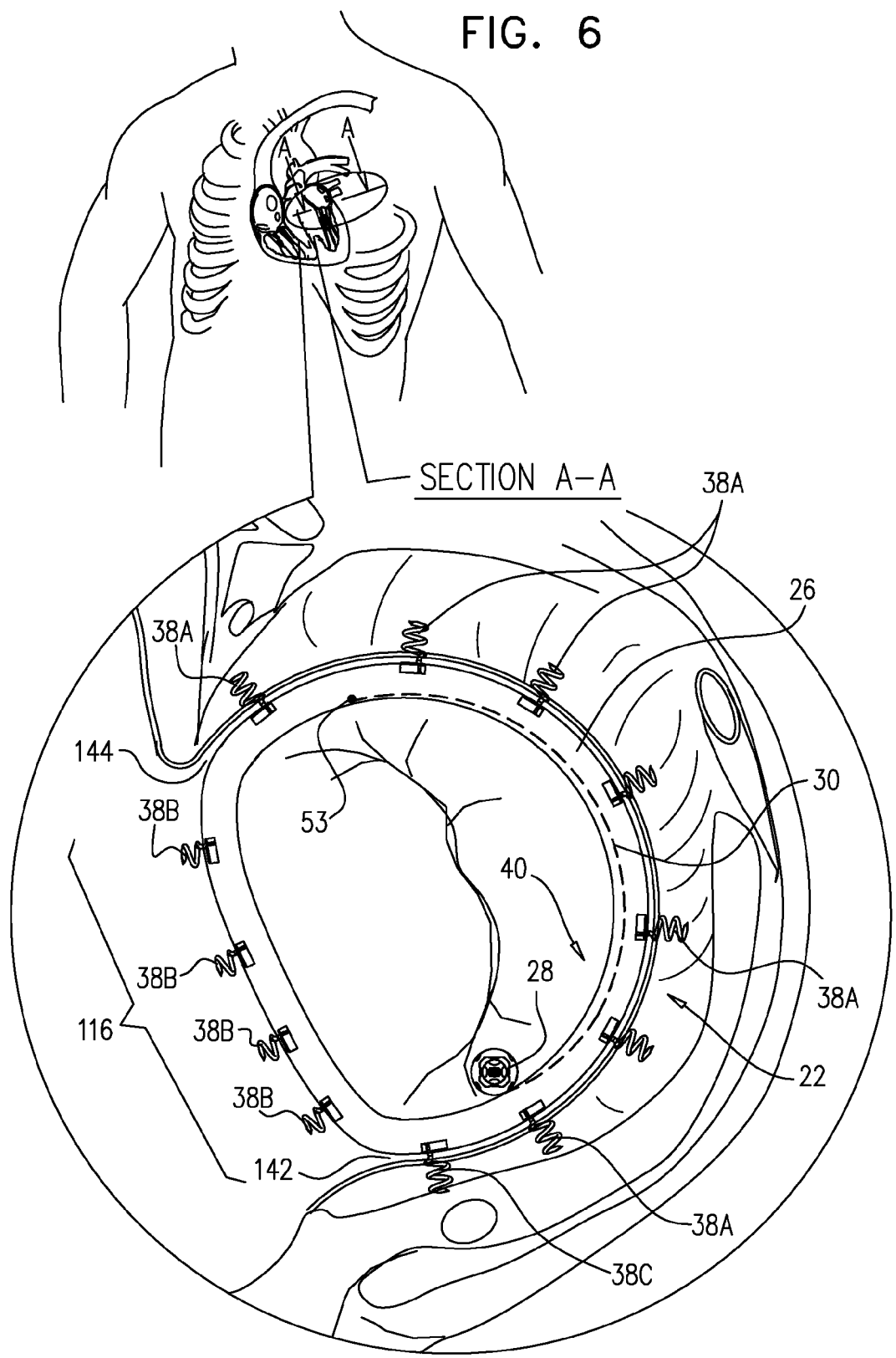
FIG. 6 is a schematic illustration of a closed-loop configuration of the implantable structure of FIG. 1, in accordance with an application of the present invention.

Reference is made to FIG. 6, which is a schematic illustration of an alternative closed-loop configuration of implantable structure 22, in accordance with an application of the present invention. In this configuration, flexible sleeve 26 is shaped so as to define an integrally closed loop having no sleeve ends. For some applications, anchors 38 deployed along anterior portion 116 of the annulus are of a different configuration from anchors 38 deployed along the remainder of the annulus, as described hereinabove with reference to FIGS. 3-4 and 5A-I. The anchors may be configured as described hereinabove with reference to FIGS. 5A-I.

Typically, contracting member 30 does not extend along the portion of sleeve 26 deployed along anterior portion 116 of the annulus. The portion of the sleeve deployed along anterior portion 116 of the annulus (between the trigones) is thus non-contractible. Tightening of implantable structure 22 therefore tightens at least a portion of the posterior portion of the annulus, while preserving the length of anterior portion 116 of the annulus. (The anterior portion of the annulus should generally not be contracted because its tissue is part of the skeleton of the heart). However, the portion of the sleeve deployed along the anterior portion of the annulus prevents dilation of the anterior annulus, because the sleeve is anchored at both ends of the anterior annulus, and, as mentioned above, the sleeve typically comprises a longitudinally non-extensible material. This deployment configuration may help prevent long-term resizing of the anterior annulus, which sometimes occurs after implantation of partial annuloplasty rings, such as C-bands.

For some applications, the non-contractible portion of sleeve 26 (the portion without contracting member 30) extends somewhat beyond one or both of trigones 142 or 144 (in the posterior direction, away from anterior portion 116 of the annulus), such as up to 20 mm, such as up to 10 mm.

For some applications, at least one anchor 38 is coupled to cardiac tissue on the posterior side of right fibrous trigone 144, between the trigone and the end of contracting member 30. Similarly, at least one anchor 38 may be coupled to cardiac tissue on the posterior side of left fibrous trigone 142, between the trigone and the other end of contracting member 30 (which, for some applications, is coupled to contracting mechanism 28, as shown in FIG. 6).

Figure 7:
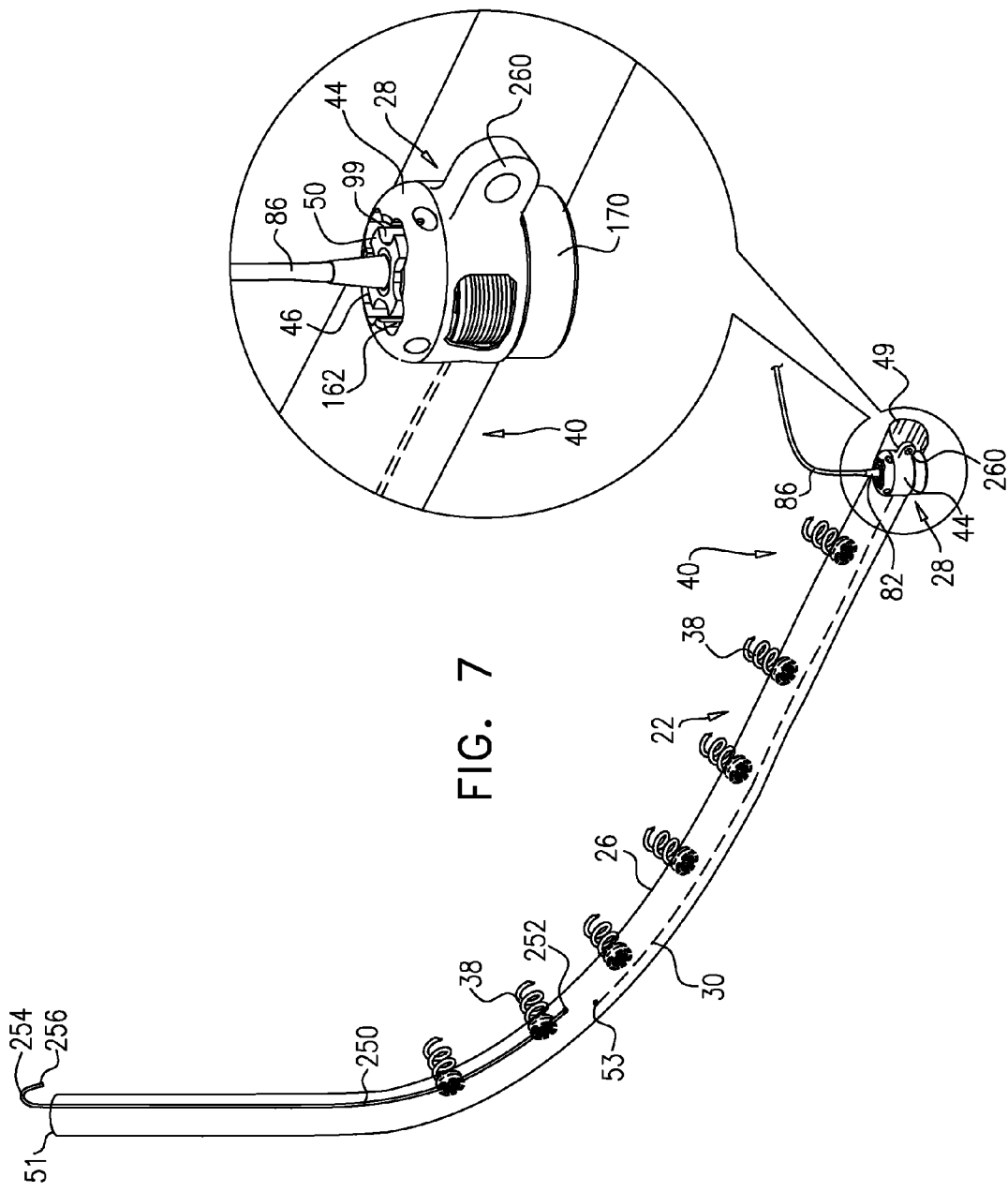
FIG. 7 is a schematic illustration of yet another configuration of the implantable structure of FIG. 1, prior to implantation, in accordance with an application of the present invention.
Figure 8:
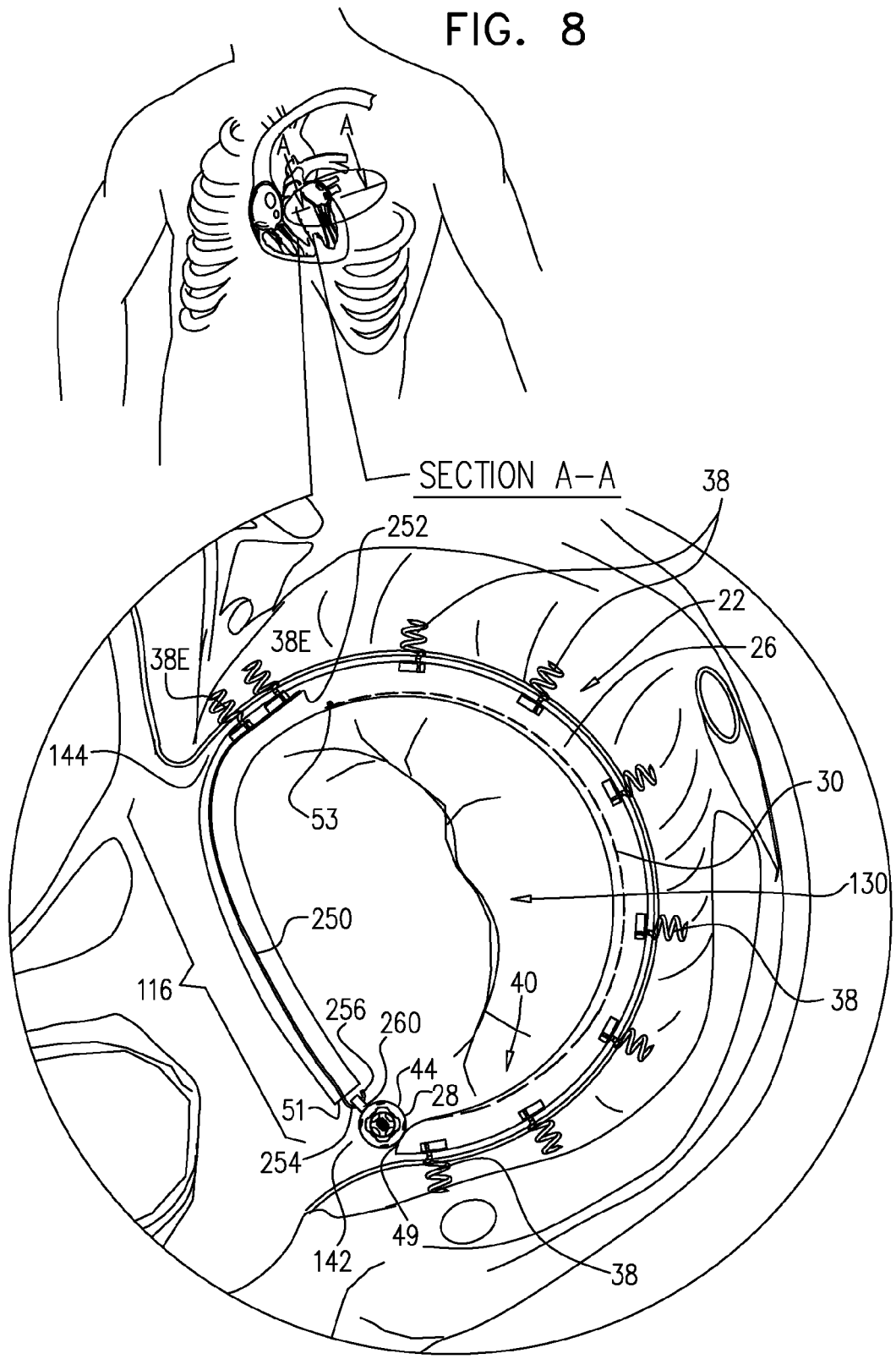
FIG. 8 is a schematic illustration of the implantable structure of FIG. 7 after implantation around the annulus of a mitral valve, in accordance with an application of the present invention.

Reference is now made to FIGS. 7 and 8, which are schematic illustrations of another configuration of implantable structure 22, in accordance with an application of the present invention. FIG. 7 shows implantable structure 22 in a relaxed, non-contracted state, and FIG. 8 shows the implantable structure implanted around mitral valve 130. This configuration of implantable structure 22 is generally similar to the configuration described hereinabove with reference to FIG. 1, except as follows. In this configuration, implantable structure 22 further comprises an elongated linking member 250, which is positioned at least partially along anterior portion 116 of the annulus, so as to join the ends of implantable structure 22 in a complete loop. Over time after implantation, linking member 250 becomes fixed to anterior portion 116 of the annulus, thereby helping prevent long-term dilation of the anterior annulus. Typically, at least a portion (e.g., at least 30%, such as at least 75% or at least 90%) of a length of linking member 250 is disposed within and covered by sleeve 26, into and/or over which fibrous tissue grows over time, helping anchor the linking member to tissue of the anterior annulus. Alternatively or additionally, a separate flexible sleeve or a coating (e.g., a polymeric coating) may be provided that covers at least 20%, e.g., between 20% and 80%, of the linking member. Typically, in the configuration of implantable structure 22 shown in FIGS. 7 and 8, none of anchors 38 is coupled to anterior portion 116 of the annulus.

Linking member 250 has first and second linking member ends 252 and 254. Second linking member end 254 comprises (e.g., is shaped so as to define, or is fixed to) a first coupling element 256. First linking member end 252 is disposed longitudinally between second linking member end 252 and a first sleeve end (either proximal end 49, as shown, or distal end 51, not shown), exclusive. Second linking member 254 either protrudes from the second end of the sleeve, or is recessed within the second end of the sleeve (as shown, the second end of the sleeve is distal end 51). A longitudinal portion of linking member 250 in a vicinity of first linking member end 252 is coupled to the sleeve. For example, the portion may be threaded through the fabric of the sleeve, and/or sewn (e.g., sutured) to the fabric of the sleeve to hold the linking member in place during deployment, and the linking member may be held in place after implantation by one or more of anchors 38. Optionally, the linking member is not initially coupled to the sleeve, but is instead held in place by a delivery tool during the implantation procedure, until being coupled to the sleeve by one or more of the anchors, for example. The coupled longitudinal portion may have a length of between 2 and 10 mm, and optionally includes first linking member end 252 of the linking member.

Implantable structure 22 further comprises a second coupling element 260, which is configured to be coupleable to first coupling element 256. Second coupling element 260 typically is coupled to implantable structure 22 within 1.5 cm of the first end of sleeve 26 (opposite the end mentioned above near which first linking member end 252 is fixed), measured when the sleeve is fully longitudinally extended. As mentioned above, in the configuration shown in FIGS. 7 and 8, this first end is proximal end 49.

For some applications, such as shown in FIGS. 7 and 8, contracting mechanism 28 (e.g., housing 44 thereof) is disposed along sleeve 26 within 1.5 cm of the first sleeve end (i.e., the same end of the sleeve near which the second coupling element is coupled). Second coupling element 260 may be coupled to contracting mechanism 28 (e.g., to housing 44). Alternatively, second coupling element 260 may be otherwise coupled to sleeve 26 (such as directly coupled), in which case contracting mechanism 28, e.g., housing 44 thereof, may be coupled to sleeve 26 at a greater longitudinal distance from the end of the sleeve, and one or more of anchors 38 may be coupled to the sleeve longitudinally between the contracting mechanism and the sleeve end, such as described hereinabove with reference to FIGS. 1, 2A-I, 3, and 4.

Typically, linking member 250 is substantially longitudinally non-extensible, i.e., its length is fixed. Typically, linking member 250 comprises metal, such as Nitinol or stainless steel. For some applications, the linking member has a length of at least 2 cm, no more than 6 cm, and/or between 2 and 6 cm.

For some applications, the linking member is configured as a spring, which is typically curved, so as to be elastic in a radial direction, i.e., to be compressible like a bow or deflected beam. In these applications, the linking member is oriented such that it is pressed by elasticity against the anterior portion of the mitral annulus, i.e., the outer wall of the aorta, thereby holding the sleeve covering the linking member against the aortic wall.

For some applications, at least two of tissue anchors 38 are coupled to sleeve 26 at respective, different longitudinal sites alongside linking member 250, within 6 cm of first linking member end 252, such as within 2 to 6 cm of the first end. These tissue anchors may help set the proper direction of curvature of the linking member, for applications in which the linking member is curved.

Reference is made to FIGS. 9A-B, which are schematic illustrations of coupling elements 256 and 260, in accordance with respective applications of the present invention. For some applications, at least one of first and second coupling elements 256 and 260 comprises a hook 270. Alternatively or additionally, for some applications, at least one of the first and second coupling elements comprises a loop 272. In the configuration shown in FIG. 9A (and FIGS. 7 and 8), first coupling element 256 comprises hook 270, and second coupling element 260 comprises a loop 272. In the configuration shown in FIG. 9B, both first and second coupling elements 256 and 260 comprises respective loops 272, and the coupling elements are coupled together such as by placing one of anchors 38 through both loops and into cardiac tissue.

Reference is now made to FIGS. 10A-E, which are schematic illustrations of a configuration of system 20 comprising a coiled element 240, in accordance with some applications of the present invention. Implantable structure 22 is generally similar to the configuration of implantable structure 22 described hereinabove with reference to FIGS. 3 and 4, or with reference to FIG. 6 or 7-9B, mutatis mutandis, with the exception that coiled element 240 is advanced within the lumen of sleeve 26 during the implantation procedure, as described hereinbelow, or is prepositioned in the sleeve prior to commencement of the implantation procedure. In this configuration, implantable structure 22 is typically configured to not contract the posterior portion of the annulus along the middle scallop (P2) of the posterior leaflet, and to contract portions of the annulus along (a) a lateral scallop (P1) of the posterior leaflet and extending to left fibrous trigone 142, and (b) the medial scallop (P3) of the posterior leaflet and extending to right fibrous trigone 144.

Implantable structure 22 is implanted along the annulus of the native mitral valve, such as described hereinabove with reference to FIGS. 2A-I, mutatis mutandis. During the implantation procedure, typically after deploying anchors 38, a contraction-restricting-element advancement tube 330 is advanced toward implantable structure 22 through a lumen of a delivery tube 332. It is to be noted that deployment manipulator 24 (shown in FIGS. 2G-I) may be advanced within delivery tube 332 during the anchoring of implantable structure 22 to the annulus. For some applications, advancement tube 330 may be slidable within sheath 104 (shown in FIGS. 2B-G).

As shown in FIG. 10A, advancement tube 330 is advanced within the lumen of sleeve 26 until approximately one of the fibrous trigones (e.g., right fibrous trigone 144, in the direction of implantation shown in FIG. 10A), generally in the vicinity of contracting mechanism 28, e.g., housing 44 thereof. Alternatively, advancement tube 330 is advanced to near the end of the sleeve, before the overlapping portion through which anchor 38E passes. For some applications, delivery tube 332 is also advanceable within the lumen of sleeve 26 (not shown for clarity of illustration).

Figure 10B:
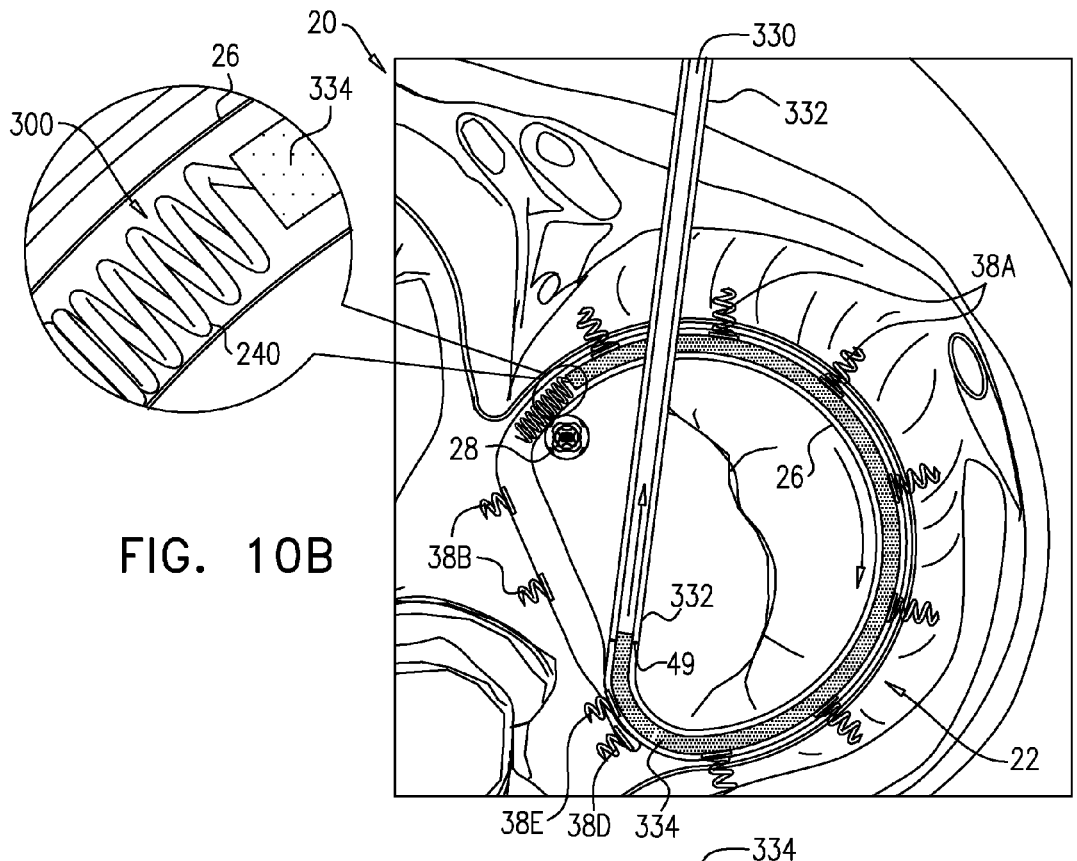

As shown in FIG. 10B, advancement tube 330 houses an overtube 334 which, in turn, houses coiled element 240. Coiled element 240 comprises a flexible material, e.g., Nitinol, which is biased to assume the coiled shape shown in FIG. 10C. For some applications in which the coiled element comprises such a flexible material, coiled element 240 is disposed within overtube 334 in a state in which coiled element 240 is generally straightened from its coiled state, i.e., at least partially uncoiled. In order to deploy element 240 within the lumen of sleeve 26, overtube 334 is retracted in the direction indicated by the arrow in FIG. 10B. For some applications, a pusher (not shown) disposed within overtube 334 proximally to element 240 pushes on element 240 as overtube 334 is retracted. During the deployment of coiled element 240, successive portions of element 240 are exposed from within overtube 334 and assume the pre-determined coiled configuration, as shown.

Figure 10C:
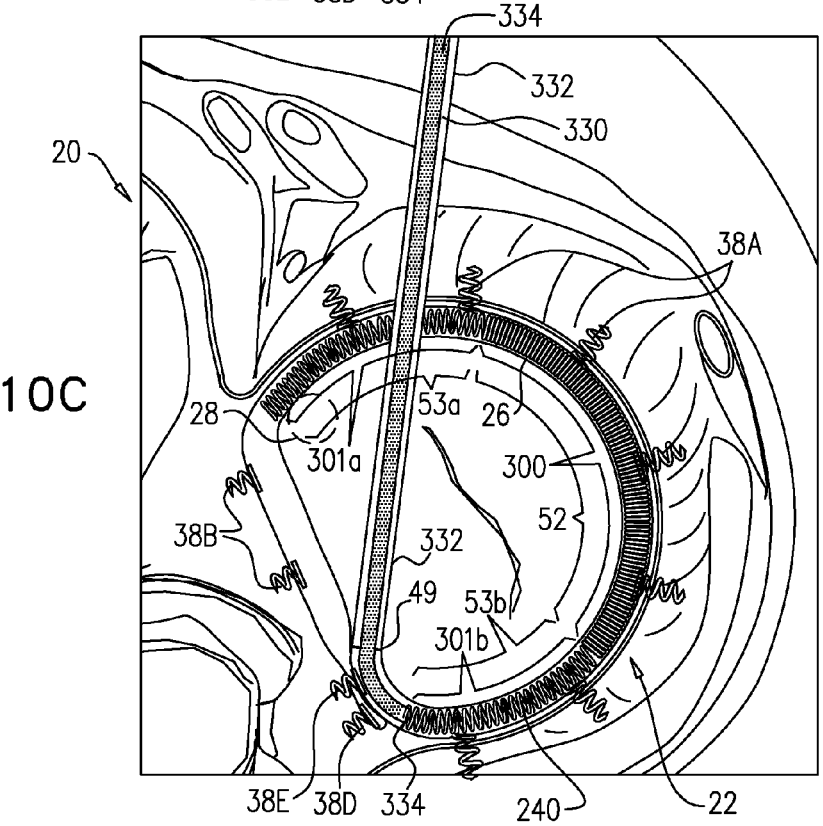

As shown in FIG. 10C, coiled element 240 is advanced within the lumen of sleeve 26 and comprises a contraction-restricting portion 300 and contractible portions 301a and 301b. In its deployed configuration, i.e., its coiled configuration, element 240 is typically shaped so as to define a diameter of between 2 and 6 mm, e.g., 3 mm.

Figure 10D:
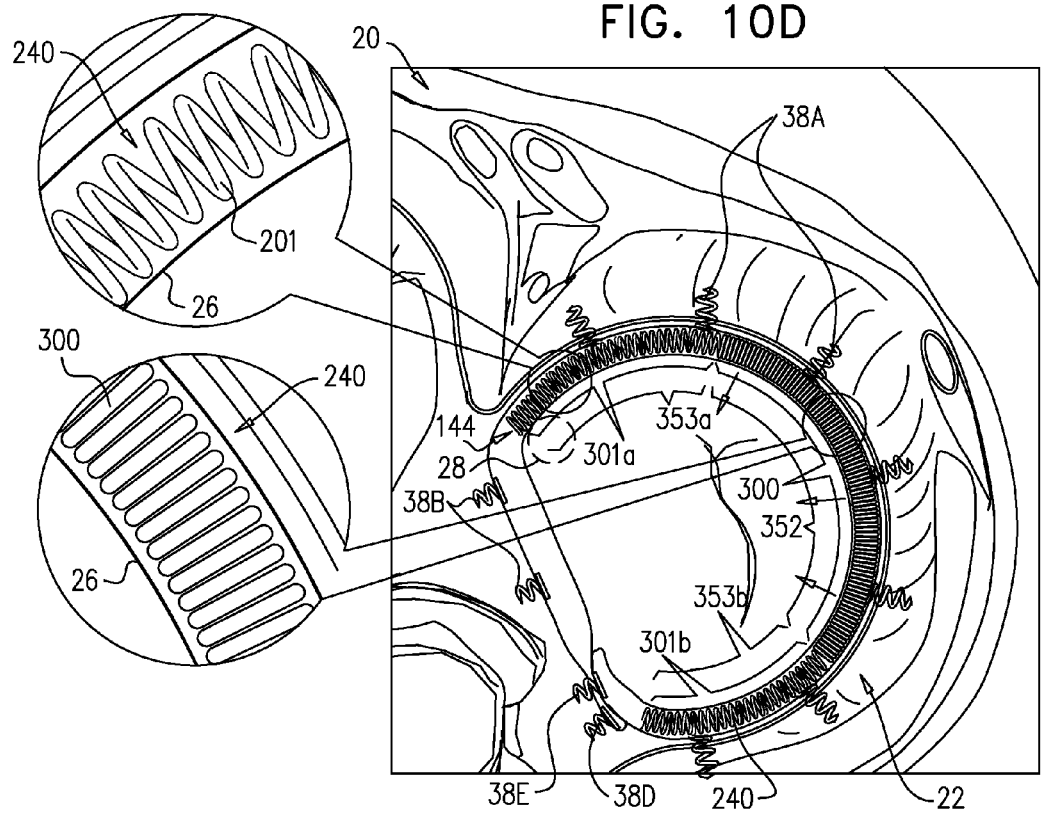

As shown in FIG. 10D, following the advancement of coiled element 240 within the lumen of sleeve 26, overtube 334, advancement tube 330, and delivery tube 332 are removed from within the body of the patient, and the opening at proximal end 49 of implantable structure 22 is typically closed, such as by closure mechanism 290, described hereinbelow with reference to FIGS. 16 and 17A-B.

As shown in FIGS. 10C-D, contraction-restricting portion 300 is a coiled portion of element 240 that is non-compressible, and contractible portions 301a and 301b (that are coupled to, or flank, contraction-restricting portion 300) are respective portions of element 240 that are compressible. Contraction-restricting portion 300 defines a pitch that is smaller than that of portions 301a and 301b (as shown in the blow-ups in FIG. 10D). Thus, if coiled element 240 were to be positioned along a longitudinal axis, contraction-restricting portion 300 would restrict contraction of element 240 (and thereby implantable structure 22) along the longitudinal axis, while contractible portions 301a and 301b would allow contraction of element 240 (and thereby implantable structure 22) along the longitudinal axis. When coiled element 240 is positioned within the lumen of sleeve 26, as shown in FIGS. 10C-D, (1) contraction-restricting portion 300 defines a contraction-restricted portion 352 of structure 22 that is disposed along the portion of the annulus at the posterior leaflet, and (2) contractible portions 301a and 301b define respective contractible portions 353a and 353b of structure 22 that are contractible and expandable in response to respective tightening or loosening of contracting member 30 (not shown for clarity of illustration) responsively to the actuation of contracting assembly 40. For some applications, contraction-restricting portion 300 has a length of more than 3 mm and/or less than 120 mm (e.g., a length of 3 mm-120 mm), and defines contraction-restricted portion 352, portion 352 having a length of more than 3 mm and/or less than 120 mm (e.g., a length of 3 mm-120 mm). During the ongoing contraction of structure 22 responsively to the actuation of contracting assembly 40, contractible portions 301a and 301b facilitate longitudinal contraction of portions 353a and 353b, respectively, while contraction-restricting portion 300 restricts longitudinal contraction of portion 352, but facilitates radial movement of portion 352 toward the center of the valve (i.e., in the direction as indicated by the arrows). This radial movement of portion 352 brings the posterior leaflet toward the anterior leaflet.

Figure 10E:
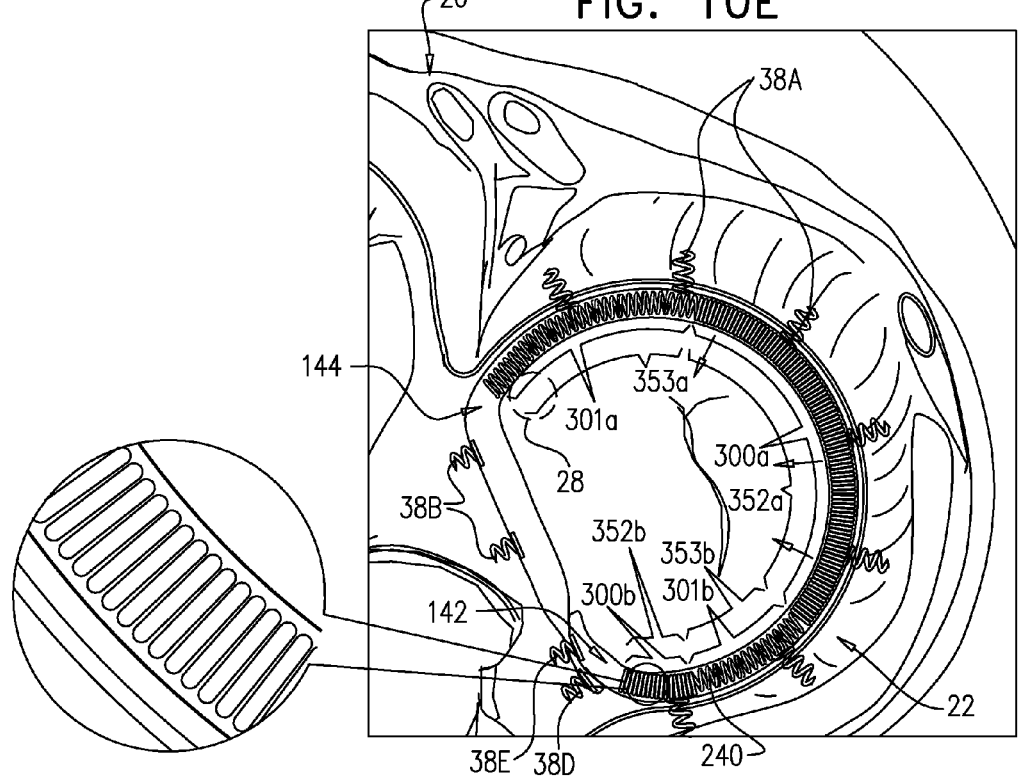

It is to be noted that one contraction-restricting portion 300 and two contractible portions 301a and 301b are shown in FIGS. 10A-D by way of illustration and not limitation, and that coiled element 240 may comprise any suitable number of portions 300 or 301. For example, in FIG. 10E coiled element 240 is shown defining two contraction-restricting portions 300a and 300b, and two contractible portions 301a and 301b. When coiled element 240 is positioned within the lumen of sleeve 26, as shown in FIG. 10E, (1) contraction-restricting portion 300a defines contraction-restricted portion 352a of structure 22 that is disposed along the portion of the annulus at the posterior leaflet, (2) contraction-restricting portion 300*b* defines contraction-restricted portion 352*b* of structure 22 that is disposed in a vicinity of trigone 142, and (3) contractible portions 301*a* and 301*b* define respective contractible portions 353*a* and 353*b* of structure 22 that are contractible and expandable in response to respective tightening or loosening of contracting member 30 (not shown for clarity of illustration) responsively to the actuation of contracting assembly 40. Typically, contraction-restricted portion 352*a* comprises more than 10% (e.g., more than 20%), and/or less than 60% (e.g., less than 30%) of the resting length of coiled element 240. For some applications, each of contractible portions 353*a* and 353*b* comprises less than 50% (e.g., less than 20%, or less than 10%) of the resting length of coiled element 240. For some applications, the total length of the contractible portions of coiled element 240 comprises less than 50%, e.g., less than 30%, of the resting length of the coiled element.

In the configuration shown in FIG. 10E, coiled element 240 defines two contraction-restricting portions 300*a* and 300*b*, one of which is disposed along the portion of the annulus at the posterior leaflet, and one of which is disposed in a vicinity of one of the trigones. However, the scope of the present invention includes configuration in which coiled element 240 defines three contraction-restricting portions 300, one of which is disposed along the portion of the annulus at the posterior leaflet, and two of which are disposed in vicinities of respective trigones of the subject. For some applications, coiled element 240 defines two contraction-restricting portions 300, which are disposed in vicinities of respective trigones of the subject.

For some applications, the implantable structures described herein are configured such that the contraction-restricted portions and the contractible portions of the implantable structures are disposed adjacent to respective portions of the mitral annulus, so as to facilitate reshaping of the mitral annulus in a desired manner. The lengths of the contraction-restricted portions and the contractible portions typically correspond to the corresponding portions of the mitral annulus. Typically, upon placement of the implantable structures described herein at the mitral annulus, contraction-restricted portions 352 and contractible portions 353 are asymmetrically disposed with respect to the mitral annulus. Further typically, lengths of the contraction-restricted portions and the contractible portions are not equal to one another. Alternatively, lengths of the contraction-restricted portions and the contractible portions are equal to one another.

Reference is again made to FIGS. 10A-E. It is to be noted that although system 20 is advanced and implanted within the heart of the patient using a minimally-invasive procedure, any suitable procedure may be used to advance and implant system 20, e.g., a transcatheter procedure or a surgical procedure, such as an open-heart surgical procedure.

Figure 11B:
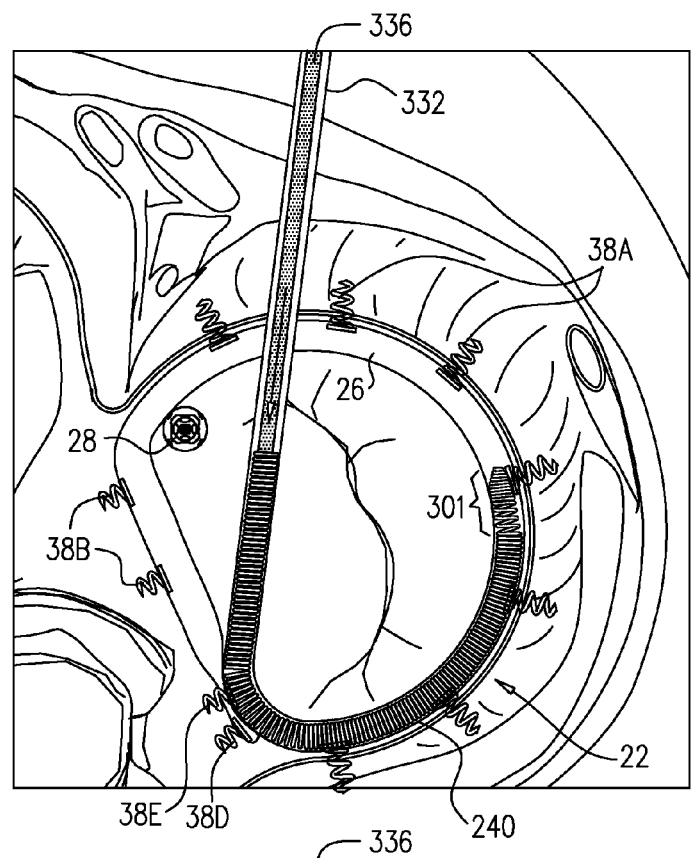
Figure 11C:
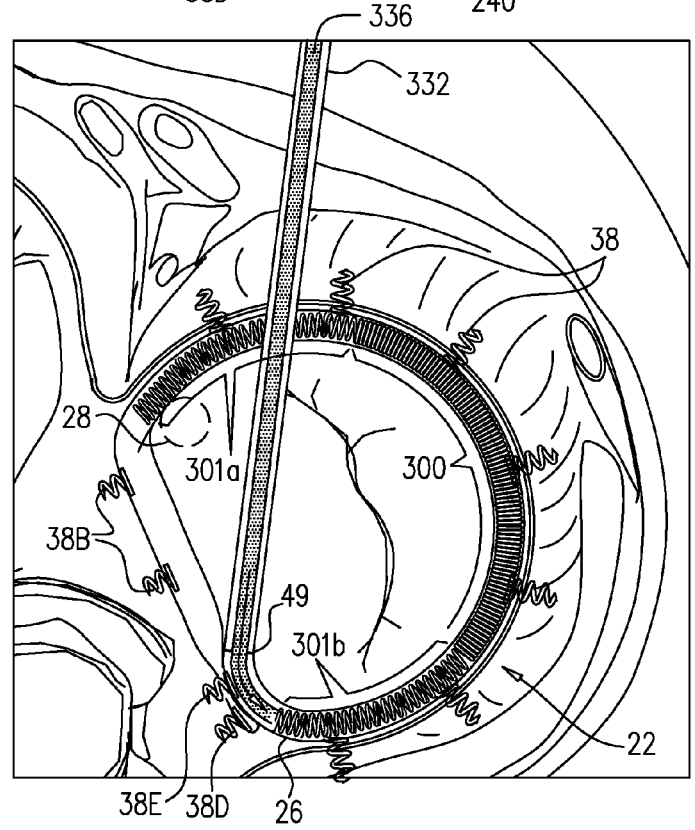

Reference is now made to FIGS. 11A-D, which are schematic illustrations of another configuration of system 20, in accordance with an application of the present invention. This configuration is similar to the configuration described hereinabove with reference to FIGS. 10A-E, with the exception that coiled element 240 is not advanced within overtube 334. Coiled element 240 is instead advanced directly within the lumen of delivery tube 332 and into the lumen of sleeve 26 in its coiled state, as shown in FIGS. 11A-C. Typically, a pushing tube 336 slides within delivery tube 332 proximally to coiled element 240 in order to push coiled element 240 from within the lumen of delivery tube 332. Typically, delivery tube 332 is advanced within the lumen of sleeve 26 until approximately one of the fibrous trigones (e.g., right fibrous trigone 144, in the direction of implantation shown in FIG. 11A), generally in the vicinity of contracting mechanism 28, e.g., housing 44 thereof. Alternatively, advancement tube 330 is advanced to near the end of the sleeve, before the overlapping portion through which anchor 38E passes, and coiled element 240 is positioned within the lumen of sleeve 26 when tube 332 is retracted and pushing tube 336 pushes on coiled element 240.

Figure 11E:
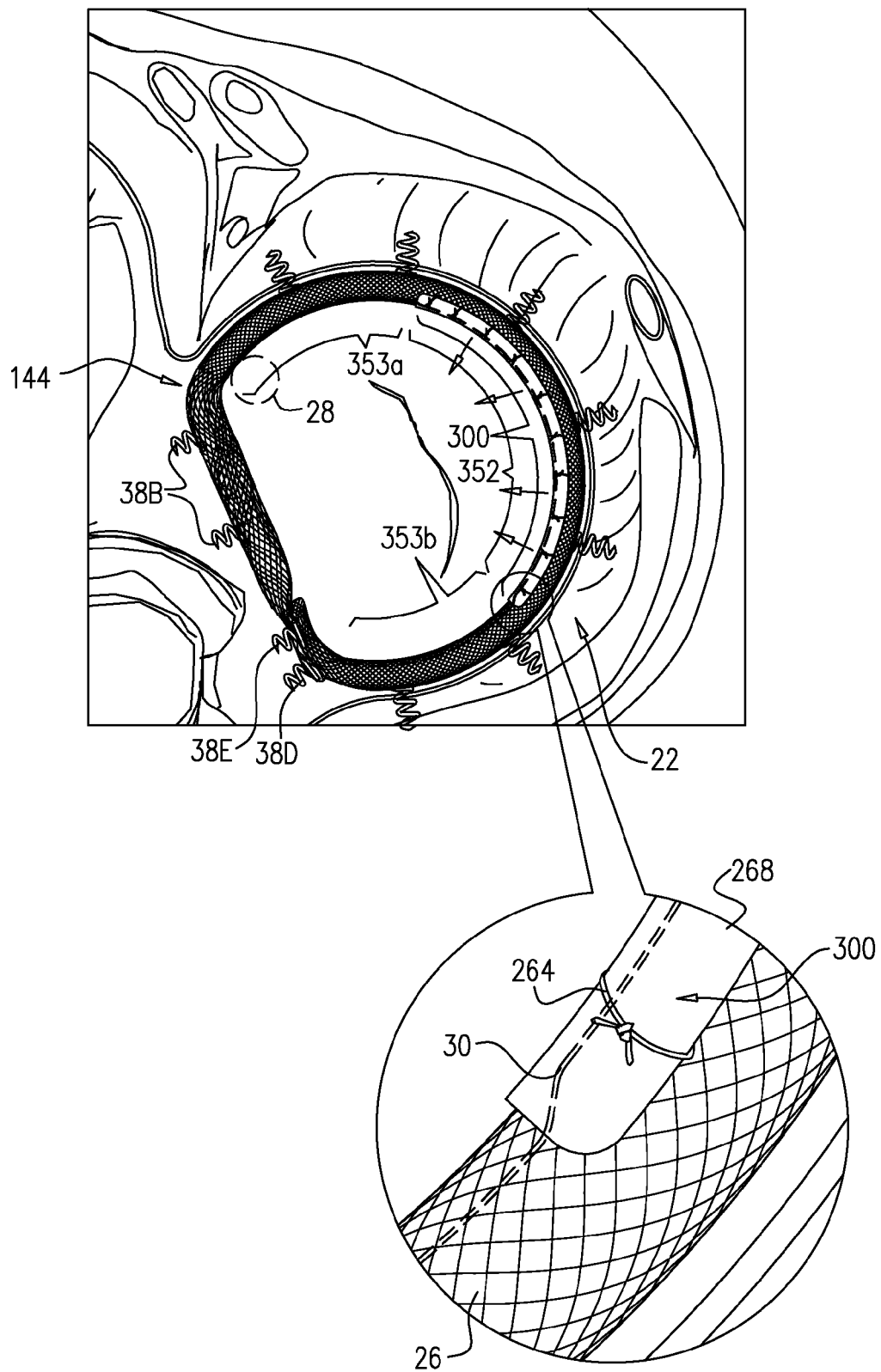

FIG. 11E is a schematic illustration of another configuration of system 20, in accordance with an application of the present invention. In this configuration, contraction-restricting portion 300 comprises a contraction-restricting segment 268 that is coupled to an outer surface of sleeve 26. For some applications, segment 268 comprises a coiled element, as described hereinabove. For other applications, segment 268 comprises a tubular element comprising a material, e.g., a semi-rigid material (such as Nitinol, polyethylene, and/or silicone, e.g., high-rigidity silicone), which restricts compression along a longitudinal axis of segment 268.

Typically, segment 268 is coupled to sleeve 26 by being sutured thereto via sutures 264, by way of illustration and not limitation, typically before implant 262 is advanced within the body of the patient. Segment 268 may be coupled to sleeve 26 using any suitable coupling technique. Segment 268 is typically coupled to sleeve 26 prior to advancing implant 262 within the body of the patient.

Segment 268 is typically coupled to portion of sleeve 26 designated for implantation along the annulus of the valve at the posterior leaflet. Alternatively or additionally, segment 268 is coupled to a portion of the sleeve designated for implantation in a vicinity of one or both trigones 144 and 142. The coupling of segment 268 to the portion of sleeve 26 defines contraction-restricted portion 352 of structure 262, while the remaining portions of sleeve 26 not coupled to segment 268 define contractible portions 353*a* and 353*b* of structure 262. In general, the techniques described hereinabove with respect to contraction-restricting portion 300, with reference to FIGS. 10A-12, may be applied to segment 268, mutatis mutandis.

Following the implantation of structure 262 along the annulus, portions of implantable structure 262 are contracted using contracting assembly 40, as described hereinabove. During the ongoing contraction of structure 262 responsively to the actuation of contracting assembly 40, contractible portions 353*a* and 353*b* are contracted, while contraction-restricting portion 300 restricts longitudinal contraction of contraction-restricted portion 352, but facilitates radial movement of portion 352 toward the center of the valve (i.e., in the direction as indicated by the arrows). This radial movement of portion 352 brings the posterior leaflet toward the anterior leaflet.

Following the contracting of structure 262 by mechanism 28, the opening at proximal end 49 of implantable structure 262 may be closed, such as by closure mechanism 290, described hereinbelow with reference to FIGS. 16 and 17A-B.

It is to be noted that although contraction-restricting segment 268 is shown in FIG. 11E as comprising a tubular element, for some applications, a different element, e.g., a suture, is used to define contraction-restricted portion 352 of implantable structure 262. For example, coiled element 240 may be placed inside sleeve 26. One or more contraction-restricting elements (e.g., a suture, a staple, a ratchet mechanism, and/or a bracket) are placed around portions of the coiled element, in order to decrease the pitch of the coiled element at the portions, thereby reducing the contractibility of the portions.

For some applications, a healthcare professional places the contraction-restricting element around given portions of the coiled element intra-procedurally, the portions of the coiled element corresponding to respective portions of a subject's mitral annulus. For example, subsequent to determining the size of the subject's mitral valve, and before placing the implantable structure inside the patient's body, the healthcare professional may place contraction-restricting element around given portions of the coiled element, in order to reduce the contractibility of the portions. For some applications, the healthcare professional applies sutures to the coiled element while the element is disposed inside the sizer. For some applications, the sizer is used to guide the suturing and to prevent the healthcare professional from placing a suture through contracting member 30.

Figure 12:
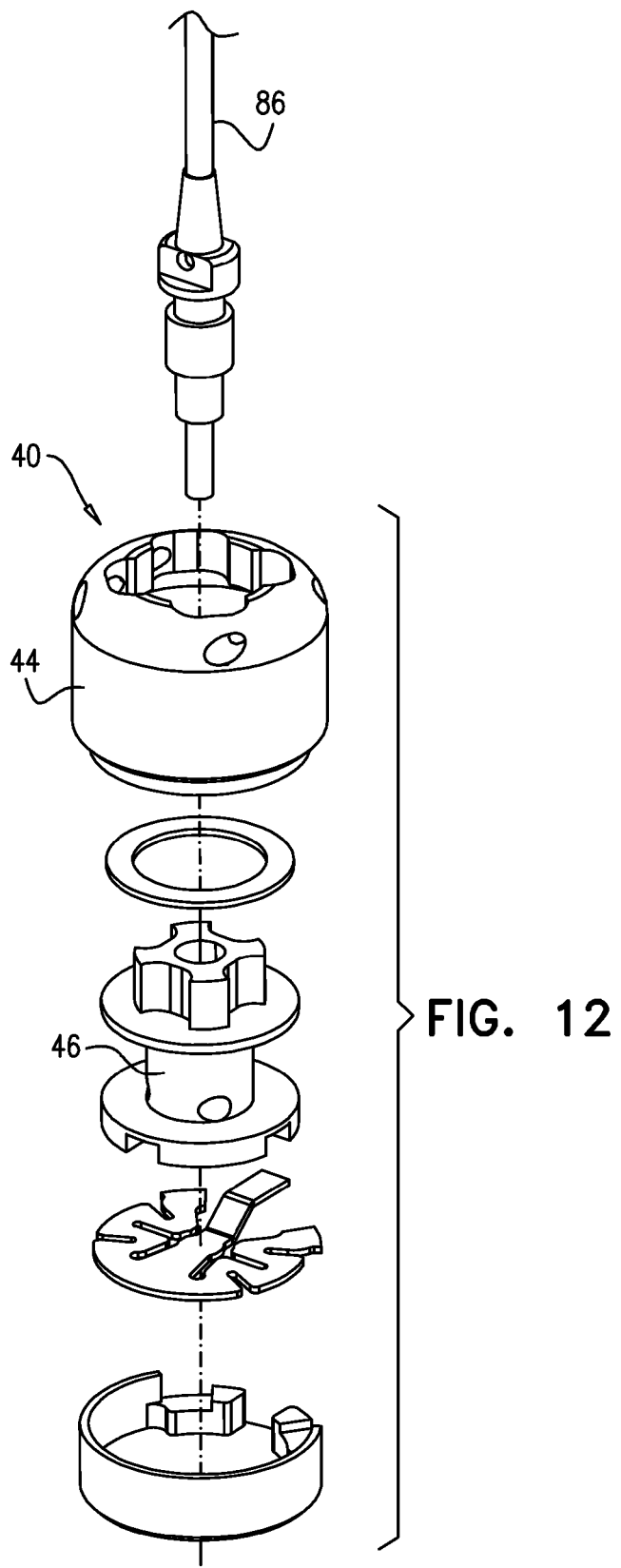
FIG. 12 is a schematic illustration of a contracting mechanism, disassembled to show a relationship among individual components of the contracting mechanism, in accordance with an application of the present invention.

Reference is now made to FIG. 12, which is a schematic illustration of contracting mechanism 28, disassembled to show a relationship among individual components of the contracting mechanism, in accordance with an application of the present invention. The components are arranged and function as described with reference to FIG. 7 of the above-mentioned '604 publication, mutatis mutandis.

Reference is now made to FIG. 13, which is a schematic illustration of another configuration of implantable structure 22, in accordance with an application of the present invention. This configuration of implantable structure 22 is generally similar to the configuration described hereinabove with reference to FIG. 1, except as follows. Contracting assembly 40 comprises first and second longitudinal contracting members 30A and 30B, having respective first member ends and respective second member ends 53A and 53B. Contracting members 30A and 30B have respective first and second member ends, and respective first member end portions, which extend from the respective first member ends toward the respective second member ends along only respective longitudinal portions of the contracting members. The first member end portions, e.g., the first member ends, are coupled to contracting mechanism 28, e.g., a rotatable structure, such as spool 46. Second member end 53A of first contracting member 30A is coupled to sleeve 26 at a first site 39A at a first longitudinal distance from the first sleeve end. Second member end 53B of second contracting member 30B is coupled to sleeve 26 at a second site 39B at a second longitudinal distance from the second sleeve end.

Contracting mechanism 28, e.g., the rotatable structure, such as spool 46, is positioned at an intermediary third site along the sleeve, longitudinally between first and second sites 39A and 39B, exclusive. For example, the contracting mechanism may be positioned a longitudinal distance from one of the ends of the sleeve, which longitudinal distance equals between 30% and 70% of the length of the sleeve. Contracting mechanism 28 and longitudinal members 30A and 30B are arranged to longitudinal contract the sleeve, for example, are arranged such that rotation of the rotatable structure longitudinally contracts the sleeve, such as by winding contracting members 30A and 30B around the spool, thereby contracting both of the longitudinal contracting members.

For some applications, at least one (either one or both) of the first and second longitudinal distances, taken separately, when measured when the sleeve is in a straight, relaxed, non-contracted state, is at least 3 mm, e.g., at least 5 mm, such as at least 9 mm, e.g., at least 14 mm. For some applications, each of the first and second longitudinal distances is at least 3 mm, e.g., at least 5 mm, such as at least 9 mm, e.g., at least 14 mm. For some application, one of the first and second longitudinal distances is at least 3 mm, such as at least 5 mm (e.g., at least 9 mm, or at least 14 mm), and the other of the first and second longitudinal distances is less than 5 mm, such as less than 3 mm, e.g., is equal to 0 mm.

Figure 15:
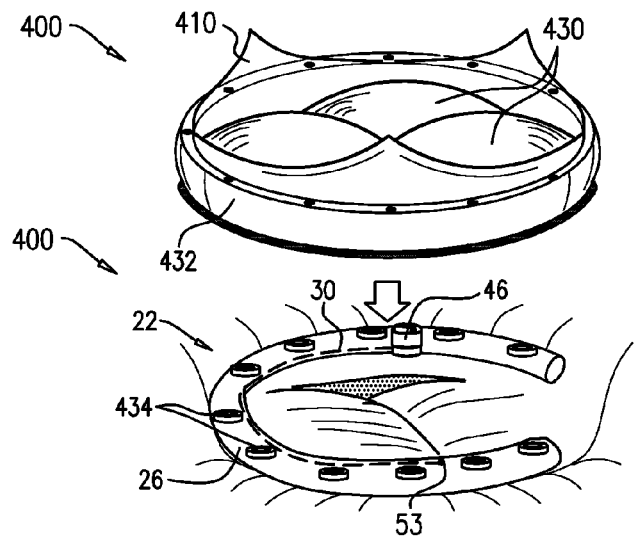

For some applications, the techniques of this configuration are implemented using techniques described in US Patent Application Publication 2010/0161047, which is incorporated herein by reference, with reference to FIG. 15 thereof, mutatis mutandis.

Figure 14A:
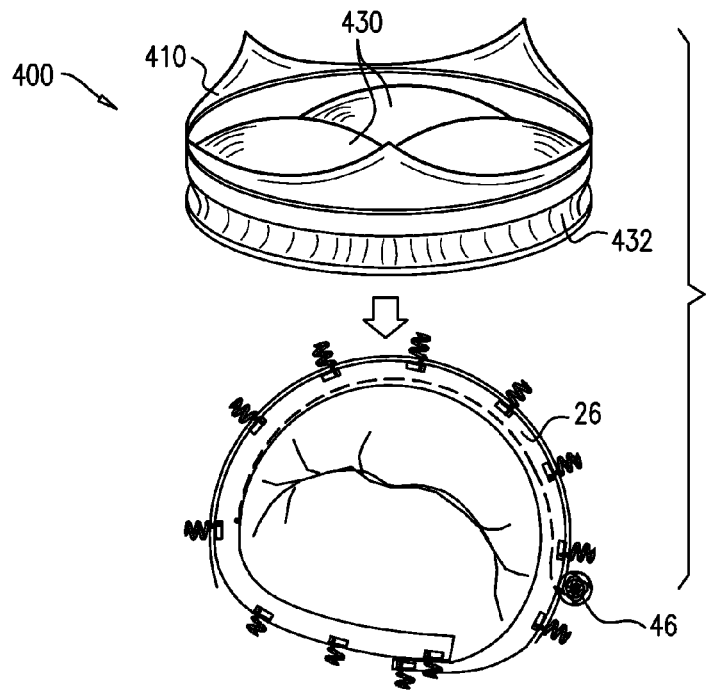
FIGS. 14A-B and 15 are schematic illustrations of a valve prosthesis assembly, in accordance with respective applications of the present invention.
Figure 14B:
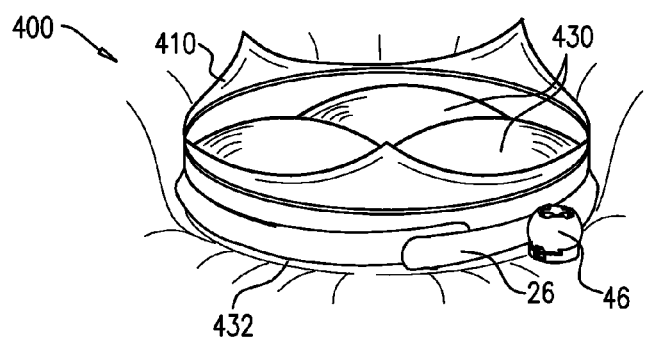

Reference is made to FIGS. 14A-B and 15, which are schematic illustrations of a valve prosthesis assembly 400, in accordance with respective applications of the present invention. Valve prosthesis assembly 400 comprises a prosthetic heart valve 410 that is couplable to a base ring 422. Prosthetic heart valve 410 is used to replace a native diseased heart valve. Valve 410 comprises a plurality of artificial leaflets 430, which comprise a pliant material. Valve 410 may implement techniques known in the artificial valve art, such as described, for example, in US Patent Application Publication 2007/0255400 to Parravicini et al., US Patent Application Publication 2004/0122514 to Fogarty et al., US Patent Application Publication 2007/0162111 to Fukamachi et al., and/or US Patent Application Publication 2008/0004697 to Lichtenstein et al., all of which are incorporated herein by reference.

Valve 410 further comprises an annular base 432, to which artificial leaflets 430 are coupled. Annular base 432 is configured to be couplable to base ring 422 during an implantation procedure. For example, as show in FIG. 15, base ring 422 may comprise one or more coupling elements 434, such as clips or magnets, which are configured to be coupled to corresponding coupling elements on a lower surface of annular base 432 (not visible in the figures). Alternatively or additionally, annular base 432 may be configured to be placed within the opening defined by base ring 422, as shown in FIG. 14A. To hold the annular base coupled to the base ring, the base ring is tightened around the annular base, as shown in FIG. 14B, typically using one or more of the techniques described hereinabove for contracting implant structures. Typically, valve prosthesis assembly 400, such as annular base 432 thereof, is configured to push and hold open the intact diseased native leaflets.

Base ring 422 implements one or more of the techniques of implantable structure 22 described hereinabove. In particular, base ring 422 may be coupled to the annulus of the native diseased valve using the anchoring techniques described hereinabove. In addition, base ring 422 typically comprises sleeve 26 and contracting mechanism 28, which may, for some applications, comprise a rotatable structure 46, such as a spool, which is typically implemented using techniques described herein. The contracting mechanism is arranged to contract base ring 422, e.g., the rotatable structure is arranged such that rotation thereof contracts base ring 422, typically using techniques described herein. Such tightening may serve to couple base ring 422 to annular base 432, as shown in FIG. 14B. Alternatively or additionally, such tightening sets the desired dimensions of the base ring, in order to align the coupling elements of the base ring with those of valve 410, thereby enabling tight coupling, such as for the applications described with reference to FIG. 15.

For some applications, as shown in FIG. 15, base ring 422 comprises a partial ring, such as described hereinabove with reference to FIGS. 2A-I. For other applications, as shown in FIGS. 14A-B, the base ring is arranged as a full ring, such as described hereinabove with reference to FIGS. 4, 6, and 8.

Valve prosthesis assembly 400 is typically implanted in a minimally invasive transcatheter or percutaneous procedure. The procedure begins with the introduction and implantation of base ring 422 into the heart, such as using techniques for implanting implantable structure 22, described hereinabove with reference to FIGS. 2A-I. Prosthetic heart valve 410 is subsequently introduced into the heart and coupled to base ring 422, as described above. Valve prosthesis assembly 400 is typically used for replacement of a diseased native mitral valve, aortic valve, tricuspid valve, or pulmonary valve.

Figure 16:
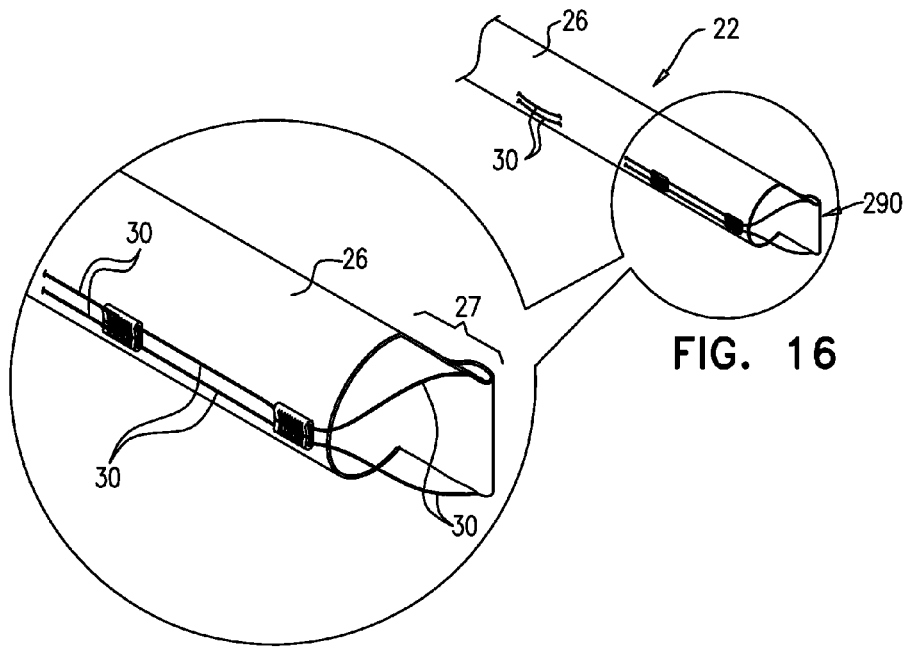
FIGS. 16 and 17A-B are schematic illustrations of closure mechanisms, in accordance with respective applications of the present invention.
Figures 17A, 17B:
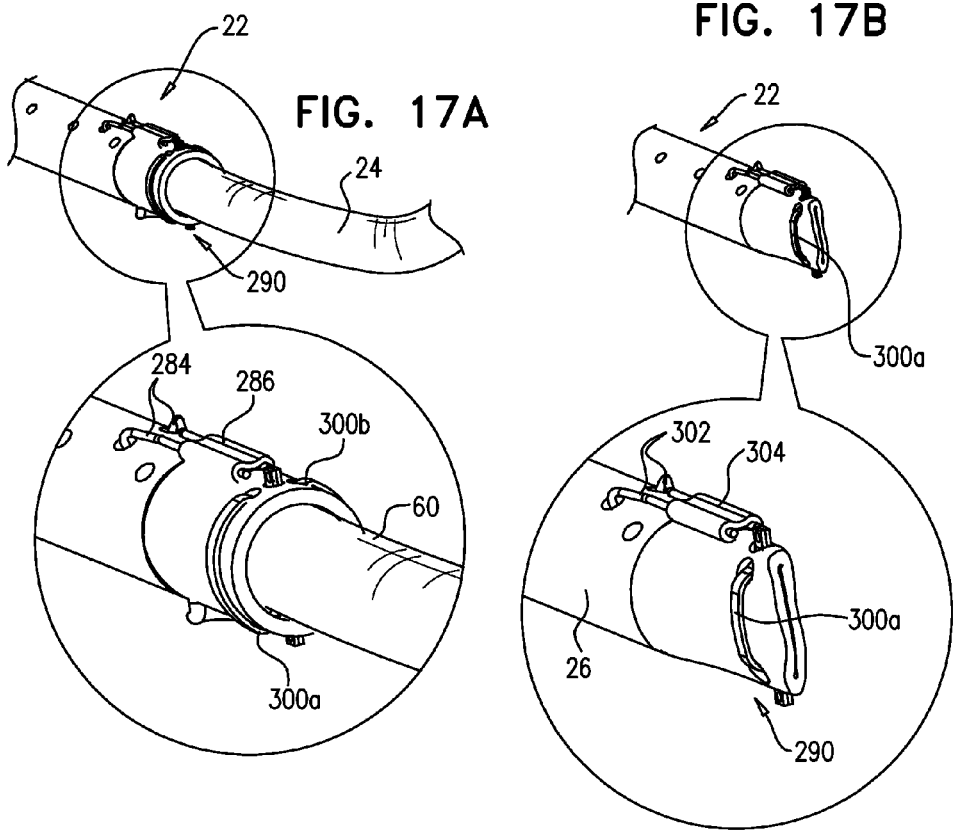

Reference is now made to FIGS. 16 and 17A-B, which are schematic illustrations of a closure mechanism 290, in accordance with respective applications of the present invention. Typically, one of proximal end 59 and distal end 51 of sleeve 26 is permanently closed. The other end is at least initially open, to allow anchor deployment manipulator 24 to be inserted into a lumen of sleeve 26 during an implantation procedure, such as described hereinabove with reference to FIGS. 2G-I. For some applications, implantable structure 22 comprises closure mechanism 290 to close the initially open end after the anchor deployment manipulator has been withdrawn from the sleeve.

In the exemplary configuration of closure mechanism 290 shown in FIG. 16, the initially open end of the sleeve is shaped so as to provide a first end flap 27 which is coupled to (e.g., by being looped through) a portion of contracting member 30. When contracting assembly 40 is actuated, contracting member 30 is pulled or released in order to close or open flap 27 over the opening of the sleeve. Thus, implant structure 22 comprises a closure element (e.g., closure mechanism 290) for closing the opening of the sleeve end. Typically, contracting mechanism 290 is remotely-controlled by the operating physician. Following the closing of flap 27 over the opening, contracting mechanism 28 facilitates contracting of implant structure 22, as described hereinabove.

In the exemplary configuration of closure mechanism 290 shown in FIG. 17A-B, closure mechanism 290 comprises self-closing strips 300a and 300b, which are typically coupled to (e.g., by being threaded through) portions of the initially open end of sleeve 26 in a vicinity of the opening. Strips 300a and 300b define generally arcuate elements which comprise a flexible material (e.g., Nitinol). Strips 300a and 300b have a tendency to close and assume the configuration shown in FIG. 17B. Strips 300a and 300b are opened from their closed state when a tool (e.g., such as anchor deployment manipulator 24, as shown) is advanced within the lumen of sleeve 26 (as shown in FIG. 17A). Once the tool is removed from within the lumen, strips 300a and 300b assume their biased state, thereby closing the opening at the end of implant structure 22. Thus, strips 300a and 300b are automatically-activatable when the tool is removed from the lumen of sleeve 26.

For some applications, strips 300a and 300b are coupled to respective strings 302 which couple strips 300a and 300b to sleeve 26. Strings 302 may be crimped together by a crimp 304.

As shown in FIG. 17A, manipulator 24 is advanceable within the lumen of sleeve 26 so as to facilitate anchoring of structure 22 using anchors 38, such as described hereinabove with reference to FIGS. 2G-I. Following the anchoring, contracting assembly 40 is actuated in order to adjust a dimension of structure 22. As described hereinabove, contracting assembly 40 adjusts a tension of contracting member 30 coupled thereto. Since contracting member 30 may be threaded through sleeve 26, as shown, the adjusting of the tension of contracting assembly 30 adjusts the dimension of sleeve 26 and thereby, of implant structure 22. Following the adjusting, manipulator 24 is then removed from the body of the patient, allowing strips 300a and 300b to close around the opening, and structure 22 remains within the heart.

Alternatively or additionally, other closure elements may be used for closing the opening at the end of the sleeve. For example, a plug (such as a silicone plug), and/or a band (such as a silicone band) may be used to close the opening. Alternatively, flap 27 may be folded over and an anchor (e.g., a tissue anchor 38, as described herein) may be used to anchor the folded-over flap to the patient's tissue.

Typically, the closure elements described herein reduce the likelihood of a thrombosis forming inside sleeve 26, by closing the opening of the sleeve end, relative to if the opening were left opened. Alternatively or additionally, the closure elements described herein are used to close the opening for a different reason.

Typically, the closure of the opening (e.g., using the closure elements described herein) and the deployment of implant structure 22 is performed during a single procedure, e.g., by deploying the implant structure and closing the opening via a single catheter. For some applications (not shown), sleeve 26 defines openings at both thereof, and closure elements are used to close the openings at both of the ends of the sleeve.

For some applications, system 20 further comprises a flexible pusher element, such as described and shown in US Patent Application Publication 2010/0286767, which is incorporated herein by reference, with reference to FIG. 8 thereof. The pusher element aids with accurately positioning successive anchors 38 during an implantation procedure, such as described hereinabove with reference to FIGS. 2H and 2I. For some applications, system 20 further comprises a pusher tube that is applied to proximal end 49 of sleeve 26, such as described in the above-mentioned '604 publication, with reference to FIGS. 14 and/or 18A-B thereof. For some applications, system 20 further comprises a steerable tube, such as described in the above-mentioned '604 publication, with referenced to FIG. 15 thereof, or with reference to FIG. 16 thereof. For some applications, system 20 further comprises a pulling wire, such as described in the above-mentioned '604 publication, with referenced to FIG. 17 thereof. For some applications, system 20 further comprises an external control handle, such as described in the above-mentioned '604 publication, with referenced to FIG. 19 thereof. For some applications, contracting assembly 40 and implant structure 22 are configured as described with reference to FIG. 23 of the above-mentioned '604 publication, mutatis mutandis.

For some applications of the present invention, system 20 is used to treat an atrioventricular valve other than the mitral valve, i.e., the tricuspid valve. For these applications, implantable structure 22 and other components of system 20 described hereinabove as being placed in the left atrium are instead placed in the right atrium. Although implantable structure 22 is described hereinabove as being placed in an atrium, for some application the implantable structure is instead placed in either the left or right ventricle.

The scope of the present invention includes applications described in the following applications, which are incorporated herein by reference. In an application, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001,503 to Gross et al., entitled, "Segmented ring placement," filed on Dec. 5, 2007, which published as PCT Publication WO 08/068,756;

U.S. patent application Ser. No. 11/950,930 to Gross et al., entitled, "Segmented ring placement," filed on Dec. 5, 2007, which published as US Patent Application Publication 2008/0262609;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabin, entitled, "Adjustable partial annuloplasty ring and mechanism therefor," filed on Dec. 22, 2008, which published as US Patent Application Publication 2010/0161047;

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009, which published as US Patent Application Publication 2010/0161041;

U.S. patent application Ser. No. 12/437,103 to Zipory et al., entitled, "Annuloplasty ring with intra-ring anchoring," filed on May 7, 2009, which published as US Patent Application Publication 2010/0286767;

PCT Patent Application PCT/IL2009/000593 to Gross et al., entitled, "Annuloplasty devices and methods of delivery therefor," filed on Jun. 15, 2009, which published as PCT Publication WO 10/004,546;

U.S. patent application Ser. No. 12/548,991 to Maisano et al., entitled, "Implantation of repair chords in the heart," filed on Aug. 27, 2009, which published as US Patent Application Publication 2010/0161042;

U.S. patent application Ser. No. 12/608,316 to Miller et al., entitled, "Tissue anchor for annuloplasty ring," filed on Oct. 29, 2009, which published as US Patent Application Publication 2011/0106247;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabin et al., entitled, "Adjustable annuloplasty devices and mechanisms therefor," filed on Dec. 22, 2009, which published as PCT Publication WO 10/073,246;

U.S. patent application Ser. No. 12/689,635 to Zipory et al., entitled, "Over-wire rotation tool," filed on Jan. 19, 2010, which published as US Patent Application Publication 2010/0280604;

U.S. patent Ser. No. 12/689,693 to Hammer et al., entitled, "Deployment techniques for annuloplasty ring," filed on Jan. 19, 2010, which published as US Patent Application Publication 2010/0280605;

U.S. patent application Ser. No. 12/706,868 to Miller et al., entitled, "Actively-engageable movement-restriction mechanism for use with an annuloplasty structure," filed on Feb. 17, 2010, which published as US Patent Application Publication 2010/0211166;

PCT Patent Application PCT/IL2010/000357 to Maisano et al., entitled, "Implantation of repair chords in the heart," filed May 4, 2010, which published as PCT Publication WO 2010/128502;

PCT Patent Application PCT/IL2010/000358 to Zipory et al., entitled, "Deployment techniques for annuloplasty ring and over-wire rotation tool," filed May 4, 2010, which published as PCT Publication WO 2010/128503; and/or U.S. patent application Ser. No. 13/167,476 to Hammer et al., filed on Jun. 23, 2011 on even date herewith, entitled, "Closure element for use with an annuloplasty structure," which published as US Patent Application Publication 2012/0330410.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of valve repair comprising:
providing an implantable structure, which includes (a) a flexible sleeve, which defines a lumen and has first and second sleeve ends, and (b) a contracting assembly, which is configured to longitudinally contract the flexible sleeve, and which includes (i) a contracting mechanism, which comprises a housing, and (ii) one or more longitudinal contracting members coupled to the contracting mechanism;
placing the implantable structure in a closed loop completely around an annulus of an atrioventricular valve of a subject, such that none of the one or more longitudinal contracting members is positioned along an anterior portion of the annulus between fibrous trigones of the valve;
fastening the implantable structure to the annulus;
tightening at least a portion of a posterior portion of the annulus, while preserving a length of the anterior portion of the annulus, by tightening the implantable structure by actuating the contracting assembly to cause the one or more longitudinal contracting members to apply a longitudinal contracting force to a longitudinal portion of the flexible sleeve not positioned along the anterior portion of the annulus; and
leaving the entire implantable structure in a body of the subject after completing the valve repair.

2. The method according to claim 1,
wherein the one or more longitudinal contracting members are positioned at least partially within the lumen of the flexible sleeve,
wherein the flexible sleeve has first and second portions that longitudinally extend from the first and the second sleeve ends, respectively,
wherein placing the implantable structure in the closed loop comprises arranging the flexible sleeve in the closed loop such that the first and second portions of the flexible sleeve overlap each other so as to together define a longitudinally overlapping portion of the flexible sleeve positioned at least partially along the anterior portion of the annulus, and
wherein none of the one or more longitudinal contracting members is positioned along the longitudinally overlapping portion of the flexible sleeve.

3. The method according to claim 2,
wherein fastening the implantable structure to the annulus comprises fastening the flexible sleeve to the annulus using a plurality of tissue anchors, at least one of which penetrates both the first and second portions of the sleeve at the longitudinally overlapping portion, wherein the plurality of tissue anchors includes a plurality of first tissue anchors of a first configuration, and a plurality of second tissue anchors of a second configuration different from the first configuration, and wherein fastening the implantable structure to the annulus comprises:

coupling the first tissue anchors to the flexible sleeve at intervals along a first longitudinally-contiguous portion of the closed loop positioned along a portion of the annulus other than the anterior portion of the annulus, and coupling the second tissue anchors to the sleeve at intervals along a second longitudinally-contiguous portion of the closed loop positioned along the anterior portion of the annulus.

4. The method according to claim 2, wherein providing the implantable structure comprises providing the implantable structure in which none of the one or more contracting members extends along the first portion of the flexible sleeve, or along the second portion of the flexible sleeve.

5. The method according to claim 2, wherein fastening the implantable structure to the annulus comprises fastening the flexible sleeve to the annulus using a plurality of tissue anchors, at least one of which penetrates both the first and second portions of the sleeve at the longitudinally overlapping portion.

6. The method according to claim 5, wherein the at least one of the plurality of tissue anchors includes a coupling head and a tissue coupling element, and wherein fastening the flexible sleeve to the annulus comprises fastening the flexible sleeve to the annulus such that the tissue coupling element penetrates both the first and second portions of the flexible sleeve at the longitudinally overlapping portion, and the coupling head is positioned within one of the first and second portions of the flexible sleeve at the longitudinally overlapping portion.

7. The method according to claim 1, wherein placing the implantable structure comprises placing the implantable structure such that the one or more longitudinal contracting members are positioned along a non-anterior portion of the annulus, which non-anterior portion does not reach either of the fibrous trigones.

8. The method according to claim 1, wherein placing the implantable structure in the closed loop comprises introducing the flexible sleeve into an atrium while the first and the second sleeve ends are not coupled to each other.

9. A method of valve repair comprising:

providing an implantable structure, which includes (a) a flexible sleeve, which defines a lumen and has first and second sleeve ends, and (b) a contracting assembly, which is configured to longitudinally contract the flexible sleeve, and which includes (i) a contracting mechanism, which is disposed longitudinally at a first site of the flexible sleeve, and (ii) a longitudinal contracting member which is positioned at least partially within the lumen, and has (x) a first member end, (y) a second member end, which is fixed to the flexible sleeve longitudinally at a second site, which is longitudinally between the first site and the second sleeve end, exclusive, and (z) a first member end portion, which (1) extends from the first member end toward the second member end along only a longitudinal portion of the longitudinal contracting member, and (2) is coupled to the contracting mechanism;

placing the implantable structure at least partially around an annulus of an atrioventricular valve of a subject;

using a plurality of tissue anchors, fastening the implantable structure to the annulus, including coupling one or more of the plurality of tissue anchors to the flexible sleeve and tissue of the annulus at respective third sites longitudinally between the second site and the second sleeve end, exclusive;

actuating the contracting assembly to contract a longitudinal portion of the flexible sleeve; and leaving the entire implantable structure in a body of the subject after completing the valve repair.

10. The method according to claim 9, wherein a first portion of the flexible sleeve longitudinally extends from the first sleeve end toward the first site, wherein a second portion of the flexible sleeve longitudinally extends from the second sleeve end toward the second site, and wherein placing the implantable structure comprises arranging the flexible sleeve in a closed loop, such that the first and second portions of the flexible sleeve overlap each other so as to together define a longitudinally overlapping portion of the flexible sleeve.

11. The method according to claim 10, wherein placing the implantable structure comprises placing the implantable structure such that the longitudinally overlapping portion is positioned along an anterior portion of the annulus between fibrous trigones of the valve.

12. The method according to claim 10, wherein fastening comprises coupling at least one of the plurality of tissue anchors to the tissue such that the anchor penetrates both the first and second portions of the sleeve at the longitudinally overlapping portion.

13. The method according to claim 10, wherein providing the implantable structure comprises providing the implantable structure in which the longitudinally overlapping portion has a length of between 5 and 60 mm.

14. The method according to claim 10, wherein providing the implantable structure comprises providing the implantable structure in which the longitudinal contracting member does not extend along the first portion of the flexible sleeve, and does not extend along the second portion of the flexible sleeve.

15. The method according to claim 9, wherein coupling the one or more of the plurality of tissue anchors comprises coupling at least two of the tissue anchors to the flexible sleeve and the tissue at respective third sites longitudinally between the second member end and the second sleeve end, exclusive.

16. The method according to claim 9, wherein providing the implantable structure comprises providing the implantable structure in which the second site is at least 5 mm from the second sleeve end, measured when the flexible sleeve is in a straight, relaxed, non-contracted state.

17. The method according to claim 9, wherein providing the implantable structure comprises providing the implantable structure in which the second site is at a longitudinal distance from the second sleeve end, which distance is no greater than 30% of a total length of the flexible sleeve, the distance and length measured when the flexible sleeve is in the straight, relaxed, non-contracted state.

18. The method according to claim 9, wherein coupling the one or more of the plurality of tissue anchors comprises coupling at least three of the plurality of tissue anchors to the flexible sleeve alongside the longitudinal contracting member, longitudinally between the first and second sites, exclusive.

19. The method according to claim 9, wherein actuating the contracting assembly comprises actuating the contracting assembly to apply a longitudinal contracting force only between the first and the second sites along the longitudinal contracting member.

20. The method according to claim 9, wherein providing the implantable structure comprises providing the implantable structure in which the contracting mechanism comprises a housing, which is disposed longitudinally at the first site.

21. The method according to claim 9, wherein actuating the contracting assembly to contract the longitudinal portion of the flexible sleeve comprises actuating the contracting assembly to cause the longitudinal contracting member to apply a longitudinal contracting force to the longitudinal portion of the flexible sleeve.

22. A method of valve repair comprising:
providing an implantable structure, which includes (a) a flexible sleeve, which defines a lumen and has first and second sleeve ends, and (b) a contracting assembly, which includes (i) a contracting mechanism, which is disposed longitudinally at a first site of the flexible sleeve, and (ii) a longitudinal contracting member which is positioned at least partially within the lumen, and has (x) a first member end, (y) a second member end, which is fixed to the flexible sleeve longitudinally at a second site, which is longitudinally between the first site and the second sleeve end, exclusive, and (z) a first member end portion, which (1) extends from the first member end toward the second member end along only a longitudinal portion of the longitudinal contracting member, and (2) is coupled to the contracting mechanism, wherein the contracting mechanism is configured to apply a longitudinal contracting force only between the first and the second sites; and
placing the implantable structure at least partially around an annulus of an atrioventricular valve of a subject;
using a plurality of tissue anchors, fastening the implantable structure to the annulus, including coupling one or more of the plurality of tissue anchors to the flexible sleeve and tissue of the annulus at respective third sites selected from the group of sites consisting of: one or more sites longitudinally between the first site and the first sleeve end, exclusive, and one or more sites longitudinally between the second site and the second sleeve end, exclusive;
actuating the contracting assembly to contract a longitudinal portion of the flexible sleeve by applying the longitudinal contracting force only between the first and the second sites; and
leaving the entire implantable structure in a body of the subject after completing the valve repair.

23. The method according to claim 22, wherein at least one of the third sites is longitudinally between the first site and the first sleeve end, exclusive.

24. The method according to claim 23, wherein at least two of the third sites are longitudinally between the first site and the first sleeve end, exclusive.

25. The method according to claim 22, wherein at least one of the third sites is longitudinally between the second site and the second sleeve end, exclusive.

26. The method according to claim 25, wherein at least two of the third sites are longitudinally between the second site and the second sleeve end, exclusive.

27. The method according to claim 22, wherein at least one of the third sites is longitudinally between the first site and the first sleeve end, exclusive, and wherein at least one of the third sites is longitudinally between the second site and the second sleeve end, exclusive.

28. The method according to claim 22, wherein providing the implantable structure comprises providing the implantable structure in which the first site is a first longitudinal distance from the first sleeve end, the second site is at a second longitudinal distance from the second sleeve end, which first and second longitudinal distances are measured when the flexible sleeve is in a straight, relaxed, non-contracted state, and at least one of the first and second longitudinal distances, taken separately, is at least 5 mm.

29. The method according to claim 22, wherein a first portion of the flexible sleeve longitudinally extends from the first sleeve end toward the first site, wherein a second portion of the flexible sleeve longitudinally extends from the second sleeve end toward the second site, and wherein placing the implantable structure comprises arranging the flexible sleeve in a closed loop, such that the first and second portions of the sleeve overlap each other so as to together define a longitudinally overlapping portion of the flexible sleeve.

30. The method according to claim 22,
wherein the longitudinal portion of the flexible sleeve is only between the first and the second sites, along at least a portion of the longitudinal contracting member, and
wherein actuating comprises actuating the contracting mechanism to contract the longitudinal portion of the flexible sleeve by applying the longitudinal contracting force only between the first and the second sites along the longitudinal contracting member.

31. The method according to claim 22, wherein providing the implantable structure comprises providing the implantable structure in which the contracting mechanism comprises a housing, which is disposed longitudinally at the first site.

32. The method according to claim 22, wherein actuating the contracting assembly to contract the longitudinal portion of the flexible sleeve comprises actuating the contracting assembly to cause the longitudinal contracting member to apply the longitudinal contracting force to the longitudinal portion of the flexible sleeve only between the first and the second sites.

* * * * *